United States Patent
Rongved et al.

(10) Patent No.: US 10,227,327 B2
(45) Date of Patent: Mar. 12, 2019

(54) INHIBITORS OF METALLO-BETA-LACTAMASE (MBL) COMPRISING A ZINC CHELATING MOIETY

(71) Applicant: Universitetet I Oslo, Oslo (NO)

(72) Inventors: Pål Rongved, Oslo (NO); Ove Alexander Høgmoen Åstrand, Oslo (NO); Annette Bayer, Tromsø (NO); Hanna-Kirsti Schrøder Leiros, Tromsø (NO); Ørjan Samuelsen, Tromsø (NO); Kine Susann Waade Edvardsen, Paradis (NO); Zeeshan Muhammad, Tromsø (NO)

(73) Assignee: Universitetet I Oslo, Oslo (NO)

( * ) Notice: Subject to any disclaimer, the term of this patent is extended or adjusted under 35 U.S.C. 154(b) by 0 days.

(21) Appl. No.: 15/027,140

(22) PCT Filed: Oct. 6, 2014

(86) PCT No.: PCT/GB2014/053009
§ 371 (c)(1),
(2) Date: Apr. 4, 2016

(87) PCT Pub. No.: WO2015/049546
PCT Pub. Date: Apr. 9, 2015

(65) Prior Publication Data
US 2016/0244431 A1    Aug. 25, 2016

(30) Foreign Application Priority Data
Oct. 4, 2013   (GB) .................................. 1317619.3

(51) Int. Cl.
*A61K 45/06*    (2006.01)
*A61P 31/04*    (2006.01)
(Continued)

(52) U.S. Cl.
CPC .......... *C07D 401/14* (2013.01); *A61K 31/444* (2013.01); *A61K 38/05* (2013.01);
(Continued)

(58) Field of Classification Search
None
See application file for complete search history.

(56) References Cited

U.S. PATENT DOCUMENTS

| 6,410,570 B1 | 6/2002 | Fernandez-Pol |
| 2003/0039956 A1 | 2/2003 | Choi et al. |

(Continued)

FOREIGN PATENT DOCUMENTS

| RU | 2 491 009 C2 | 8/2013 |
| WO | 97/10225 A1 | 3/1997 |

(Continued)

OTHER PUBLICATIONS

CDC, "Guideline for Disinfection and Sterilization in Healthcare Facilities, 2008", Accessible at URL cdc.gov/infectioncontrol/guidelines/disinfection/, pp. 1-161.*

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

Compounds according to formula I are provided:

A-L-B wherein A represents a lipophilic chelating moiety which is selective for $Zn^{2+}$ ions; L is a covalent bond or a linker; and B is a vector which is either a moiety capable of interacting with one or more biological structures found in a bacterium (preferably in a bacterial cell wall), for example a penicillin-binding protein such as a metallo-β-lactamase or DD-transferase, or a moiety capable of enhancing transport of the (Continued)

compound across a bacterial cell membrane. A method of treating and/or preventing a bacterial infection in a human or non-human mammal employing such compounds are also provided. In such a method, the compound of formula I may be administered in combination with (either simultaneously, separately, or sequentially) a β-lactam antibiotic.

15 Claims, 2 Drawing Sheets

(51) Int. Cl.
    *C07D 401/14*     (2006.01)
    *A61K 31/444*     (2006.01)
    *A61K 38/05*     (2006.01)
    *C07D 405/14*     (2006.01)
    *C07K 5/062*     (2006.01)
    *A61K 47/64*     (2017.01)

(52) U.S. Cl.
    CPC .............. *A61K 45/06* (2013.01); *A61K 47/64* (2017.08); *C07D 405/14* (2013.01); *C07K 5/06026* (2013.01)

(56) References Cited

U.S. PATENT DOCUMENTS

| | | |
|---|---|---|
| 2003/0225155 A1 | 12/2003 | Fernandez-Pol et al. |
| 2005/0013836 A1 | 1/2005 | Raad |
| 2006/0014230 A1 | 1/2006 | Murata |
| 2009/0111737 A1 | 4/2009 | Christensen et al. |
| 2012/0329842 A1 | 12/2012 | Song et al. |

FOREIGN PATENT DOCUMENTS

| | | |
|---|---|---|
| WO | 97/30027 A1 | 8/1997 |
| WO | 98/17639 A1 | 4/1998 |
| WO | 98/39311 A1 | 9/1998 |
| WO | 98/40056 A2 | 9/1998 |
| WO | 00/076962 A1 | 12/2000 |
| WO | 01/030148 A1 | 5/2001 |
| WO | 01/030149 A1 | 5/2001 |
| WO | 2001/60349 A2 | 8/2001 |
| WO | 2004/71425 A2 | 8/2004 |
| WO | 2005/117997 A1 | 12/2005 |
| WO | 2006/43153 A2 | 4/2006 |
| WO | 2006/109069 A1 | 10/2006 |
| WO | 2006/117660 A2 | 11/2006 |
| WO | 2009/031041 A2 | 3/2009 |
| WO | 2009/140215 A2 | 11/2009 |
| WO | 2009/155088 A1 | 12/2009 |
| WO | 2011/63394 A2 | 5/2011 |
| WO | 2012/088283 A1 | 6/2012 |

OTHER PUBLICATIONS

Bush, "Bench-to-bedside review: the role of β-lactamases in antibiotic-resistant Gram-negative infections," Critical Care 14:224, pp. 1-8 (2010).*
Woodford et al., "Infections caused by Gram-positive bacteria: a review of the global challenge," J. Infect. 59: S4 S16 (2009).*
Astrand, O.A., et al., "Synthesis and Initial in Vitro Biological Evaluation of Two New Zinc-Chelating Compounds: Comparison with TPEN and PAC-1", Bioorganic & Medicinal Chemistry, 2013, vol. 21(17), pp. 5175-5181, doi:10.1016/j.bmc.2013.06.037, Epub Jun. 26, 2013.
Astrand, O., et al., "Synthesis and Characterization of New Selective Zn2+ Fluorescent Probes for Functionalization: In Vitro Cell Imaging Applications", Tetrahedron, 2013, vol. 69, pp. 8645-8654, Epub Aug. 1, 2013.
Brotherton, W.S., et al., "Apparent Copper(II)-Accelerated Azide-Alkyne Cycloaddition", Organic Letters, 2009, vol. 11(21), pp. 4954-4957, doi: 10.1021/ol9021113, Epub Oct. 7, 2009.
Huang, S., et al., "Highly Sensitive Fluorescent Probes for Zinc Ion Based on Triazolyl-Containing Tetradentate Coordination Motifs", Organic Letters, 2007, vol. 9(24), pp. 4999-5002, Epub Oct. 23, 2007.
Moore, A.L., et al., ""Click" Labeling Strategy for M(CO)(3) (M=Re, (99m)Tc) Prostate Cancer Targeted Flutamide Agents", Dalton Trans., 2010, vol. 39(8), pp. 1926-1928, doi:10.1039/b921413e, Epub Jan. 6, 2010.
Sutoh, Y., et al., "Metal Chelates to Prevent or Clear the Deposits of Amyloid β-peptide(1-40) Induced by Zinc(II) Chloride" Chemistry Letters, 2005, vol. 34(2), pp. 140-141, Epub Feb. 5, 2005.
International Search Report, PCT/GB2014/053009, dated Dec. 17, 2014, pp. 1-6.
Written Opinion of the International Searching Authority, PCT/GB2014/053009, dated Dec. 17, 2014, pp. 1-9.
Barkalifa, R., et al., "The Lipophilic Zinc Chelator DP-b99 Prevents Zinc Induced Neuronal Death", Eur. J. Pharmacol, Sep. 15, 2009, vol. 618(1-3), pp. 15-21, doi:10.1016/j.ejphar.2009.07.019, Epub Jul. 19, 2009. (Abstract only).
Bertini, I., et al., "A Bioinformatics View of Zinc Enzymes", Journal of Inorganic Biochemistry, Jun. 2012, vol. 111, pp. 150-156, doi. org/10.1016/j.jinorgbio.2011.11.020. (Abstract only).
Bozym, R.A., et al., "Free Zinc Ions Outside a Narrow Concentration Range Are Toxic to a Variety of Cells in Vitro", Exp. Biol. Med. (Maywood), Jun. 1, 2010, vol. 235(6), pp. 741-750, doi:10.1258/ebm.2010.009258.
Bush, K., et al., "Epidemiological Expansion, Structural Studies, and Clinical Challenges of New β-Lactamases from Gram-Negative Bacteria", Annual Review of Microbiology, Oct. 2011, vol. 65, pp. 455-478, doi.org/10.1146/annurev-micro-090110-102911. (Abstract only).
Butler, M.S., et al., "Antibiotics in the Clinical Pipeline in 2013", The Journal of Antibiotics, Sep. 4, 2013, vol. 66, pp. 571-591, doi:10.1038/ja.2013.86.
Charkoudian, L.K., et al., "A Pro-Chelator Triggered by Hydrogen Peroxide Inhibits Iron-Promoted Hydroxyl Radical Formation", J. Am. Chem. Soc., 2006, vol. 128(38), pp. 12424-12425, doi:10. 1021/ja064806w. (Abstract only).
Conrady, D.G., et al., "A Zinc-Dependent Adhesion Module is Responsible for Intercellular Adhesion in Staphylococcal Biofilms", Proc. Natl. Acad. Sci. USA, Dec. 9, 2008, vol. 105(49), pp. 19456-19461. doi:10.1073/pnas.0807717105, Epub Dec. 1, 2008.
de Kraker M.E.A., et al., "Mortality and Hospital Stay Associated with Resistant *Staphylococcus aureus* and *Escherichia coli* Bacteremia: Estimating the Burden of Antibiotic Resistance in Europe", PLoS Med., Oct. 2011, vol. 8(10), p. e1001104, doi:10.1371/journal.pmed. 1001104, Epub Oct. 11, 2011.
Donadelli, M., et al., "Zinc Depletion Efficiently Inhibits Pancreatic Cancer Cell Growth by Increasing the Ratio of Antiproliferative/Proliferative Genes", J. Cell. Biochem., May 1, 2008, vol. 104(1), pp. 202-212. (Abstract only).
Drawz, S.M., et al., "New β-lactamase Inhibitors: A Therapeutic Renaissance in an MDR World", Antimicrob. Agents Chemother., Apr. 2014, vol. 58(4), pp. 1835-1846, doi:10.1128/AAC.00826-13, Epub Dec. 30, 2013.
Drawz, S.M., et al., "Three Decades of β-Lactamase Inhibitors", Clin. Microbiol. Rev., Jan. 2010, vol. 23(1), pp. 160-201, doi:10. 1128/CMR.00037-09.
Ellison, M.L., et al., "The Transcriptional Regulator Np20 is the Zinc Uptake Regulator in Pseudomonas aeruginosa", PLoS One, Sep. 23, 2013, vol. 8(9), e75389, pp. 1-11, doi:10.1371/journal. pone.0075389, eCollection 2013.
Ganta, S.R., et al., "Approaches to the Simultaneous Inactivation of Metallo- and Serine-β-Lactamases", Bioorg. Med. Chem. Lett., Mar. 15, 2009, vol. 19(6), pp. 1618-1622, doi:10.1016/j.bmcl.2009. 02.018, Epub Feb. 8, 2009.
Goto, M., et al., "Inhibition of the Metallo-Beta-Lactamase Produced from Serratia Marcescens by Thiol Compounds", Biol. Pharm. Bull., Nov. 1997, vol. 20(11), pp. 1136-1140. (Abstract only).

(56) References Cited

OTHER PUBLICATIONS

Graham, A.I., et al., "Severe Zinc Depletion of *Escherichia coli*: Roles for High Affinity Zinc Binding by ZinT, Zinc Transport and zinc-Independent Proteins", J. Biol. Chem., Jul. 3, 2009, vol. 284(27), pp. 18377-18389, doi:10.1074/jbc.M109.001503, Epub Apr. 19, 2009.

Hsu, D.C., et al., "Parallel Synthesis and Biological Evaluation of 837 Analogues of Procaspase-Activating Compound 1 (PAC-1)", ACS Comb. Sci., Jan. 9, 2012, vol. 14(1), pp. 44-50, doi:10.1021/co2001372, Epub Oct. 28, 2011.

Johnson, A.P., et al., "Global Spread of Antibiotic Resistance: The Example of New Delhi Metallo-β-Lactamase (NDM)-mediated Carbapenem Resistance", J. Med. Microbiol., Apr. 2013, vol. 62(Pt 4), pp. 499-513, doi:10.1099/jmm.0.052555-0, Epub Jan. 17, 2013. (Abstract only).

King, A.M., et al., "AMA Overcomes Antibiotic Resistance by NDM and VIM Metallo-β-Lactamases", Nature, Jun. 26, 2014, vol. 510(7506), pp. 503-506, doi:10.1038/nature13445.

Liang, X., et al., "Synthesis, Structure, and Antibiotic Activity of Aryl-Substituted LpxC Inhibitors", J. Med. Chem., Sep. 12, 2013, vol. 56(17), pp. 6954-6966, doi:10.1021/jm4007774, Epub Aug. 21, 2013.

Liu, L., et al., "Synthesis of Novel Macrolide Derivatives with Imidazo[4,5-b]Pyridinyl Sulfur Contained Alkyl Side Chains and their Antibacterial Activity", Bioorganic & Medicinal Chemistry Letters, Aug. 1, 2009, vol. 19(15), pp. 4079-4083. (Abstract only).

"List of Clinically Important Bacteria", Wikipedia, http://en.wikipedia.org/wiki/List_of_clinically_important_bacteria.

Makhov, P., et al., "Zinc Chelation Induces Rapid Depletion of the X-Linked Inhibitor of Apoptosis (XIAP) and Sensitizes Prostate Cancer Cells to TRAIL-Mediated Apoptosis", Cell Death Differ., Nov. 2008, vol. 15(11), pp. 1745-1751, doi:10.1038/cdd.2008.106, Epub Jul. 11, 2008.

Maret, W., et al., "Cellular Zinc and Redox Buffering Capacity of Metallothionein/Thionein in Health and Disease", Mol. Med., Jul.-Aug. 2007, vol. 13(7-8), pp. 371-375.

Martinez, J.L., "The Antibiotic Resistome: Challenge and Opportunity for Therapeutic Intervention", Future Med. Chem., Mar. 2012, vol. 4(3), pp. 347-359, doi:10.4155/fmc.12.2. (Abstract only).

Mikami, Y., et al., "Novel Microbial Inhibitors of Angiotensin-converting Enzyme, Aspergillomarasmines A and B", Agricultural and Biological Chemistry, 1983, vol. 47(11), pp. 2693-2695.

Napolitano, M., et al., "Characterization of the Response to Zinc Deficiency in the *Cyanobacterium Anabaena* sp. Strain PCC 7120", J. Bacteriol., May 2012, vol. 194(10), pp. 2426-2436, doi:10.1128/JB.00090-12, Epub Mar. 2, 2012.

Nikaido, H., et al., "Broad-Specificity Efflux Pumps and their Role in Multidrug Resistance of Gram-Negative Bacteria", FEMS Microbiology Reviews, Mar. 1, 2012, vol. 36(2), pp. 340-363, https://doi.org/10.1111/j.1574-6976.2011.00290.x.

Page, M.G.P., et al., "In Vitro and In Vivo Properties of BAL30376, a β-Lactam and Dual β-Lactamase Inhibitor Combination with Enhanced Activity Against Gram-Negative Bacilli that Express Multiple β-Lactamases", Antimicrob. Agents Chemother., Apr. 2011, vol. 55(4), pp. 1510-1519, doi:10.1128/AAC.01370-10, Epub Jan. 18, 2011.

Page, M.I., et al., "The Mechanism of Catalysis and the Inhibition of β-lactamases", Chem. Commun., 1998, pp. 1609-1617, doi:10.1039/A803578D. (Abstract only).

Palzkill, T., "Metallo-β-Lactamase Structure and Function", Ann. N.Y. Acad. Sci., Jan. 2013, vol. 1277, pp. 91-104. doi:10.1111/j.1749-6632.2012.06796.x, Epub Nov. 16, 2012.

Patel, G., et al., ""Stormy Waters Ahead": Global Emergence of Carbapenemases", Front. Microbiol., Mar. 14, 2013, vol. 4, Article 48, pp. 1-17, doi:10.3389/fmicb.2013.00048, eCollection 2013.

Payne, D.J., et al., "Inhibition of Metallo-Beta-Lactamases by a Series of Thiol Ester Derivatives of Mercaptophenylacetic Acid", FEMS Microbiol. Lett., Dec. 1, 1997, vol. 157(1), pp. 171-175. (Abstract only).

Payne, D.J., et al., "Inhibition of Metallo-β-Lactamases by a Series of Mercaptoacetic Acid Thiol Ester Derivatives", Antimicrobial Agents and Chemotherapy, Jan. 1997, vol. 41(1), pp. 135-140.

Peterson, Q.P., et al., "PAC-1 Activates Procaspase-3 in Vitro Through Relief of Zinc-Mediated Inhibition", J. Mol. Biol., Apr. 24, 2009, vol. 388(1), pp. 144-158, doi:10.1016/j.jmb.2009.03.003, Epub Mar. 10, 2009.

Putt, K.S., et al., "Small-Molecule Activation of Procaspase-3 to Caspase-3 as a Personalized Anticancer Strategy", Nat. Chem. Biol., Oct. 2006, vol. 2(10), pp. 543-550, Epub Aug. 27, 2006 (Abstract only).

Que, E.L., et al., "Metals in Neurobiology: Probing their Chemistry and Biology with Molecular Imaging", Chem. Rev., May 2008, vol. 108(5), pp. 1517-1549, doi:10.1021/cr078203u, Epub Apr. 22, 2008. (Abstract only).

Sauvage, E., et al., "The Penicillin-Binding Proteins: Structure and Role in Peptidoglycan Biosynthesis", FEMS Microbiology Reviews, Mar. 1, 2008, vol. 32(2), pp. 234-258.

Smith, R.M., et al., "NIST Critically Selected Stability Constants of Metal Complexes", Version 2.0, 1995, U.S. Department of Commerce: Gaithersburg, MD. (Abstract only).

Theuretzabacher, U., "Resistance Drives Antibacterial Drug Development", Curr. Opin. Pharmacol., Oct. 2011, vol. 11(5), pp. 433-438, doi:10.1016/j.coph.2011.07.008, Epub Aug. 19, 2011. (Abstract only).

Walsh, T.R., "Emerging Carbapenemases: A Global Perspective", Int. J. Antimicrob. Agents, Nov. 2010,vol. 36, Suppl 3, pp. S8-S14, doi:10.1016/S0924-8579(10)70004-2. (Abstract only).

Walsh, T.R., et al., "Dissemination of NDM-1 Positive Bacteria in the New Delhi Environment and its Implications for Human Health: An Environmental Point Prevalence Study", Lancet Infect. Dis., May 2011, vol. 11(5), pp. 355-362, doi:10.1016/51473-3099(11)70059-7, Epub Apr. 7, 2011. (Abstract only).

Weide, T., et al., "NH-1,2,3-Triazole-based Inhibitors of the VIM-2 Metallo-β-Lactamase: Synthesis and Structure-Activity Studies", ACS Med. Chem. Lett., Jul. 8, 2010, vol. 1(4), pp. 150-154.

Xu, Z., et al, "Zn2+-Triggered Amide Tautomerization Produces a Highly Zn2+-Selective, Cell-Permeable, and Ratiometric Fluorescent Sensor", J. Am. Chem. Soc., Jan. 20, 2010, vol. 132(2), pp. 601-610, doi:10.1021/ja907334j. (Abstract only).

Zhang, L., et al., "A Selective and Sensitive Fluorescence Probe for Imaging Endogenous Zinc in Living Cells", Tetrahedron, Jan. 7, 2013, vol. 69(1), pp. 15-21.

Russian Office Action, for Russian Application No. 2016116956/04(026639), pp. 1-6.

Russian Search Report, for Russian Application No. 2016116956/04(026639), pp. 1-3.

Kobayashi, T., et al., "DNA Degradation by the Copper (II) Complex with Tripodal-Ligands Containing Peptide Group", Polyhedron, 1998, vol. 17(9), pp. 1553-1559.

Marlin, D.S., et al., "Complexation-Induced Translational Isomerism: Shuttling Through Stepwise Competitive Binding", Angrew. Chem. Int. Ed., 2006, vol. 45, pp. 77-83, doi:10.1008/anie.200501761.

Niklas, N., et al., "Dipicolylglycyl-Phenylalanine Zinc(II): A Metallopeptide with a Built-In Conformational Switch and it's Homochiral Helical Coordination Polymer", Chem. Commun., 2003, pp. 1586-1587, doi:10.1038/b303172a.

Japanese Office Action, date unknown, for Japanese counterpart application No. 2016-519979, pp. 1-5.

* cited by examiner

OAA2172

OAA4033

INHIBITORS OF METALLO-BETA-LACTAMASE (MBL) COMPRISING A ZINC CHELATING MOIETY

CROSS-REFERENCE

This application is a section 371 national phase application based PCT/GB2014/053009, filed Oct. 6, 2014, which claims priority to Great Britain Patent Appl. No. 1317619.3, filed Oct. 4, 2013, which are incorporated by reference in its entirety.

FIELD

The present invention relates to inhibitors of metallo-β-lactamase (MBL) comprising a zinc chelating compound, and their use to improve the effectiveness of a β-lactam antibiotic against resistant bacteria producing an MBL. The inhibitors comprise a zinc chelating agent covalently bound to a molecular moiety having affinity to structures in the bacterial biology, and may be used in combination with a β-lactam antibiotic for the therapy of bacterial infection in a host organism. The host organism may be any living organism having an undesired invasion or infection by a target organism. The host organism may thus be any living organism, although preferably it will be one comprising eukaryotic cells, more preferably a warm-blooded animal, e.g. a mammal. The target organism may be any procaryotic organism, preferably a bacterium.

BACKGROUND

Infectious diseases are a leading cause of death worldwide and account for more than 13 million deaths annually including nearly two-thirds of all childhood mortality at less than 5 years of age. There is serious concern regarding new and re-emerging infectious diseases, in which effective therapies are lacking (World Health Organization reports 1999, 2012 and 2014). Antimicrobial resistance is escalating and affects a very broad range of human diseases including tuberculosis, cholera, malaria, and AIDS. Of particular concern is the number of human pathogens developing multidrug resistance to conventional antibiotics and it is estimated that the burden of resistance will surpass that of e.g. cervical cancer (de Kraker M E A. et al, *PLoS Med.* 2011; e1001104). The introduction of new, more potent derivatives of existing antibiotics provides only temporary solutions, since existing resistance mechanisms rapidly adapt to accommodate the new derivatives (Theuretzbacher U. *Curr. Opin. Pharmacol.* 2011: 11:433-438). Although resistant Gram-positive bacteria pose a significant threat, the emergence of multidrug resistant (MDR) strains of common Gram-negative pathogens such as *Escherichia coli* are of special concern. Pan-resistance or extreme drug resistance are now commonly used terms to describe clinically important isolates of *Pseudomonas aeruginosa, Acinetobacter baumannii* and Enterobacteriaceae that are resistant to virtually all antibiotics (Patel et al, *Front. Microbiol.* 2013:4:48). Unfortunately there are few, if any, antimicrobial agents effective against Gram-negative bacteria either in or entering phase 1 clinical trials that will address this critical need (Butler M S. et al, *J. Antibiotics* 2013:66:571-591).

Probably the most important antibiotic resistance mechanisms in terms of distribution and clinical relevance are β-lactamases (Bush K. et al, *Annu. Rev. Microbiol.* 2011: 65:455-478). β-lactamases are enzymes that hydrolyse β-lactam antibiotics compromising the efficacies of β-lactams our largest group and mainstay of antimicrobial chemotherapy for >70 years. Clearly, there is a need for inhibitors directed against these classes of enzymes that will restore the activity of their substrates—antibiotics that are cheap, non-toxic and normally effective. Serine β-lactamase inhibitors (clavulanic acid, sulbactam and tazobactam) have been a phenomenal success in extending the therapeutic life of β-lactam antibiotics and are also employed as diagnostic tools in clinical microbiological laboratories worldwide. In contrast, there is no clinical inhibitor available for metallo-β-lactamases (MBLs; Drawz et al., *Antimicrob. Agents Chemother.* 2014:58:1835-1846). The latter has now become one of the most clinically important families of β-lactamases showing global dissemination.

MBLs belong to a large group of proteins only found in bacteria, and like penicillin-binding proteins (PBPs) have the ability to interact with β-lactams. Examples of PBPs and enzymes that bind β-lactams are MBLs, serine β-lactamase-like protein (LACTB), D,D-transferase, D-Ala(D,D)-carboxypeptidase, the D-Alanyl-D-alanine Dipeptidases VanA, VanX, VanY and others, as reviewed by Sauvage E. et al in *FEMS Microbiol Rev* 32 (2008): 234-258. This class of proteins is only found in bacterial biology. Examples of compounds having affinity for PBPs are β-lactam antibiotics. β-Lactams have been the historical anchor of antibacterial chemotherapy and include penicillins, cephalosporins, monobactams and carbapenems (Bush K. et al, *Annu. Rev. Microbiol.* 2011: 65:455-478). The mechanism of action for the β-lactam antibiotics is that they mimic the small dipeptide D-Ala-D-Ala that the bacteria use to crosslink peptidoglycans in the bacterial wall, covalently destroying enzymes that use D-Ala-D-Ala as their substrate. β-lactamases are the most prevalent and clinically important resistance mechanism inactivating β-lactams by hydrolysis. They are classified according to sequence criteria (Ambler class A, B, C and D) and can be structurally grouped into two super families; the serine β-lactamases (class A, C, and D) and MBLs (class B). In contrast to the serine β-lactamases, which are characterized by a serine moiety in the active site, MBLs require divalent cations, usually zinc, as a metal co-factor of enzyme activity (Palzkill T. *Ann. N.Y. Acad. Sci.* 2013:91-404). MBLs are emerging as one of the most clinically important family of β-lactamases (Patel et al, *Front. Microbiol.* 2013: 4:48; Walsh et al, *Int. J. Antimicrob. Agents* 2010:S8-S14) for the following reasons:

(i) Acquired MBL genes are associated with mobile genetic elements that often carry other resistance genes as gene clusters (associated with IS and ISCR elements) and/or integron arrays resulting in multi-drug resistant isolates. In many parts of the world such elements are now commonly observed in clinical important pathogens such as *P. aeruginosa, A. baumannii*, and several Enterobacteriaceae geni. Thus, the plasticity and dissemination of these highly mobile resistance gene clusters severely compromises existing therapeutic regimes.

(ii) The hydrolytic spectrum of MBLs is one of the broadest of all β-lactamases and includes nearly all β-lactams except the monobactams (aztreonam). Accordingly, clinical isolates possessing MBLs are invariably resistant to all β-lactam antibiotics except for the monobactams. However, virtually all MBL positive bacteria carry additional β-lactamases that can hydrolyze aztreonam and therefore this therapy is not recommended.

The clinically most important MBLs, the IMP-, VIM- and NDM-groups, are now widespread in a variety of Gram-negative species. In particular, VIM- and NDM-enzymes have emerged as the dominant MBLs. The unprecedented global dissemination of NDM highlights the enormity of the problem. Since the first report in 2008, NDM has been identified in Australia, Africa, North-America, Asia and many European countries (Johnson A P. et al, *J. Med. Microbiol.* 2013:62:499-513). Worryingly, NDM is found in numerous Gram-negative species and in the environment (Walsh T R. et al, *Lancet Infect. Dis.* 2011: 11:355-362).

Successful inhibitors of class A serine β-lactamases are clinically available, but lack inhibitory activity against MBLs (Drawz S M. et al, *Clin. Microbiol. Rev.* 2010:23: 160-201). Inspired by the commercial success of the paradigm Augmentin (clavulanic acid—a suicide substrate for serine β-lactamases—and amoxicillin) several research groups have focused on similar approaches to develop inhibitors, but yet no molecules that combine potency with activity against multiple MBL targets have reached clinical trials (Drawz S M. et al. *Antimicrob. Agents Chemother.* 2014). For the three clinically most threatening MBLs—the IMP, NDM and VIM groups—most inhibitors are reported for IMP-1, while few inhibitors are found for VIM-2 and NDM. For NDM, a fungal natural product, aspergillomarasmine A has been identified as an MBL inhibitor and shown in vivo activity in mouse models (King A M. et al. *Nature* 2014:510:503-506). However, relatively high doses of aspergillomarasmine A are required to reverse carbapenem resistance. Other therapeutic options (Martinez, *Future Med. Chem.* 2012) include the use of tri-β-lactam therapy incorporating a monobactam; however, the MICs are not impressive and their in vivo activity is severely compromised by the bacterial inoculum (Page et al., *Antimicrob. Agents Chemother* 2011).

Thus, there is a strong clinical need for an MBL inhibitor. The majority of potent inhibitors of IMP-1 contain a thiolcarboxylate or a dicarboxylate pharmacophore, while among VIM-2 inhibitors the thiocarboxylates are the most dominant. The only inhibitors, which target IMP-1 and VIM-2 simultaneously, are found among these structural motifs. However, the recently characterized maleic acid derivatives lack broad spectrum inhibition i.e. show poor inhibition against the clinically important VIM and NDM-group enzymes. Nevertheless, some structurally very different inhibitors selectively targeting VIM-2 in favour of IMP-1 have been reported (Weide et al, *Med. Chem. Lett.* 2010). Few studies have evaluated the inhibitor efficiency in extensive whole cell assays and, even less so, in vivo efficacy in animal models. The majority of inhibitors heavily rely on monodentate zinc-binding groups like a thiol or a carboxylate group complexing the enzymatically bound zinc ions. Interestingly, typical bidentate zinc-binding groups successfully applied in the design of inhibitors of other zinc-containing metalloproteins like hydroxamates are—with one exception—not reported. Comparison of the available structures reveals that all inhibitors substitute the bridging hydroxide in dinuclear zinc MBLs by a heteroatom e.g. S or O.

Clinically important bacteria are well known in the prior art—see e.g. Wikipedia. Especially, *P. aeruginosa* causes serious problem because of its conspicuous multidrug resistance. So called scavengers, e.g. sulbactam, clavulanic acid, and tazobactam which are used as β-lactamase inhibitors in general are effective against serine-β-lactamase having serine as an active centre, but these drugs exhibit less or no inhibiting effect on MBLs. Therefore, the need for new MBL inhibitors becomes increasingly important. Important β-lactam antibiotics are the penicillin, cephlosporin and carbapenem classes. Many compounds have been reported as having MBL inhibiting activities. In WO 98/117639, WO 97/30027, WO 98/40056, WO 98/39311, and WO 97/110225, a class of β-thiopropionyl-amino acid derivatives has been described as the inhibitors against the MBLs. Other compound classes that may act as MBL inhibitors are thioesters (Biol. Pharm. Bull. 1997, 20, 1136; FEMS Microbiology Letters 1997, 157, 171; Antimicrob. Agents Chemother. 1997, 41, 135; Chem. Commun. 1998, 1609; Biochem. 1.1998, 331, 703; WO 00/076962) and succinic acid derivatives (WO 01/030148 and WO 01/030149).

The use of metal chelators against virus or bacteria has been well described in the prior art, e.g. in WO 2011/63394, WO 2004/71425, WO 2006/109069, WO 2001/60349, U.S. Pat. No. 6,410,570, US 2003/0225155, WO 2006/43153 and WO 2006/43153. The person skilled in the art will appreciate the variety of substances described in prior art, capable of chelating metal ions, and will select an appropriate chelator for different purposes. Examples are chelators comprising variations of amino groups and hydroxyl groups, e.g. 1,10-phenanthroline, clioquinol, 1,2-dimethyl-3-hydroxy-4-pyridinone (DMHP), 1,2-diethyl-3-hydroxy-4-pyridinone (DEHP), deferasirox, chelators comprising variations of amino groups, hydroxyl groups and carboxylic acid groups, e.g. ethylenediaminetetra-acetic acid (EDTA), ethylenediamine-N,N'-diacetic-N,N'-di-B-propionic acid (EDPA), diethylenetriamine pentaacetic acid (DTPA), trans-1,2-cyclohexane-diamine-N,N,N',N'-tetraacetic acid (CyDTA), carnosine, dihydroxyethylglycine (DHEG),1,3-diamino-2-hydroxypropane-N,N,N',N'-tetraacetic (DTPA-OH), ethylenediamine-N,N'-diacetic acid (EDDA), ethylenediamine-N,N'-dipropionic acid (EDDP), N-hydroxyethylenediamine-N,N',N'-triacetic acid (EDTA-OH), N,N'-bis(2-hydroxybenzyl)ethylenediamine-N,N'-diacetic acid (HBED), hexamethylene-1,6-diaminetetraacetic acid (HDTA), hydroxyethyliminodiacetic acid (HIDA), iminodiacetic acid (IDA), Methyl-EDTA, nitrilotriacetic acid (NTA), nitrilotripropionic acid (NTP), triethylenetetraaminehexaacetic acid (TTHA), ethylenediamine-di(O-hydroxyphenylacetic acid) (EDDHA), ethyleneglycol bis(2-aminoethyl ether)-N,N,N',N'-tetraacetic acid (EGTA), trans-1,2-cyclohexanediaminetetraacetic acid (CDTA), N-(2-hydroxyethyl) ethylenedinitrilotriacetic acid (HEDTA), N-(2-hydroxyethyl) iminodiacetic acid (HEIDA), citric acid, 7,19,30-trioxa-1,4,10,13,16,22,27,33-octaazabicyclo[11,11,11] pentatriacontane (O-Bistren), penicillamine, chelators also comprising sulfur or phosphorus, e.g. diethyldithiocarbamate(DEDTC), 2,3-dimercapto-1-propanesulfonic acid (DMPS), ethylmaltol (EM), 4-(6-Methoxy-8-quinaldinylaminosulfonyl)benzoic acid potassium salt (TFLZn), dithiozone, N-(6-methoxy-8-quinolyl)-para-toluenesulfonamide (TSQ), ethylenediamine-N,N'-bis(methylphosphonic) acid (EDDPO), ethylenediaminetetra(methylenephosphonic) acid (EDTPO), nitrilotrimethylenphosphonic acid (NTPO), dimercaptosuccinic acid (DMSA), deferoxamine, dimercaprol, dimercaptosuccinic acid, and etidronic acid. However, these chelators are known in the prior art, e.g. in Smith, R. M.; Martell, A. E. *NIST Critically Selected Stability Constants of Metal Complexes, Version* 2.0; U.S. Department of Commerce: Gaithersburg, Md., 1995, as non-selective chelating agents with relatively low ability to discriminate between different metal ions. Thus, they may simultaneously have the ability to bind essential metal ions like zinc, iron, copper, nickel, cobalt, manganese and other metal ions essential in most enzymes in nature, e.g. in bacteria and mammals. This lack of selectivity may lead to undesired toxicity and other biological effects when treating specific infections by a target organism in a host organism, e.g. when it is desirable to affect only specific microorganisms whilst the toxicological effect on the host organism or other species which are not a target for the treatment is low.

A key element necessary for normal life of a bacterial cell is the homeostasis of zinc. Zinc is the second most abundant transition metal in the human body and is responsible for the catalytic function and structural stability of over 6000 enzymes and proteins (Bertini, et al, Journal of Inorganic Biochemistry 111 (2012) 150-156). Manipulation of the freely available zinc in a cell has been shown to affect a great range of diseases and conditions (Que et al, *J. Chem. Rev.* (Washington, D.C., U. S.) 2008, 108, 1517-1549; Peterson, et al *Mol. Biol.* 2009, 388, 144-158; BarKalifa et al, *Eur. J. Pharmacol.* 2009, 618, 15-2; Maret et al, *Mol. Med.* 2007, 13, 371-375). The concentration of free zinc varies in biological tissues depending on zinc buffering capacity. In PC12, HeLa, and HT-29 cell lines, as well as in primary cultures of cardiac myocytes and neurons in vitro, the concentration of free zinc has been determined to be approximately 5 nM (Bozym et al, *Exp. Biol. Med.* 2010, 235, 741-750). Zinc is a soft metal, mainly found in the nature as salpherite or zinc sulfite, with Zn oxidation state+2 (Emsley, J. "*Zinc". Nature's Building Blocks: An A-Z Guide to the Elements*; Oxford University Press: New York, 2001). In order to chelate zinc selectively and with high efficacy, the use of soft basic ligands are needed. The lipophilic zinc chelator, N,N,N',N'-tetrakis(2-pyridylmethyl) ethylenediamine (TPEN), has been reported to display many interesting biological activities due to its zinc chelating properties as well as its lipophilic character, allowing cell-membrane penetrating abilities (Donadelli et al, *J. Cell. Biochem.* 2008: 104, 202-212). In the TPEN molecule, the zinc-binding ability is based on the binding of two or more units of the picoylamine unit (see Scheme 1).

Scheme 1

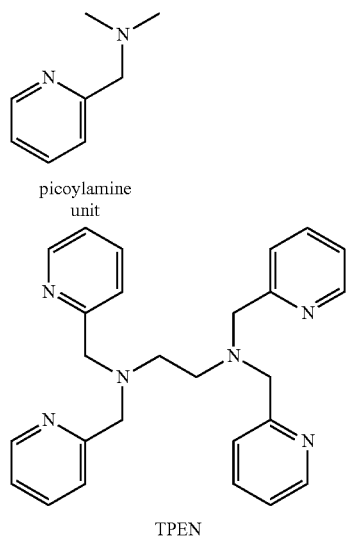

picoylamine unit

TPEN

Other technologies employ sulfur based ligands, also yielding high selectivity for zinc compared to other endogenous metal ions (Zhang et al, *Tetrahedron* 2013, 69, 15-21). Zinc sensing in bacteria is carried out by regulators of different families, including SmtB/ArsR, MerR, TetR, MarR, and the Fur family (Napolitano et al, Journal of Bacteriology 2012, p. 2426-2436). X-ray structures of MBLs indicate a tightly bound zinc ion at the active site, and often the structures reveal two Zn atoms at the catalytic site, one tight and one more loosely bound (Palzkill T. *Ann. N.Y. Acad. Sci.* 2013:91-404). Subclass B1 is the largest MBL family, including the majority of enzymes such as the IMPs, VIMs and NDMs. The B1 enzymes feature a conserved Zn(II) binding motif and there are two Zn2+ at the active site of B1 enzymes, with Zn1 bound by three His residues and Zn2 by one His, one Cys and one Asp. In addition, there is a bridging water or hydroxide ligand between the two Zn ions, which is believed to be the nucleophile that hydrolyses the substrate, e.g. the β-lactam antibiotic. The zinc ions are essential for the activity of the enzymes. In some embodiments the MBL inhibitors contain a Zn(II) binding group that can interact with the central metal ion(s) strongly. In the prior art, zinc chelators have been described as inhibitors of multiple diseases simultaneously, e.g. in WO 2006/117660, WO 2001/60349 or U.S. Pat. No. 6,410,570). Zinc chelators have also been suggested as antibacterial agents, e.g. in WO 2009/140215, as inhibitors of biofilm formation, e.g. in WO 2011/63394 and WO 2009/155088, or as antiviral agents, e.g. in WO 2004/71425 and WO 2006/43153. Attractive bacterial zinc-dependent targets involved in resistance mechanisms are known in the prior art to be inhibited by zinc chelating agents. Three examples are the tightly regulated bacterial zinc uptake system Zur (Ellison et al in PLOS ONE 8 (2013), e75389), biofilms (Conrady et al, PNAS (2008) 105 (49), 19456-19461) and the peptidase HmrA in MRSA. All these targets are inhibited by state of the art zinc chelators like TPEN, EDTA or the phenanthrolines. However, these agents do not possess specific affinity for bacterial biology, and are also toxic to mammals. Another example of vital zinc-dependent machineries is bacterial use of the efflux pumps (Nikaido, et al, FEMS Microbiology Reviews 36 (2012) 340-363), adapting almost all modern antibiotics as substrates, excreting them from the bacterial cell. Yet another example is the zinc-dependent deacetylase LpxC (Liang et al, J. Med. Chem. 2013, 56, 6954-6966). Another example is the highly zinc-dependent bacterial ribosomal function (Graham et el, *J. Biol. Chem.* 284 (2009) pp. 18377-18389). The latter uses 8 zinc atoms on the 70S ribosomal unit.

However, in these descriptions, there is no guidance on how to obtain selective effects of the zinc chelation therapy in the target species whilst a host organism is affected at a low enough level to avoid issues related to, for example, toxicity. Thus there is a medical need for zinc chelating agents with a low toxicity in a host organism, whilst also having a selective effect on the target organism.

SUMMARY

The invention provides compounds according to formula I:

A-L-B wherein A represents a lipophilic chelating moiety which is selective for $Zn^{2+}$ ions; L is a covalent bond or a linker; and B is a vector which is either a moiety capable of interacting with one or more biological structures found in a bacterium (preferably in a bacterial cell wall), for example a penicillin-binding protein such as a metallo-β-lactamase or DD-transferase, or a moiety capable of enhancing transport of the compound across a bacterial cell membrane. Such compounds find use in a method of treating and/or preventing a bacterial infection in a human or non-human mammal. In such a method, the compound of formula I may be administered in combination with (either simultaneously, separately, or sequentially) a β-lactam antibiotic.

DETAILED DESCRIPTION

Figure 1:
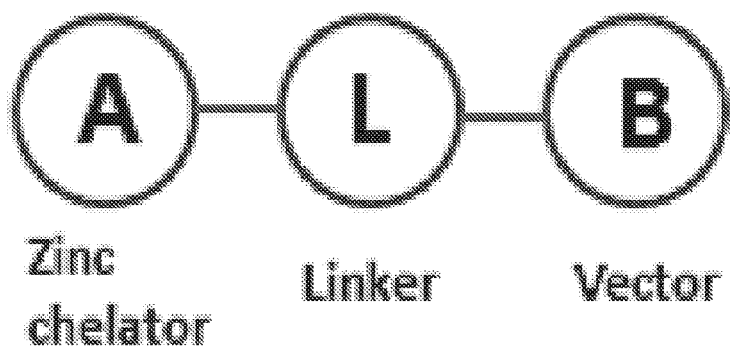
FIG. 1 illustrates the lead candidate inhibitors of the disclosure.

It has now been surprisingly found that in a synthesized library of novel compounds, lead candidate inhibitors affect resistant bacterial strains harboring MBLs. The lead compounds show $EC_{50}$ values in the nanomolar range against some of the most clinically relevant bacterial strains, harboring some of the most important MBLs. The lead candidates contain three central structural elements (see also FIG. 1) in a construct not previously described in the prior art:

A-L-B wherein A is zinc chelator, L is a linker, and B is a vector. Moiety A is any lipophilic, selective Zn(II) chelating group. The term "chelating" relates to the greek term "chelos" denoting a crab claw binding an object via at least two contact points. Thus, a chelating agent in chemistry may be defined as a molecular moiety:

(II)

where m is an integer from 2 to 10;
each group C is a functional group that may be the same or different having Lewis base properties and possessing at least one heteroatom selected from N, S, O or P capable of donating electrons to a Lewis acid, M, which in the present invention is a zinc atom; $R_c$ is a unit linking the groups C which may contain up to 50 atoms, and which carries a functional group $R_L$; and
$R_L$ comprises a covalent link to the linker L in the construct A-L-B herein defined.

Moiety L is a linker or bond that covalently links A and B. The linker L may optionally have ligand groups supporting Zn(II) chelating groups.

Moiety B may be a group interacting with biological structures found in bacteria, e.g. this may be specific to MBLs, DD-transferases, or other enzymes not found in human biology and thereby having less toxicity to humans, or it may facilitate transport over bacterial membranes.

More specifically, B may be a chemical moiety having affinity for biological structures found in prokaryotic cells like bacteria, or in virus or parasites. At the same time, moiety B has a sufficiently low affinity for biological structures found in organisms comprising eukaryotic cells, e.g. in mammals, especially higher mammals like humans so as not to induce undesired effects like signs of toxicity.

Thus, in one embodiment the moiety B may be a molecular moiety found in bacteria but not in the host organism. Non-limiting examples of such moieties are peptidoglycans only found in bacteria. These comprise linear chains of two alternating amino sugars, N-acetyl-glucosamine (GlcNAc) and N-acetylmuramic acid (MurNAc). Each MurNAc is attached to a short (4- to 5-residue) amino acid chain. These amino acid chains consist of building blocks not found in mammalian biology, often with the R configuration of the amino acid functionality, corresponding to the D configuration in molecules comprising an α-amino acid functionality. The following non-limiting list of building blocks may be present in moiety B as used in the present invention: L-lysine, L-alanine, D- or L-glutamic acid, D-glutamine, meso-diaminopimelic acid, D-2,3-diamino propanoic acid, D-alanine or other amino acids with the D-configuration, and any derivatives thereof (e.g. ester derivatives). D-amino acids do not occur in proteins and are not found in eucaryotic organisms. Thus, in one embodiment, moiety B may be a construct comprising any combination of the building blocks listed above or molecules mimicking such a construct. One example of a compound mimicking a tripeptide comprising amino acids with the D-configuration is aspergillomarasmine, which is described in the prior art, e.g. by Mikami et al, Agricultural and Biological Chemistry (1983), 47(11): 2693-5. Preferred are combinations of amino acids with the D-configurations, e.g. combinations of D-glutamic acid, D-glutamine, meso-diaminopimelic acid and D-alanine. Other combinations of amino acids which may be used are combinations of D-alanine, for example the building block D-Alanine-D-Alanine itself or a derivative thereof such as glycyl-L-α-amino-ε-pimelyl-D-Alanine-D-Alanine. In any of these constructs, the carboxylic acid moiety in the amino acid building blocks may be substituted by isoelectronic functional groups like boronic acid, $-B(OH)_2$, phosphoric acid, $-P(=O)(OH)_2$, or sulfonic acid, $-SO_3H$. The carboxylic acid or any of these isoelectronic functional groups may also be esterified. Moiety B may also be a substrate for any of the enzymes which use constructs of these building blocks as a substrate in the process of building the bacterial wall or membrane, e.g. D,D-transferase which uses D-Ala-D-Ala.

In another embodiment, moiety B may comprise a β-lactam structural unit having an affinity for a large group of proteins only found in bacteria, denoted penicillin-binding proteins (PBP). Examples of PBPs are MBLs, serine beta-lactamase-like protein (LACTB), D,D-transferase, D-Ala(D,D)-carboxypeptidase, the D-Alanyl-D-alanine Dipeptidases VanA, VanX, VanY and others, as reviewed by Sauvage et al in FEMS Microbiol Rev 32 (2008) 234-258. Other members of this protein class may facilitate transport over bacterial membranes. This class of proteins is only found in bacterial biology, not in mammalian biology, and is a suitable class of targets for the molecular moiety B in the constructs according to the present invention. Examples of compounds having an affinity for PBPs are β-lactam antibiotics. Thus, derivatives of penicillins, cephalosporins, carbapenems and monobactams are examples of molecular moieties which may be used as moiety B in the invention. These classes represent large classes of antibiotic agents on the market, and many building blocks in their synthetic process are commercially available for use in the construct A-L-B in the present invention.

As stated above, an example of a DD-transferase substrate, useful as a moiety B unit is D-Ala-D-Ala, which is used as a building block for bacterial wall synthesis. Antibacterial agents are molecules that have a selective interaction with biological structures found in bacteria, and not in human biology; for example, penicillins mimic D-Ala-D-Ala and thus act as an antagonist for DD-transferase. Further, β-lactam antibiotics are substrates for MBLs. Thus, moiety B may be any substrate for bacterial biological structures. Non-limiting examples of moiety B include: penicillins, cephalosporins, carbapenems, clavulanic acid, sulbactam, tazobactam, monobactams (e.g. aztreonam), thiopropionyl-amino acid derivatives, thioesters, succinic acid derivatives and maleic acid derivatives.

The zinc-binding unit A comprises at least one lipophilic metal chelating function with selectivity for zinc. A preferred, but non-limiting example of the molecular moiety A is the moiety comprising two 2-pyridyl-methyl units, denoted dipicoyl (see Scheme 2, A, B) with an adjacent donor atom D assisting the stabilization of the zinc-chelating dipicoyl unit (Scheme 2, A-C). The moiety A may also comprise more than two 2-pyridyl-methyl units, e.g. a novel TPEN derivative. TPEN, as defined above, has been widely used in many biological applications in the prior art. TPEN has four 2-pyridyl-methyl units, rendering the zinc chelating ability stronger. A TPEN derivative as depicted in Scheme 2D, with a covalent bond to a linker group L, is not known in the prior art and is a part of the present invention. Scheme 2E shows a further example of a suitable chelating moiety A.

Scheme 2

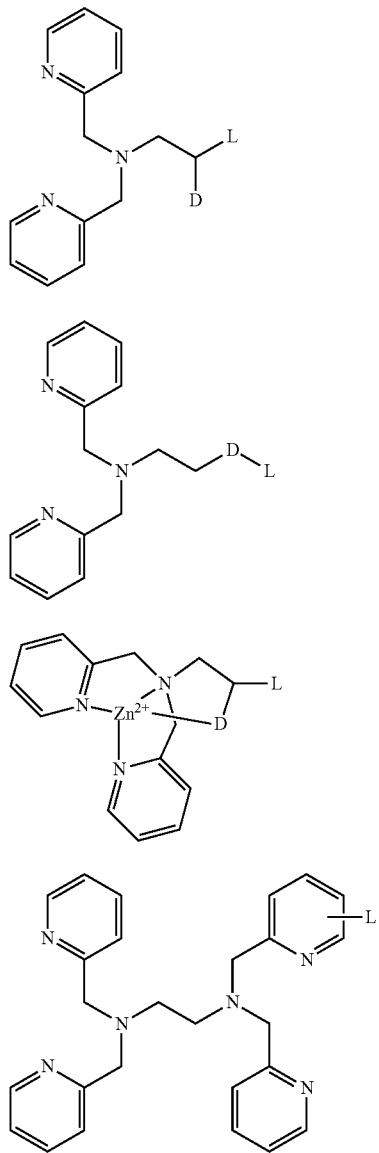

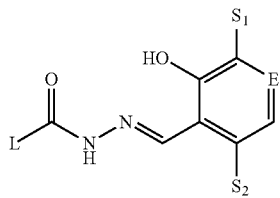

D=an electron donating atom, L=a linker as defined herein; $S_1$=H or an alkyl group, $S_2$=H, lower alkoxy or a hydroxy group; E=CH or N.

To have a strong interaction with essential zinc atoms necessary for the MBLs to function properly, the preferred zinc-chelating function needs to have as low as possible a dissociation constant $K_d$ with zinc. The dissociation constant $K_d$ is the inverse of the metal complex formation constant $K_f$, so $K_d=1/K_f$. In the present invention, the $K_d$ value in general is preferably lower than $1\times10^{-5}$ M, even more preferably lower than $1\times10^{-8}$ M, yet more preferably lower than $20\times10^{-10}$ M or lower than $1\times10^{-10}$ M. In general, the dipicoyl units in Scheme 2 A and B have $K_d$ with zinc in the range $1-10\times10^{-10}$ M (Åstrand, et al, Tetrahedron 69 (2013) 8645-8654). The lipophilic, cell-penetrating zinc chelator TPEN has a dissociation constant ($K_d$) with zinc of $0.26\times10^{-15}$ M (Makhov, et al, Cell Death Differ. 2008, 15, 1745).

The o-hydroxybenzylidene-hydrazide moiety (Scheme 2E) may also be used in the present invention, and is also reported in the prior art to have zinc-chelating properties with $K_d$ values in the range $1-30\times10^{-10}$ M (Putt, et al, Nat. Chem. Biol. 2006, 2, 543; Charkoudian, J. Am. Chem. Soc. 2006, 128, 12424; Hsu, et al, ACS Comb. Sci. 2012, 14, 44).

In Ganta, et al, Bioorganic & Medicinal Chemistry Letters 19 (2009) 1618-1622, a group of compounds have been reported, having a hydroxamate group as a zinc-chelating moiety in the same molecular moiety as a group with affinity for MBLs. However, according to Smith, R. M.; Martell, A. E. NIST Critically Selected Stability Constants of Metal Complexes, Version 2.0; U.S. Department of Commerce: Gaithersburg, Md., 1995, the hydroxamate complexing dissociation constant with zinc is reported to be in the range $10^{-4}$, which is five orders of magnitude higher than shown for the dipicoylamines. Further, the hydroxamate group is a non-selective chelating group, also demonstrating binding of $Fe^{2+}/Fe^{2+}$ and many other metal ions, making hydroxamate ligands less specific, and more prone to interaction with human biology leading to higher human toxicity. Ligands based on the 2-pyridyl-methyl units demonstrate remarkably high selectivity for zinc and cadmium (Xu, et al, J. Am. Chem. Soc. 2010, 132, 601), the latter is not a natural metal ion in biological systems. Zinc chelating agents are also suggested in the prior art to act as MBL inhibitors, in WO 2012/088283, thiazolidines and analogous compounds are suggested as MBL inhibitors together with beta lactams. The use of the di-picoylamine group in zinc chelators is not mentioned herein. However, these agents also have complexing dissociation constants with zinc which are significantly higher than the nanomolar range. Also, no $IC_{50}$ values below the micromolar range in MBL assays are found in WO 2012/088383.

Each of the Schemes 3-5 below is provided for the purpose of illustration and description of a part of the invention only, and is not intended as a definition of the limits of the present invention. Thus, members of the library of compounds synthesized so far, are exemplified, but not limited to those in Schemes 3-5.
Scheme 3
OAA2231
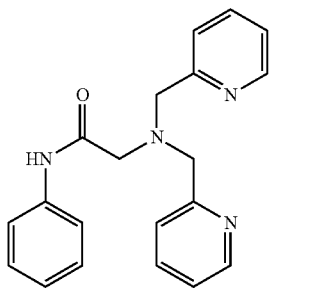
OAA2172
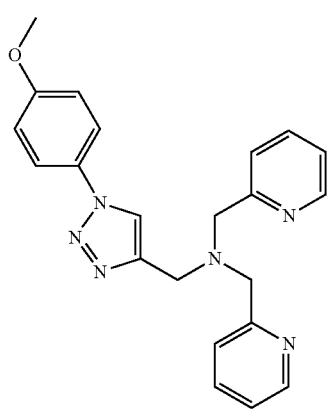
OAA2168
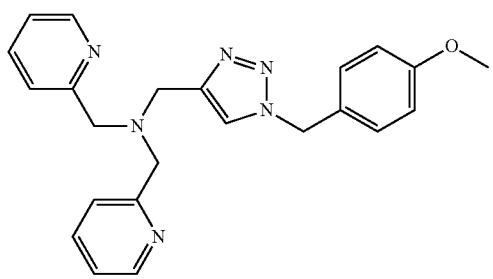
OAA2237
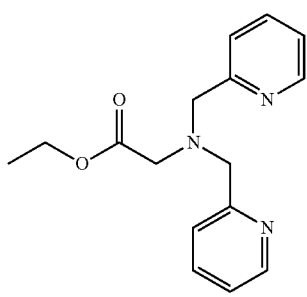
-continued
OAA2247
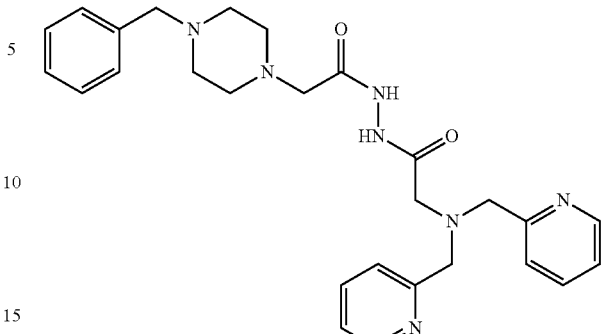
OAA4033
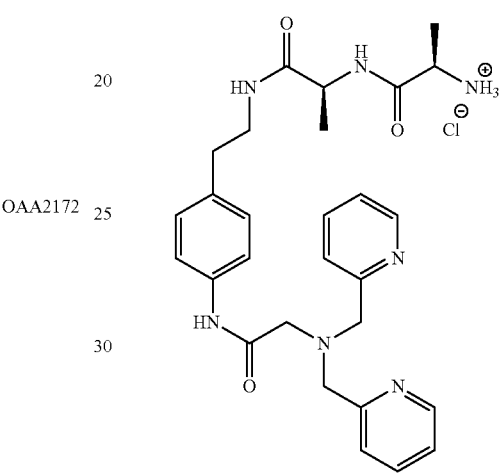
Scheme 4
OAA2241
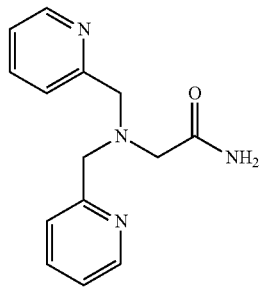
OAA3168
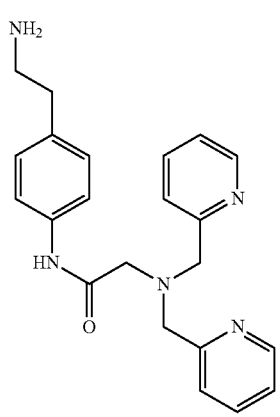

-continued
OAA2225
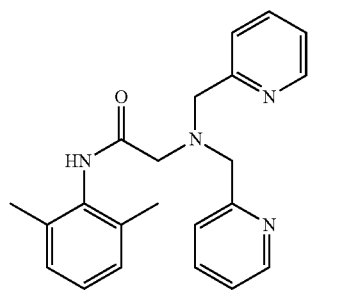
OAA3068
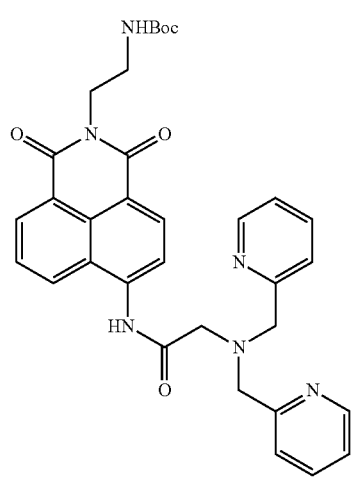
OAA2193
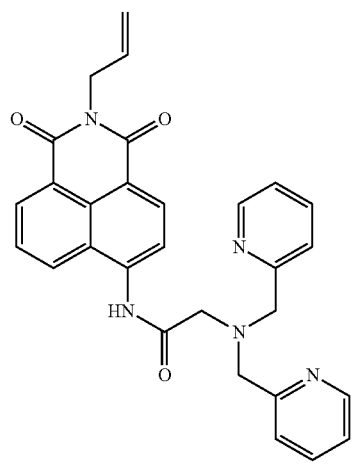
OAA3168
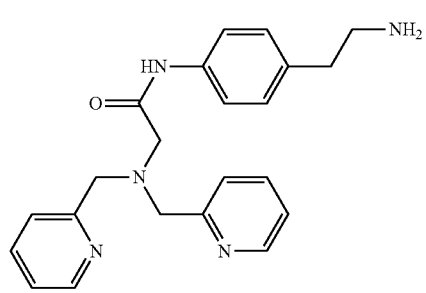
-continued
OAA2247
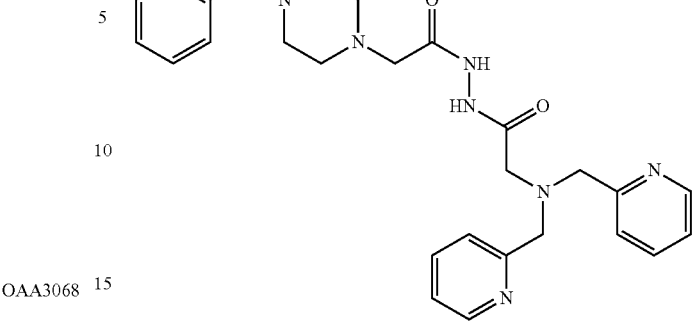
Scheme 5
OAA4063
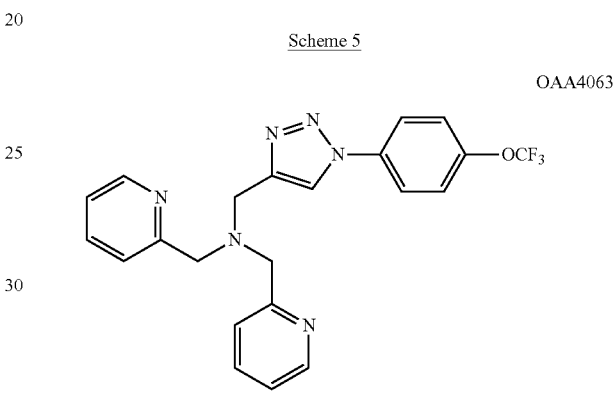
OAA2168
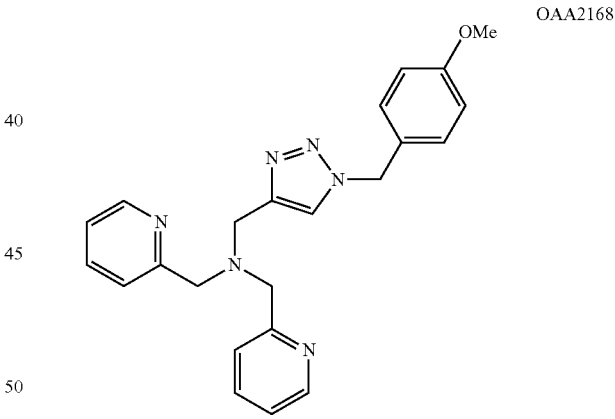
OAA4069
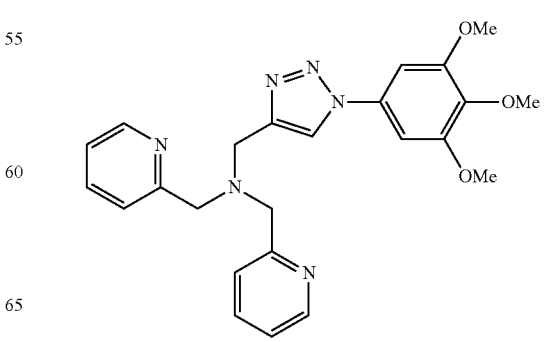

OAA4071
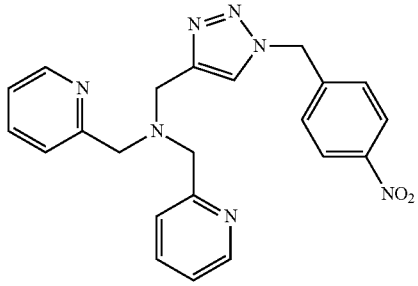
OAA4075
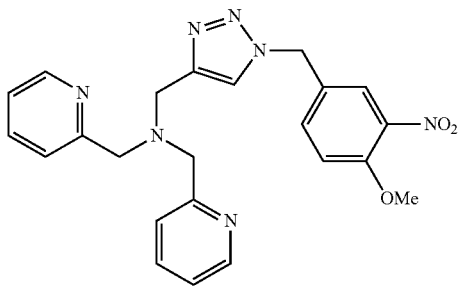
OAA4077
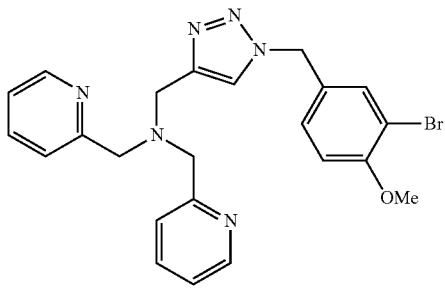
OAA4067
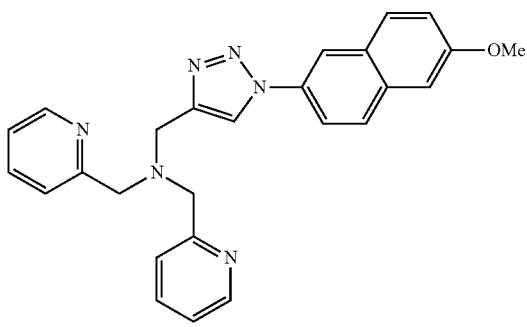
OAA4079
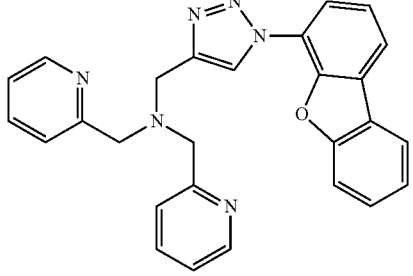
OAA4073
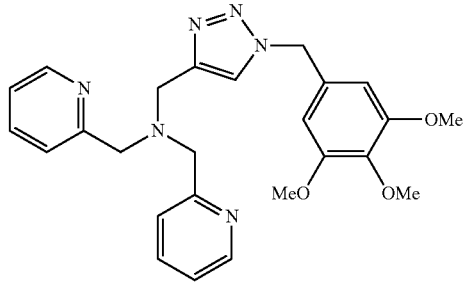
All of the exemplified molecules have a dissociation constant $K_d$ with zinc of less than $1\times10^{-10}$ M.
A general preparation process for some library members is exemplified in Scheme 6:
Scheme 6
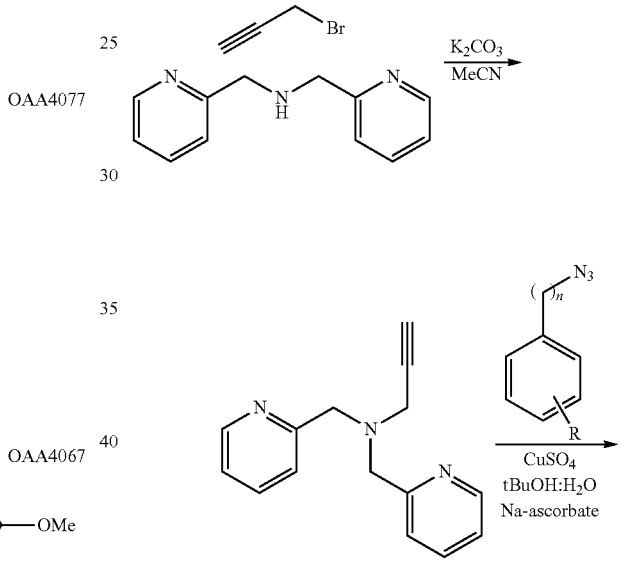
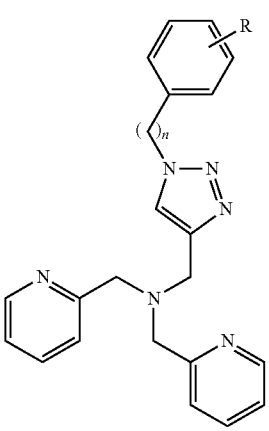
One preferred compound of the invention, OAA4033 (Example 24), was prepared as indicated in Scheme 7:

Scheme 7

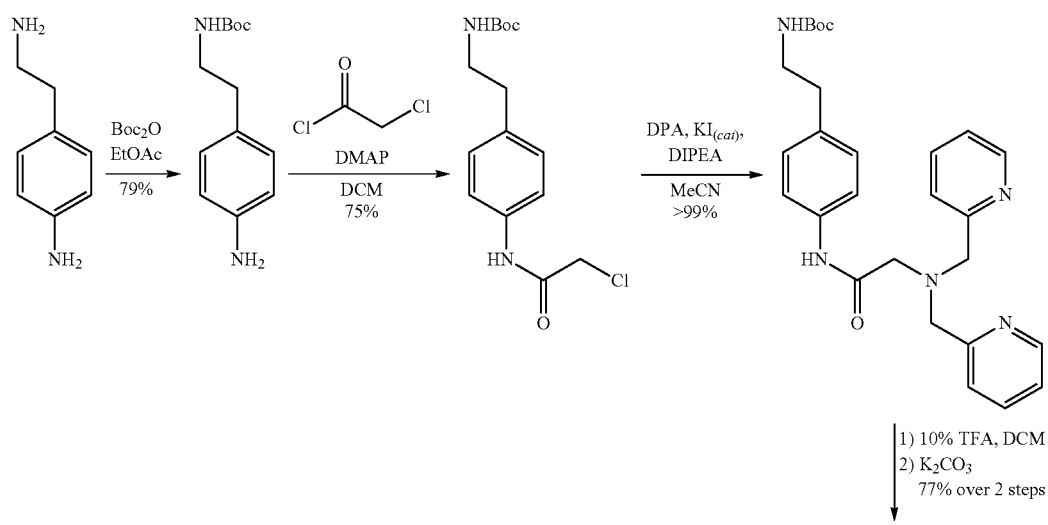

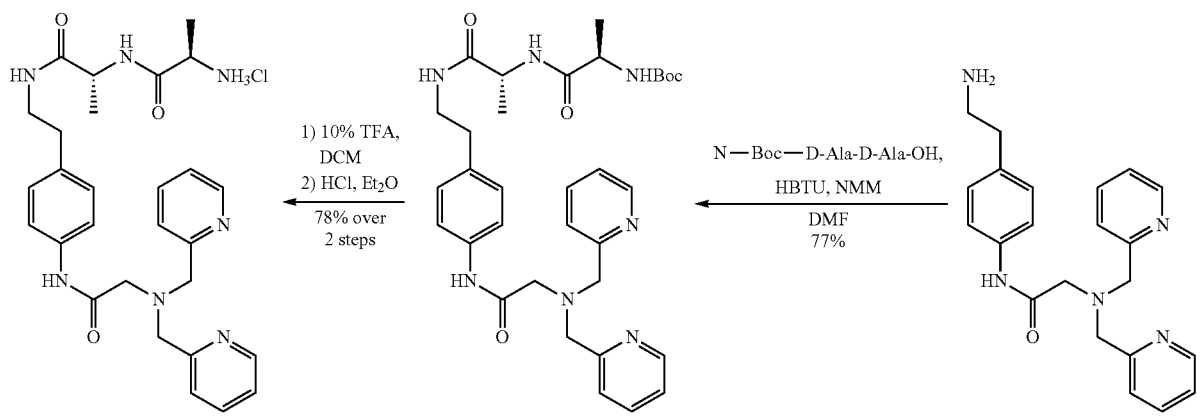

The compound OAA4033 (Example 24) is an example of the core of the present invention, schematically and generally denoted as A-L-B. The zinc chelator is a dipicoylamine moiety (A), the linker is a carbonylamino-phenyl group and the vector is a D-Ala-D-Ala peptide. Alternatively viewed, the zinc chelator may be considered as the dipicolylaminomethyl-carbonylamino moiety (A), the linker as the phenyl-ethyl group and the vector (B) as the D-Ala-D-Ala peptide.

As stated above, the mechanism of all β-lactam antibiotics is to mimic the D-Ala-D-Ala building block used by the bacterial enzyme DD-transferase in the synthesis of the bacterial cell wall. Normally, amino acids with the stereochemistry L are found in human biology. Thus, the dipeptide bacterial substrate D-Ala-D-Ala, has affinity for the bacterial enzyme DD-transferase.

Two especially preferred examples of the invention, AB773 and AB777, are prepared from the commercial compounds clavulanic acid and amoxicilline, defined as the vector B in the present invention (see Scheme 8):

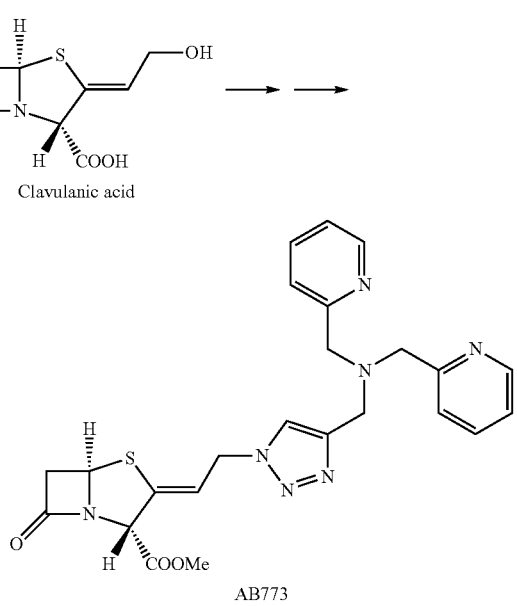

Scheme 8

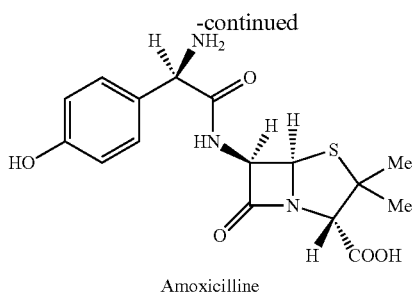
Amoxicilline

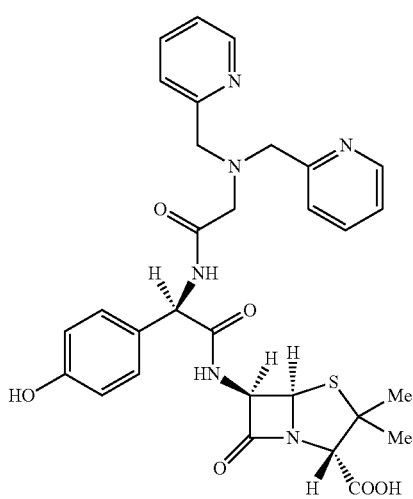
AB777

The new chemical entities, hereto untested as inhibitors of MBLs, now show promising $EC_{50}$ values, e.g. for VIM-2 compared to control inhibitors. The same inhibitors showed activity in both enzyme and bacterial whole cell assays with *E. coli* harboring VIM-2. The most active inhibitors showed even better (sub-μM) activity against other MBLs such as NDM-1 and GIM-1 and in bacterial whole cell assays with *E. coli* harboring GIM-1. The inhibitors showed promising performance in a bacterial synergy assay with the β-lactam antibiotic meropenem against different clinical *P. aeruginosa, E. coli* and *K. pneumoniae* isolates harboring different MBLs (VIM-2, VIM-1, and NDM-1) providing evidence that these have the potential to be used as a β-lactam-β-lactamase inhibitor combination therapy. Several library candidates showed synergistic activity with meropenem. We proceeded by combining the zinc-binding fragment (fragment A) with a molecular moiety with affinity to structural units found in bacterial biology but not found in human biology (fragment B). The resulting compound (OAA4033, Example 24) shows promising performance in all in vitro tests so far and performed well in the synergy assay with meropenem. These results point in the direction of a conceptually new class of antibacterial agents.

Other compounds according to the invention include the structures in Scheme 9:

Scheme 9

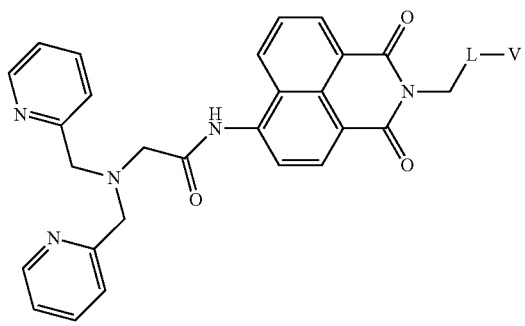
I

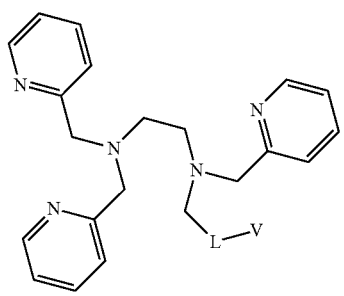
II

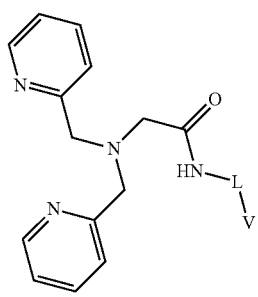
III

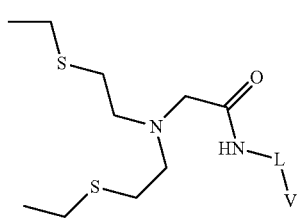
IV

-continued

V

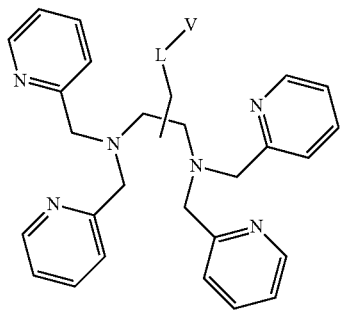

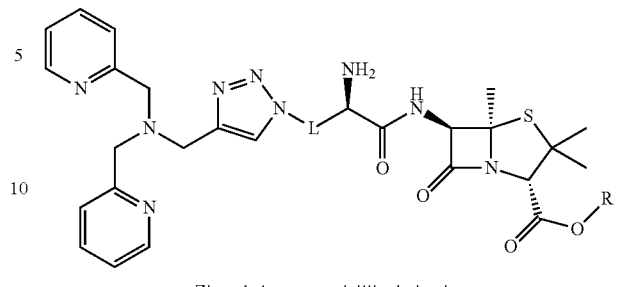

Zinc-chelator-amoxicillin derivative
R = H, or lipophilic, biodegradable like in piv-Ampicillin

VI

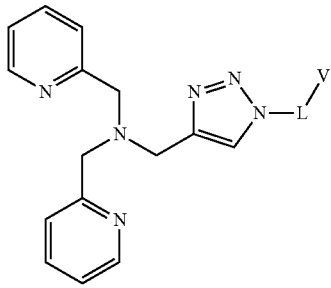

IX

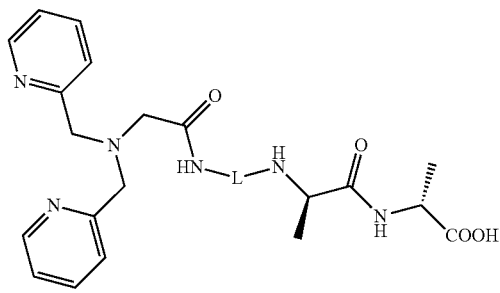

Zinc-chelator-amoxicillin derivative
with the bacterial building block ——D-Ala-D-Ala. This vector
can also be ——D-ala-D-lactic acid wherein L is a linker as herein defined and V is a vector corresponding to moiety B as herein defined.

VII

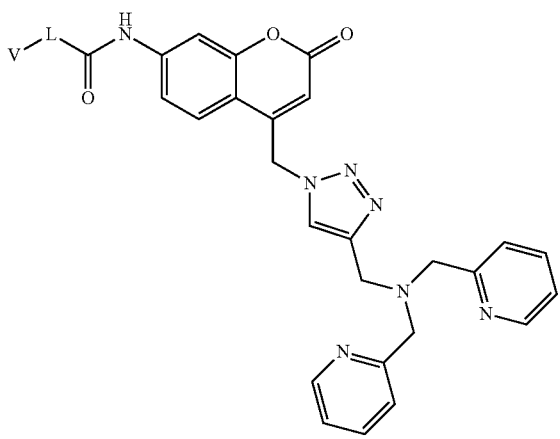

The macrolides are a group of antibiotics whose activity stems from the presence of a macrolide ring. They inhibit bacterial protein biosynthesis through binding to the bacterial ribosome and inhibit ribosomal transfer of tRNA as well as inhibiting ribosomal translocation. As noted above, the bacterial ribosome is an example of a highly zinc-dependent bacterial protein. Macrolide chemistry is well described in the prior art, e.g. by Liu et al in Bioorganic & Medicinal Chemistry Letters 19 (2009) 4079-4083. Macrolides and their derivatives are thus a further example of the vector B which may be present in the constructs herein described. For example, the carbonyl-imidazole (CDI)-activated clarithromycin derivative depicted in Scheme 10 may be used as a starting material to prepare a number of compounds for use in the present invention.

Scheme 10

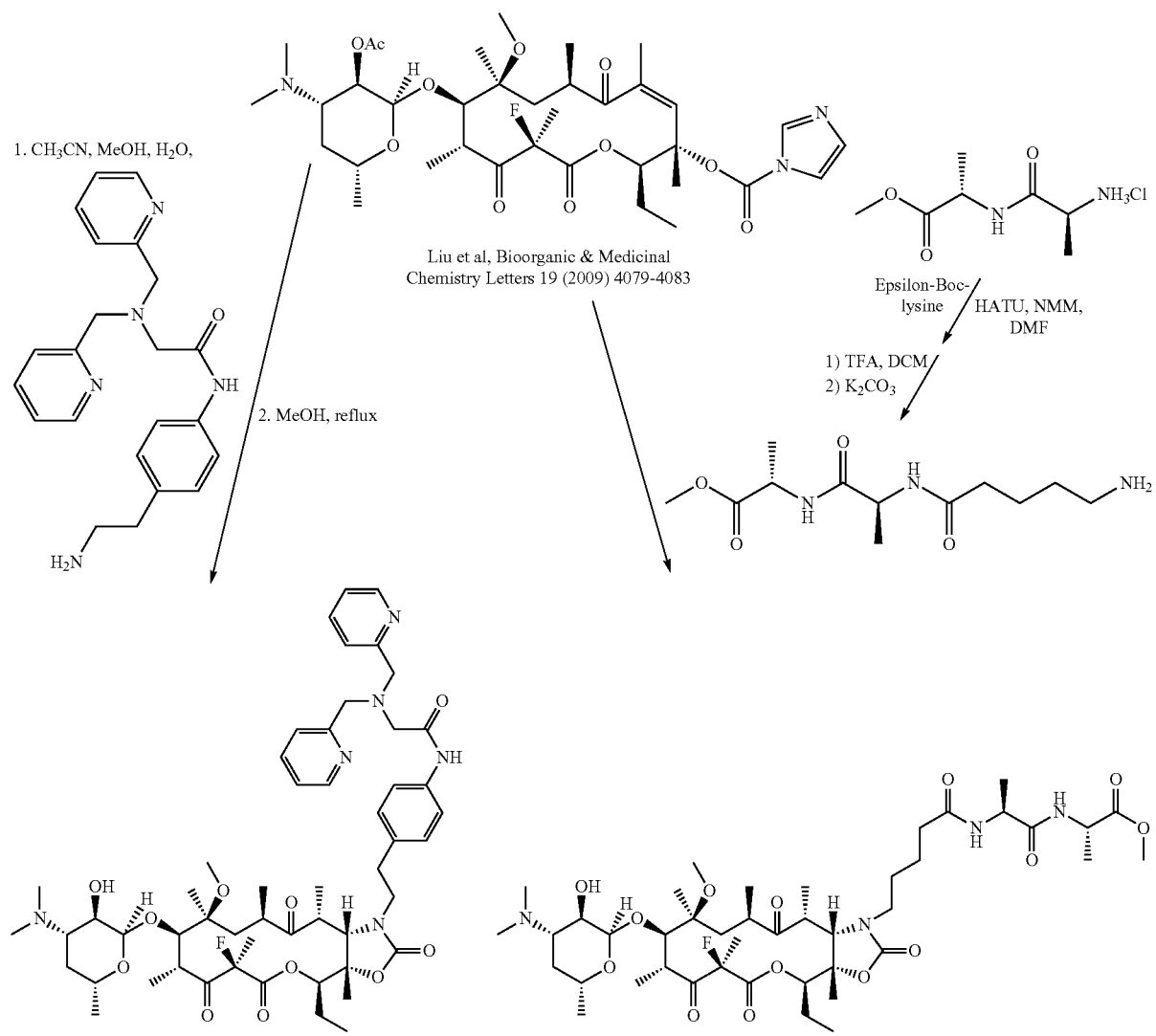

Another class of molecules useful as the vector B in the present invention includes chloramphenicol and its derivatives. Chloramphenicol is a bacteriostatic by inhibiting protein synthesis by binding to the bacterial ribosome.

As will be understood, any of the compounds herein described may be provided in the form of a pharmaceutically acceptable salt. The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine.

Procedures for Salt Formation are Conventional in the Art.

Also provided herein is a pharmaceutical composition comprising a compound according to the invention together with at least one pharmaceutically acceptable diluent or carrier.

Compositions comprising the MBL inhibitors are preferably formulated prior to administration. The active ingredients in such compositions may comprise from 0.05% to 99% by weight of the formulation. Appropriate dosages may depend on the modulator to be used, precise condition to be treated, age and weight of the patient etc. and may be routinely determined by the skilled practitioner according to principles well known in the art. By way of example, representative dosages may include 1 to 200 or 1-100 mg/kg, e.g. 5 to 70, 5-50, or 10 to 70 or 10 to 50 mg/kg.

By "pharmaceutically acceptable" is meant that the ingredients must be compatible with other ingredients of the composition as well as physiologically acceptable to the recipient. Pharmaceutical compositions according to the present invention may be formulated according to techniques and procedures well known in the art and widely described in the literature and may comprise any of the known carriers, diluents or excipients. Other ingredients may of course also be included, according to techniques well known in the art e.g. stabilisers, preservatives, etc. The formulations may be in the form of sterile aqueous solutions and/or suspensions of the pharmaceutically active ingredients, aerosols, ointments and the like. The formulations may also be in a sustained release form e.g. microparticles, nanoparticles, emulsions, nanosuspensions, lipid particles or oils. Further, an important aspect of formulation of antibacterial agents is in the form of films, patches or folios having the MBL inhibitor coated on the surface; these may also be used in the present invention.

The administration may be by any suitable method known in the medicinal arts, including oral, parenteral, topical, subcutaneous administration or by inhalation. The MBL inhibitor or formulations comprising the MBL inhibitor may be administered in a single dose to be taken at regular intervals e.g. once or twice a day, once every 48 hours or once every 72 hours. Sustained formulations may be given at longer intervals e.g. 1 to 2 times a month or every three months. The precise dosage of the active compounds to be administered, the number of daily or monthly doses and the length of the course of treatment will depend on a number of factors, including the age of the patient and their weight. The compositions may be formulated according to techniques and procedures well known in the literature and may comprise any of the known carriers, diluents or excipients. For example the compositions/formulations which can be used in the present invention which are suitable for parenteral administration conveniently may comprise sterile aqueous solutions and/or suspensions of pharmaceutically active ingredients preferably made isotonic with the blood of the recipient generally using sodium chloride, glycerin, glucose, mannitol, sorbitol and the like. In addition, the composition may contain any of a number of adjuvants, such as buffers, preservatives, dispersing agents, agents that promote rapid onset of action or prolonged duration of action. Compositions/formulations suitable for oral administration may be in sterile purified stock powder form, preferably covered by an envelope or envelopes which may contain any of a number or adjuvants such as buffers, preservative agents, agents that promote prolonged or rapid release. Compositions/formulations for use in the present invention suitable for local or topical administration may comprise the MBL inhibitor mixed with known suitable ingredients such as paraffin, vaseline, cetanol, glycerol and its like, to form suitable ointments or creams.

The invention will be described in more detail in the following non-limiting examples.

General Procedures

All reagents and solvents used are of commercial grade and were used without further purifications prior to use. NMR ($^1$H, $^{13}$C) spectra were recorded on a Bruker AVII-400 MHz, a DPX-300 MHz or a DPX-200 MHz spectrometer. Coupling constants (J) are reported in hertz, and chemical shifts are reported in parts per million (ppm) relative to CDCl$_3$ (7.26 ppm for $^1$H and 77.16 ppm for $^{13}$C) and [D$_6$] DMSO (2.50 ppm for $^1$H and 39.52 ppm for $^{13}$C). IR spectra were obtained on a Perkin-Elmer Spectrum BX series FT-IR spectrometer and only selected peaks are reported. All yields are uncorrected.

Example 1—Synthesis of N,N'-dipicolyl-N-propagyl amine

N,N'-dipicolylamine (5.0 mL, 22.9 mmol, 1.0 eq.) was diluted in THF (55.7 mL, 700 mmol, 25 eq.) followed by addition of K$_2$CO$_3$ (15.40 g, 111.4 mmol, 4.0 eq.) and propagyl bromide (4.34 mL 80%, 39.0 mmol, 1.4 eq.). The mixture was heated to reflux under heavy stirring and left for three hours. The deep red slurry was then cooled down to room temperature, filtered using a glass filter, the filter washed with 2×20 mL dichloromethane and the combined organic phases were concentrated under reduced pressure to a rust-red oil. The crude product was purified using column chromatography and the product was eluted from an alumina column by methanol in dichloromethane (1-5%) yielding 5.55 g (86%). $^1$H and $^{13}$C NMR are in accordance with published results.

Example 2—General Procedure for the Synthesis of Triazoles

Copper sulfate heptahydrate (250 mg, 1.0 mmol, 1.0 eq.) in 2.5 mL H$_2$O and sodium (+)ascorbate (396 mg, 2.0 mmol, 2.0 eq.) in 2.5 mL H$_2$O were added simultaneously to a stirring solution of the alkyne (1.0 mmol, 1.0 eq.) in 2.5 mL tBuOH. The azide solution (4.0 mL 25% in tBuOMe, 1.0 mmol, 1.0 eq) was then added and the solution was stirred at room temperature for 16 hours. EDTA (293 mg, 1.0 mmol, 1.0 eq) was then added to the stirring solution and left for 60 minutes before the mixture was diluted with 50 mL H$_2$O and the pH of the mixture was adjusted to >10 with 1M NaOH. The slurry was then extracted with 50 mL EtOAc and 50 mL dichloromethane. The combined organic phases were dried over K$_2$CO$_3$ and concentrated under reduced pressure to give a dark red oil/semisolid. The crude products were purified using column chromatography by eluting a neutral Al$_2$O$_3$ column with 1-10% methanol in dichloromethane.

Example 3—Preparation of 1-(1-(4-methoxybenzyl)-1H-1,2,3-triazol-4-yl)-N,N-bis(pyridin-2-ylmethyl)methanamine (OAA2168)

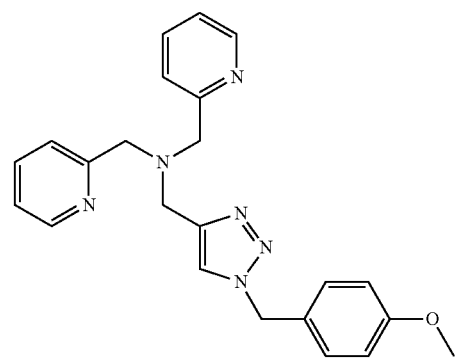 [SMILES: COc1ccc(Cn2cc(CN(Cc3ccccn3)Cc3ccccn3)nn2)cc1]

Yield: 188 mg (49%). $^1$H NMR (200 MHz, Chloroform-d) δ 8.55-8.45 (m, 2H), 7.70-7.48 (m, 4H), 7.46 (s, 1H), 7.25-7.06 (m, 4H), 6.89 (m, 2H), 5.44 (s, 2H), 3.85 (s, 2H), 3.81 (s, 4H), 3.80 (s, 3H). HRMS e/z calculated for C$_{22}$H$_{23}$N$_6$O (M+1): 387.1928, found 387.1927.

Example 4—Preparation of 1-(1-(6-methoxynaphthalen-2-yl)-1H-1,2,3-triazol-4-yl)-N,N-bis(pyridin-2 ylmethyl)methanamine (OAA4067)

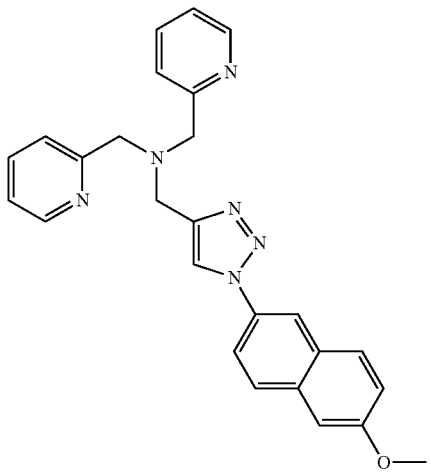 [SMILES: COc1ccc2cc(-n3cc(CN(Cc4ccccn4)Cc4ccccn4)nn3)ccc2c1]

Yield: 286 mg (86%). $^1$H NMR (400 MHz, Chloroform-d) δ 8.57 (d, J=4.8 Hz, 2H), 8.16 (s, 1H), 8.09 (s, 1H), 7.93-7.76 (m, 4H), 7.68 (t, J=7.6 Hz, 2H), 7.62 (d, J=7.8 Hz, 2H), 7.25-7.12 (m, 4H), 4.01 (s, 2H), 3.99-3.87 (m, 7H). 13C NMR (101 MHz, CDCl3) δ 158.6, 149.3, 136.7, 134.4, 129.9, 128.7, 128.6, 123.6, 122.3, 120.5, 119.8, 118.6, 115.1, 106.0, 59.9, 55.6, 48.9. HRMS e/z calculated for $C_{26}H_{25}N_6O$ (M+H): 437.2084, found 437.2086.

Example 5—Preparation of 1-(pyridin-2-yl)-N-(pyridin-2-ylmethyl)-N-((1-(3,4,5-trimethoxyphenyl)-1H-1,2,3-triazol-4-yl)methyl)methanamine (OAA4069)

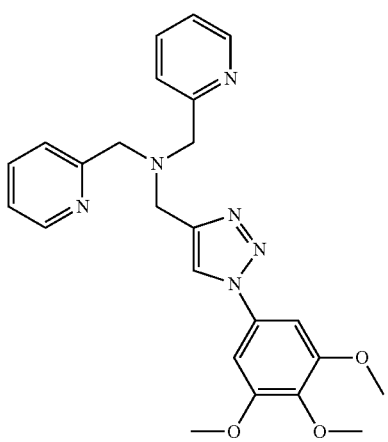 [SMILES: COc1cc(-n2cc(CN(Cc3ccccn3)Cc3ccccn3)nn2)cc(OC)c1OC]

Yield: 261 mg (78%). $^1$H NMR (400 MHz, Chloroform-d) δ 8.56 (d, J=4.7 Hz, 2H), 8.01 (s, 1H), 7.66 (d, J=7.6 Hz, 2H), 7.58 (d, J=7.8 Hz, 2H), 7.23-7.08 (m, 2H), 6.94 (s, 2H), 3.98 (s, 2H), 3.94 (s, 6H), 3.91 (s, 4H), 3.89 (s, 3H). 13C NMR (101 MHz, CDCl3) δ 159.3, 154.0, 149.3, 145.2, 138.4, 136.6, 133.2, 123.6, 122.2, 121.6, 98.7, 61.2, 59.9, 56.6, 48.7. HRMS e/z calculated for $C_{24}H_{27}N_6O_3$ (M+H): 447.2139, found 447.2143.

Example 6—Preparation of 1-(1-(4-nitrobenzyl)-1H-1,2,3-triazol-4-yl)-N,N-bis(pyridin-2-ylmethyl)methanamine (OAA4071)

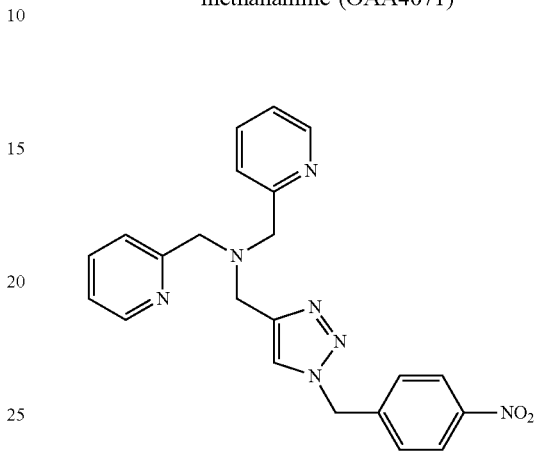

Yield: 176 mg (42%). 1H NMR (400 MHz, Chloroform-d) δ 8.55 (d, J=4.8 Hz, 2H), 8.21 (d, J=8.4 Hz, 2H), 7.90 (s, 1H), 7.69 (t, J=7.6 Hz, 2H), 7.58 (d, J=7.8 Hz, 2H), 7.41 (d, J=8.3 Hz, 2H), 7.24-7.12 (m, 2H), 5.64 (s, 2H), 4.01 (s, 2H), 3.95 (s, 4H). 13C NMR (101 MHz, CDCl3) δ 148.97, 141.92, 137.19, 128.74, 124.42, 124.10, 122.71, 59.01, 53.22, 48.73. HRMS e/z calculated for $C_{22}H_{22}N_7O_2$ (M+H): 416.1829, found 416.1825.

Example 7—Preparation of 1-(pyridin-2-yl)-N-(pyridin-2-ylmethyl)-N-((1-(3,4,5-trimethoxybenzyl)-1H-1,2,3-triazol-4-yl)methyl)methanamine (OAA4073)

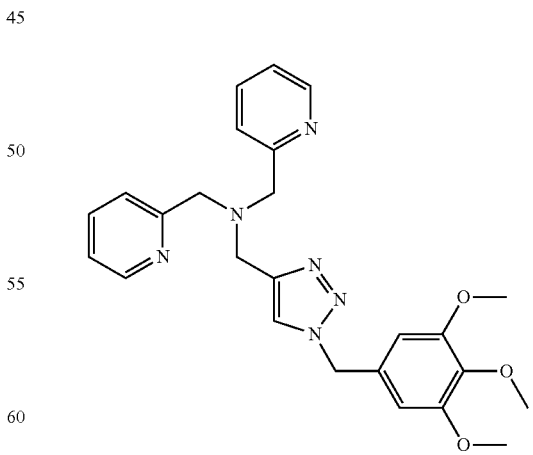

Yield: 138 mg (30%). 1H NMR (400 MHz, Chloroform-d) δ 8.52 (d, J=4.7 Hz, 2H), 7.69-7.59 (m, 3H), 7.54 (d, J=7.8 Hz, 2H), 7.22-7.01 (m, 2H), 6.47 (s, 2H), 5.43 (s, 2H), 3.91 (s, 2H), 3.90-3.81 (m, 7H), 3.80 (s, 6H). 13C NMR (101 MHz, CDCl3) δ 153.8, 152.3, 149.2, 139.4, 137.6, 136.7, 134.8, 130.5, 126.3, 123.6, 123.3, 123.1, 122.3, 111.8, 105.3, 103.3, 61.0, 59.5, 56.3, 54.4, 48.8. HRMS e/z calculated for $C_{25}H_{29}N_6O_3$ (M+H): 461.2296, found 461.2296.

Example 8—Preparation of 1-(1-(4-methoxy-3-nitrobenzyl)-1H-1,2,3-triazol-4-yl)-N,N-bis(pyridin-2-ylmethyl)methanamine (OAA4075)

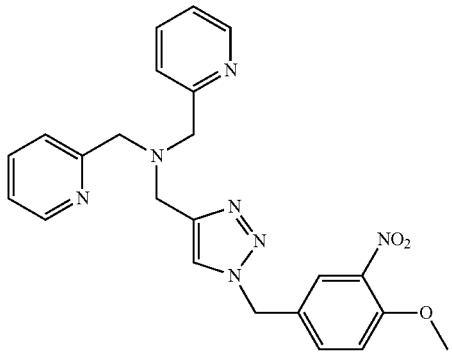 [SMILES: COc1ccc(Cn2cc(CN(Cc3ccccn3)Cc3ccccn3)nn2)cc1[N+](=O)[O-]]

Yield: 191 mg (43%). 1H NMR (400 MHz, Chloroform-d) δ 8.52 (d, J=4.7 Hz, 2H), 7.81 (s, 1H), 7.64 (t, J=7.6 Hz, 2H), 7.59 (s, 1H), 7.53 (d, J=7.8 Hz, 2H), 7.45 (d, J=8.6 Hz, 1H), 7.19-7.10 (m, 2H), 7.07 (d, J=8.7 Hz, 1H), 5.49 (s, 2H), 3.96 (s, 3H), 3.88 (s, 2H), 3.82 (s, 4H). 13C NMR (101 MHz, CDCl3) δ 159.2, 153.3, 149.3, 145.3, 139.7, 136.6, 133.9, 127.4, 125.4, 123.5, 123.1, 122.2, 114.5, 59.7, 56.9, 52.7, 48.7. HRMS e/z calculated for $C_{23}H_{24}N_7O_3$ (M+H): 446.1935, found 446.1940.

Example 9—Preparation of 1-(1-β-bromo-4-methoxybenzyl)-1H-1,2,3-triazol-4-yl)-N,N-bis(pyridin-2-ylmethyl)methanamine (OAA4077)

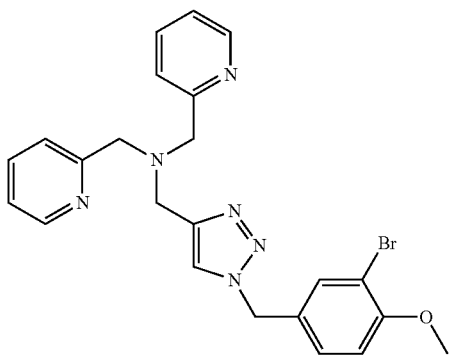 [SMILES: COc1ccc(Cn2cc(CN(Cc3ccccn3)Cc3ccccn3)nn2)cc1Br]

Yield: 228 mg (48%). HRMS e/z calculated for C23H24N6OBr (M+H): 479.1189, found 479.1196.

Example 10—Preparation of 1-(1-(dibenzo[b,d]furan-4-yl)-1H-1,2,3-triazol-4-yl)-N,N-bis(pyridin-2-ylmethyl)methanamine (OAA4079)

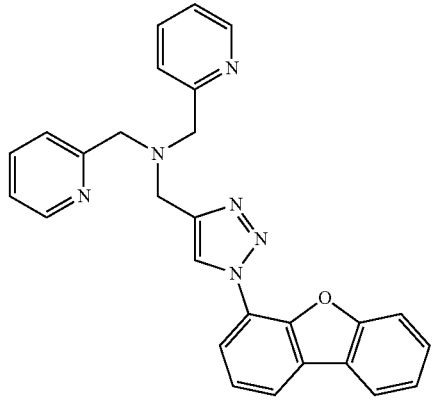 [SMILES: c1ccc(CN(Cc2ccccn2)Cc2cn(-c3cccc4c3oc3ccccc34)nn2)nc1]

Yield: 231 mg (52%). 1H NMR (400 MHz, Chloroform-d) δ 8.69 (s, 1H), 8.57 (d, J=4.8 Hz, 2H), 8.16 (d, J=8.0 Hz, 1H), 8.01 (t, J=8.1 Hz, 2H), 7.76-7.62 (m, 5H), 7.61-7.39 (m, 4H), 7.16 (t, J=5.6 Hz, 2H), 4.08 (s, 2H), 3.99 (s, 4H). 13C NMR (101 MHz, CDCl3) δ 159.3, 156.4, 149.3, 145.7, 145.1, 136.7, 128.3, 126.8, 124.2, 123.9, 123.7, 123.5, 122.7, 122.2, 121.2, 120.6, 119.9, 115.1, 112.2, 59.9, 49.0. HRMS e/z calculated for $C_{27}H_{23}N_6O$ (M+H): 447.1928, found 447.1931.

Example 11—Preparation of 1-(1-(2,4-dimethoxyphenyl)-1H-1,2,3-triazol-4-yl)-N,N-bis(pyridin-2-ylmethyl)methanamine (OAA4081)

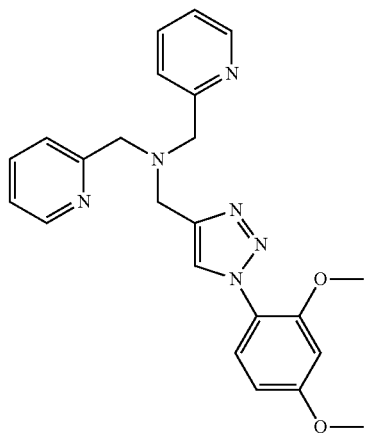 [SMILES: COc1ccc(-n2cc(CN(Cc3ccccn3)Cc3ccccn3)nn2)c(OC)c1]

Yield: 112 mg (27%). $^1$H NMR (400 MHz, Chloroform-d) δ 8.53 (d, J=4.7 Hz, 2H), 8.01 (s, 1H), 7.64 (dq, J=11.2, 6.0, 4.3 Hz, 5H), 7.14 (t, J=5.9 Hz, 2H), 6.60 (d, J=5.2 Hz, 2H), 3.97 (s, 2H), 3.90 (s, 4H), 3.87 (s, 3H), 3.82 (s, 3H). $^{13}$C NMR (101 MHz, CDCl$_3$) δ 161.3, 159.6, 152.8, 149.2, 143.7, 136.6, 126.7, 125.3, 123.4, 122.1, 120.4, 104.9, 99.8, 59.8, 56.1, 55.8, 49.0. HRMS e/z calculated for $C_{23}H_{25}N_6O_2$ (M+H): 417.2034, found 417.2033. FIRMS e/z calculated for $C_{23}H_{25}N_6O_2$ (M+H): 417.2034, found 417.2033.

Example 12—Preparation of 1-(pyridin-2-yl)-N-(pyridin-2-ylmethyl)-N-((1-(4-(trifluoromethyl)phenyl)-1H-1,2,3-triazol-4-yl)methyl)methanamine (OAA4085)

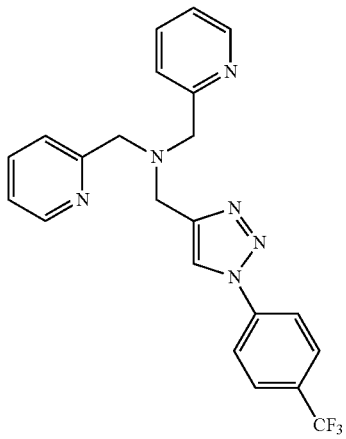 [SMILES: FC(F)(F)c1ccc(-n2cc(CN(Cc3ccccn3)Cc3ccccn3)nn2)cc1]

Yield: 208 mg (49%). 1H NMR (400 MHz, Chloroform-d) δ 8.54 (d, J=4.7 Hz, 2H), 7.95 (s, 1H), 7.86 (d, J=7.7 Hz, 1H), 7.74 (t, J=7.6 Hz, 1H), 7.67 (t, J=8.1 Hz, 3H), 7.62-7.50 (m, 3H), 7.21-7.07 (m, 2H), 3.98 (s, 2H), 3.90 (s, 4H). HRMS e/z calculated for C22H20N6F3 (M+H): 425.1696, found 425.1698.

Example 13—Preparation of 1-(1-(4-methoxyphenyl)-1H-1,2,3-triazol-4-yl)-N,N-bis(pyridin-2-ylmethyl)methanamine (OAA2172)

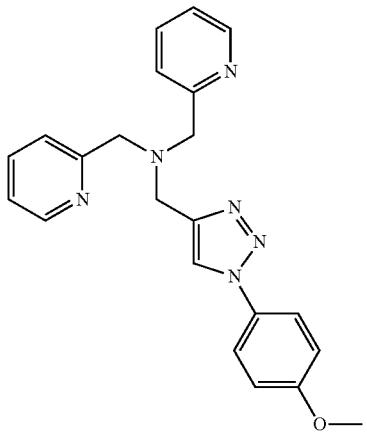 [SMILES: COc1ccc(-n2cc(CN(Cc3ccccn3)Cc3ccccn3)nn2)cc1]

Yield: 167 mg (42%). $^1$H NMR (200 MHz, Chloroform-d) δ 8.54 (d, J=4.5 Hz, 2H), 7.96 (s, 1H), 7.74-7.51 (m, 6H), 7.16 (dd, J=8.5, 3.3 Hz, 2H), 7.07-6.93 (m, 2H), 3.95 (s, 2H), 3.89 (s, 3H), 3.86 (s, 3H). $^{13}$C NMR (75 MHz, CDCl$_3$) δ 160.1, 159.5, 149.4, 145.1, 136.9, 131.0, 123.8, 122.5, 121.8, 115.4, 115.1, 60.1, 56.0, 49.0. HRMS e/z calculated for $C_{22}H_{23}N_6O$ (M+1): 387.1928, found 387.1927.

Example 14—Preparation of tert-Butyl (4-aminophenethyl)carbamate 4-(2-aminoethyl)aniline (5.00 grams, 36.7 mmol, 1.0 eq) was dissolved in 50 mL EtOAc and placed in a water bath. To the rapidly stirring solution, a mixture of boc anhydride (8.25 grams, 37.8 mmol, 1.03 eq) in 50 mL EtOAc was added dropwise. Upon addition of the anhydride, the mixture turned into a white slurry, which after 4 hours became a pale yellow clear solution. Reaction left overnight. The crude mixture was concentrated under reduced pressure to a pale yellow oil, diluted with 10 mL hot EtOAc and mixed with 50 mL hot heptane. The mixture was placed in an ice bath to facilitate precipitation. The white crystals were filtered and dried to yield 7.11 grams (82%). $^1$H NMR (400 MHz, DMSO-d6) δ 6.82 (d, J=7.8 Hz, 2H), 6.76 (s, 1H), 6.47 (d, J=7.8 Hz, 2H), 4.82 (s, 2H), 3.02 (q, J=6.4 Hz, 2H), 2.47 (m, 2H), 1.37 (s, 9H).

Example 15—Preparation of tert-Butyl (4-(2-chloroacetamido)phenethyl)carbamate tert-Butyl (4-aminophenethyl)carbamate prepared according to Example 14 (7.50 grams, 31.7 mmol, 1.0 eq) was dissolved in CH$_2$Cl$_2$ (500 mL) and cooled to 0° C. in an ice bath. DMAP (6.23 g, 51.0 mmol, 1.6 eq) was added in one go and the mixture was allowed to stand for 10 minutes before a solution of chloroacetyl chloride (3.00 ml, 37.7 mmol, 1.2 eq) in 100 ml CH$_2$Cl$_2$ was added drop wise over 20 minutes to the stirring mixture. The mixture was then left at 0° C. for 30 minutes and at room temperature for 3 hours before it was concentrated under reduced pressure. The sticky red residue was dissolved in CH$_2$Cl$_2$ (250 mL) and washed with 0.5 M aqueous acetic acid (2×200 mL), 0.5 M aqueous NaHCO$_3$ (1×100 mL) and dried on anhydrous K$_2$CO$_3$. The solution was filtered through a (4 cm×5 cm long) silica gel plug using 75% ethyl acetate in heptane to elute. Removal of the volatiles under reduce pressure yielded 7.46 g of the title compound (23.8 mmol, 75%). $^1$H NMR (300 MHz, DMSO-d$_6$) δ 10.21 (s, 1H), 7.49 (d, J=8.4 Hz, 2H), 7.14 (d, J=8.4 Hz, 2H), 6.84 (t, J=5.6 Hz, 1H), 4.23 (s, 2H), 3.18-2.99 (m, 2H), 2.74-2.56 (m, 2H), 1.36 (s, 9H). $^{13}$C NMR (101 MHz, DMSO) δ 164.4, 155.5, 136.5, 134.9, 128.9, 119.4, 77.4, 43.5, 41.5, 34.9, 28.2.

Example 16—Preparation of tert-butyl (4-(2-(bis(pyridin-2-ylmethyl)amino) acetamido)phenethyl)carbamate The □-chloro amide prepared in Example 15 (7.44 g, 23.8 mmol, 1.0 eq.) and KI (2.37 g, 14.3 mmol, 0.6 eq.) was dissolved in 500 mL MeCN and DPA (5.2 mL, 28.9 mmol, 1.2 eq.) was added to the stirring mixture. DIPEA (40.5 mL, 0.233 mol, 9.7 eq.) was then added and the mixture was heated to reflux and left for 14 hours. After cooling to room temperature, the mixture was concentrated under reduced pressure and purified by passing through a plug of alumina using 10% MeOH in CH$_2$Cl$_2$ to elute. Removal of the volatiles under reduced pressure gave the title compound in quantative yield. Material used without further purification. $^1$H NMR (400 MHz, Chloroform-d) δ 10.86 (s, 1H), 8.61 (d, J=4.1 Hz, 2H), 7.70 (d, J=8.4 Hz, 2H), 7.61 (td, J=7.7, 1.7 Hz, 2H), 7.31-7.24 (m, 2H), 7.22-7.11 (m, 4H), 4.54 (s, 1H), 3.93 (s, 4H), 3.45 (s, 2H), 3.42-3.25 (m, 2H), 2.76 (t, J=6.8 Hz, 2H), 1.42 (s, 9H). $^{13}$C NMR (75 MHz, CDCl3) δ 169.8, 158.2, 155.9, 149.5, 137.1, 136.7, 134.4, 129.2, 123.3, 122.6, 112.0, 79.2, 60.4, 58.8, 41.9, 35.7, 28.5.

Example 17—Preparation of N-(4-(2-aminoethyl)phenyl)-2-(bis(pyridin-2-ylmethyl)amino)acetamide The boc-protected amine prepared in Example 16 (200 mg, 0.42 mmol) was dissolved in 20 mL DCM and cooled to 0° C. in an ice-water bath. Trifluoroacetic acid (2 mL) was then added to the stirring solution over the course of 5 minutes. The reaction was left at 0° C. for 15 minutes before warming up to room temperature. The reaction was left for an additional two hours at room temperature, before it was concentrated under reduced pressure to a brown oil. The crude material was dissolved in 30 mL 0.5M NaHCO₃ and extracted with 3×20 mL EtOAc. The combined organic phases were pooled and washed with 50 mL 0.5M NaHCO₃ and then dried over K₂OC₃, filtered and concentrated under reduced pressure to give 155 mg of the title compound as a pale brown oil (98%). ¹H NMR (400 MHz, DMSO-d6) δ 10.53 (s, 1H), 8.64-8.41 (m, 2H), 7.75 (td, J=7.6, 1.8 Hz, 2H), 7.58 (d, J=8.4 Hz, 2H), 7.45 (d, J=7.8 Hz, 2H), 7.27 (ddd, J=7.5, 4.9, 1.0 Hz, 2H), 7.15 (d, J=8.5 Hz, 2H), 3.90 (s, 4H), 3.41 (s, 2H), 2.73 (t, J=7.1 Hz, 2H), 2.58 (t, J=7.1 Hz, 2H). ¹³C NMR (101 MHz, DMSO) δ 169.0, 158.4, 149.0, 136.7, 136.6, 135.3, 128.9, 123.0, 122.4, 119.0, 59.4, 57.8, 43.7. HRMS e/z calculated for C₂₂H₂₅N₅O: 375.2059, found 376.2133 (M+H).

Example 18—Preparation of 4-((4-(2-(bis(pyridin-2-ylmethyl)amino) acetamido)phenethyl)amino)-4-oxobutanoic acid The amine prepared in Example 17 (100 mg, 0.27 mmol) was dissolved in 10 mL acetone and cooled to 0° C. in an ice-water bath. Succinic anhydride (27 mg, 0.27 mmol) was then added in one portion to the stirring solution. The ice-water bath was removed and the reaction was allowed to stir at room temperature overnight. The crude mixture was then concentrated under reduced pressure and suspended in diethyl ether (10 mL). The mixture was shaken and the pale precipitate was filtered off to give 36 mg of the title compound as a pale yellow solid (28%). ¹H NMR (400 MHz, DMSO-d6) δ 10.52 (s, 1H), 8.58 (d, J=4.6 Hz, 2H), 7.94 (s, 1H), 7.76 (t, J=7.5 Hz, 2H), 7.59 (d, J=8.2 Hz, 2H), 7.45 (d, J=7.7 Hz, 2H), 7.32-7.21 (m, 2H), 7.16 (d, J=8.1 Hz, 2H), 3.91 (s, 4H), 3.55-3.09 (m, 7H), 2.74-2.58 (m, 2H), 2.40 (t, J=6.9 Hz, 2H), 2.28 (t, J=6.9 Hz, 2H). ¹³C NMR (101 MHz, DMSO) δ 173.84, 170.87, 169.02, 158.40, 149.01, 136.81, 136.67, 134.40, 128.89, 123.03, 122.39, 119.01, 59.42, 57.80, 40.32, 34.61, 30.15, 29.36. HRMS e/z calculated for C₂₆H₂₉N₅O₄: 475.2220, found 476.2293 (M+H).

Example 19—Preparation of Methyl (4-((4-(2-(bis(pyridin-2-ylmethyl)amino) acetamido)phenethyl)amino)-4-oxobutanoyl)-D-alanyl-D-alaninate

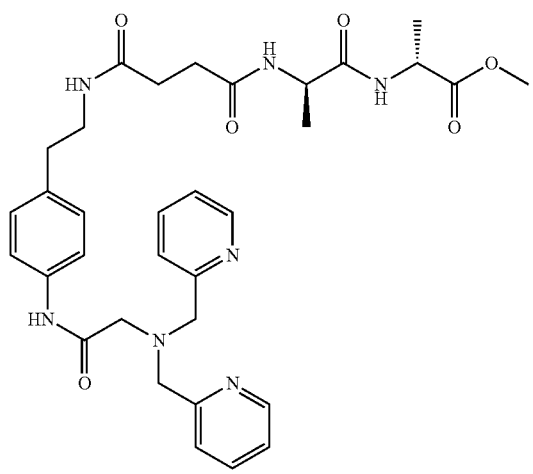 [SMILES: COC(=O)[C@@H](C)NC(=O)[C@@H](C)NC(=O)CCC(=O)NCCc1ccc(NC(=O)CN(Cc2ccccn2)Cc2ccccn2)cc1]

The free acid prepared in Example 18 (0.250 g, 0.526 mmol) was dissolved in DMF (2 mL) and cooled to 0° C. in an ice-water bath. D-alanyl-D-alanine methyl ester hydrochloride (116 mg, 0.551 mmol, 1.05 equiv.) and HATU (211 mg, 0.555 mmol, 1.06 equiv) were then added, before NMM (120 uL, 1.09 mmol, 2.1 equiv.) was added to the stirring mixture. The mixture was left in the ice-water bath for 30 minutes before slowly heating to room temperature. The mixture was then left for 18 hours at room temperature. The mixture was then diluted with 50 mL 0.5 M K₂CO₃ and extracted with 5×10 mL EtOAc. The combined organic phases were combined, washed with fresh 0.5 M K₂CO₃ (4×25 mL) and dried over K₂CO₃, filtered and concentrated under reduced pressure. This afforded 0.159 mg of the title compound as a pale semisolid (0.252 mmol, 48%). ¹H NMR (300 MHz, DMSO-do) δ 10.53 (s, 1H), 8.63-8.49 (m, 2H), 8.25 (d, J=7.1 Hz, 1H), 8.05 (d, J=7.8 Hz, 1H), 7.92 (t, J=5.6 Hz, 1H), 7.80-7.70 (m, 2H), 7.63-7.55 (m, 2H), 7.52-7.38 (m, 2H), 7.33-7.23 (m, 2H), 7.19-7.06 (m, 2H), 4.36-4.15 (m, 2H), 3.90 (s, 4H), 3.59 (s, 3H), 3.41 (s, 2H), 3.26-3.13 (m, 2H), 2.69-2.58 (m, 2H), 2.29 (d, J=10.0 Hz, 4H), 1.29 (d, J=7.3 Hz, 3H), 1.19 (d, J=7.1 Hz, 3H). ¹³C NMR (101 MHz, DMSO) δ 172.9, 172.3, 171.3, 171.1, 169.0, 158.4, 149.0, 136.8, 136.7, 134.4, 128.9, 123.0, 122.4, 119.0, 59.4, 57.8, 51.8, 47.6, 47.5, 40.20, 38.2, 34.6, 30.6, 17.9, 16.8. e/z calculated for C₃₃H₄₁N₇O₆: 631, found 632.3 (M+H).

Example 20—Preparation of methyl (4-((4-(2-(bis(pyridin-2-ylmethyl)amino)acetamido)phenethyl)amino)-4-oxobutanoyl)-D-alanyl-D-alanoic acid

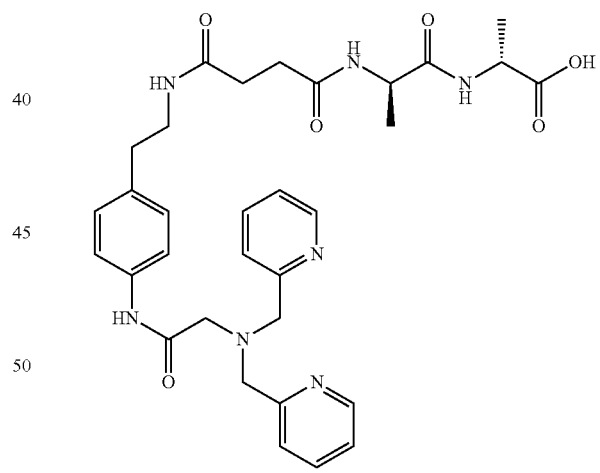

The ester prepared in Example 19 (50 mg, 79 μmop was dissolved in THF (1 mL) cooled to 0° C. using an ice water bath and water (150 μL) and aqueous 0.5 M lithium hydroxide solution (160 μL, 80 μmol). The reaction was stirred for 2.5 h until TLC (5% MeOH in CH₂Cl₂, alumina) indicated consumption of the ester. The pH of the solution was adjusted to 7 using 0.1 M HCl and the solvent removed under reduced pressure. The mixture was dissolved in ethanol and filtered to remove salts and the solvent removed under reduced pressure. This afforded 22 mg of the title compound as a pale green solid (36 μmol, 50%). ¹H NMR (300 MHz, DMSO-d6) δ 10.56 (s, 1H), 8.65-8.40 (m, 2H), 8.23 (d, J=7.7 Hz, 1H), 8.02 (t, J=5.5 Hz, 1H), 7.81-7.67 (m, 2H), 7.63-7.55 (m, 2H), 7.51 (d, J=6.0 Hz, 1H), 7.48-7.43 (m, 2H), 7.33-7.23 (m, 2H), 7.20-7.10 (m, 2H), 4.15 (p, J=7.2 Hz, 1H), 3.91 (s, 4H), 3.65 (p, J=6.7 Hz, 1H), 3.42 (s, 2H), 3.22 (q, J=6.6 Hz, 2H), 2.67 (d, J=13.0 Hz, 2H), 2.40-2.23 (m, 4H), 1.22-1.11 (m, 6H). $^{13}$C NMR (101 MHz, DMSO) δ 173.7, 171.2, 171.1, 170.7, 169.1, 158.4, 149.0, 136.8, 136.7, 134.4, 128.9, 123.0, 122.4, 119.0, 59.4, 57.8, 49.9, 48.5, 38.2, 34.6, 31.0, 30.9, 19.2, 18.0. e/z calculated for $C_{32}H_{39}N_7O_6$: 617, found 618.3 (M+H).

Example 21—Preparation of methyl (4-((4-(2-(bis(pyridin-2-ylmethyl)amino)acetamido)phenethyl)amino)-4-oxobutanoyl)-D-alaninate

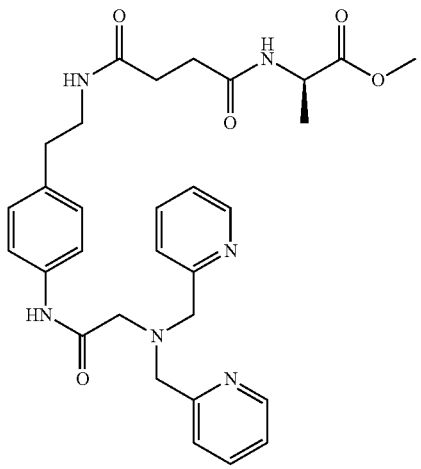 [SMILES: COC(=O)[C@@H](C)NC(=O)CCC(=O)NCCc1ccc(NC(=O)CN(Cc2ccccn2)Cc2ccccn2)cc1]

The free acid prepared in Example 18 (1.013 g, 2.13 mmol) was dissolved in DMF (10 mL) and cooled to 0° C. in an ice-water bath. D-alanyl-methyl ester hydrochloride (315 mg, 2.26 mmol, 1.06 equiv.) and HATU (850 mg, 2.24 mmol, 1.05 equiv) were then added, before NMM (500 µL, 4.55 mmol, 2.14 equiv.) was added to the stirring mixture. The mixture was left in the ice-water bath for 30 minutes before slowly heating to room temperature. The mixture was then left for 18 hours at room temperature. The mixture was then diluted with 150 mL 0.5 M $K_2CO_3$ and extracted with 5×50 mL EtOAc. The combined organic phases were combined, washed with fresh 0.5 M $K_2CO_3$ (100 mL), brine (2×100 mL) and dried over $K_2CO_3$, filtered and concentrated under reduced pressure. This afforded 1.00 g of the title compound as a pale semisolid (1.78 mmol, 84%). $^1$H NMR (400 MHz, DMSO-d$_6$) δ 10.53 (s, 1H), 8.62-8.53 (m, 2H), 8.26 (d, J=7.0 Hz, 1H), 7.88 (t, J=5.7 Hz, 1H), 7.80-7.67 (m, 2H), 7.59 (d, J=8.1 Hz, 2H), 7.50-7.37 (m, 2H), 7.35-7.21 (m, 2H), 7.19-7.10 (m, 2H), 4.24 (p, J=7.2 Hz, 1H), 3.90 (s, 4H), 3.60 (s, 3H), 3.41 (s, 2H), 3.28-3.16 (m, 2H), 2.65 (t, J=7.4 Hz, 2H), 2.43-2.16 (m, 4H), 1.25 (d, J=7.3 Hz, 3H). $^{13}$C NMR (101 MHz, DMSO) δ 173.2, 171.3, 171.0, 169.0, 158.4, 149.0, 136.8, 136.7, 134.4, 128.9, 123.0, 122.4, 119.0, 59.4, 57.8, 51.7, 47.5, 38.2, 34.6, 30.6, 30.4, 16.9. e/z calculated for $C_{30}H_{36}N_6O_5$: 560, found 561.3 (M+H).

Example 22—Preparation of methyl (4-((4-(2-(bis(pyridin-2-ylmethyl)amino)acetamido)phenethyl)amino)-4-oxobutanoyl)-D-alanoic acid

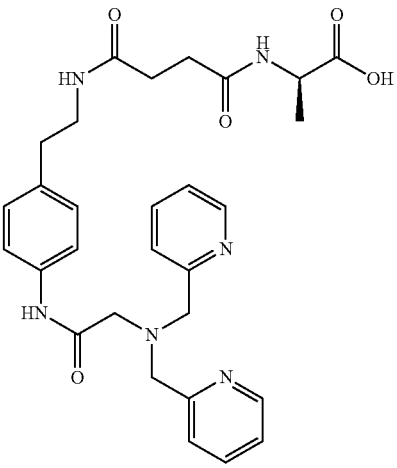 [SMILES: C[C@@H](NC(=O)CCC(=O)NCCc1ccc(NC(=O)CN(Cc2ccccn2)Cc2ccccn2)cc1)C(=O)O]

The ester prepared in Example 21 (0.857 g, 1.53 mmol) was dissolved in THF (15 mL) cooled to 0° C. using an ice water bath and aqueous 0.5 M lithium hydroxide solution (3.4 mL, 1.7 mmol) added. The reaction was stirred for 2.5 h until TLC (5% MeOH in $CH_2Cl_2$, alumina) indicated consumption of the starting material. The pH of the solution was adjusted to 7 using 0.1 M HCl and the solvent removed under reduced pressure. The mixture was dissolved in a minimum of ethanol (3 mL) and precipitated with excess acetone (40 mL). The resulting precipitate was collected by filtration and dissolved again in fresh ethanol. After filtration to remove salts the solvent was removed under reduced pressure. This afforded 0.437 g of the title compound as a pale green solid (0.799 mmol, 52%). 1H NMR (400 MHz, DMSO-d6) δ 10.55 (s, 1H), 8.63-8.50 (m, 2H), 7.98 (t, J=5.6 Hz, 1H), 7.79-7.71 (m, 2H), 7.59 (d, J=8.4 Hz, 2H), 7.44 (d, J=7.7 Hz, 2H), 7.40 (d, J=6.6 Hz, 1H), 7.32-7.23 (m, 2H), 7.15 (d, J=8.4 Hz, 2H), 4.39 (bs, 1H), 3.90 (s, 4H), 3.80 (p, J=6.8 Hz, 1H), 3.41 (s, 2H), 3.29-3.14 (m, 2H), 2.64 (t, 0.1=7.5 Hz, 2H), 2.36-2.20 (m, 4H), 1.15 (d, J=6.8 Hz, 3H). $^{13}$C NMR (101 MHz, DMSO) δ 174.3, 171.3, 169.9, 169.1, 158.4, 149.0, 136.8, 136.7, 134.4, 128.9, 123.0, 122.4, 119.0, 59.4, 57.8, 50.0, 40.3, 34.6, 31.3, 31.2, 19.3. e/z calculated for $C_{29}H_{36}N_6O_5$: 546, found 547.3 (M+H).

Example 23—Preparation of tert-Butyl ((R)-1-(((R)-1-((4-(2-(bis(pyridin-2-ylmethyl)amino)acetamido)-phenethyl)amino)-1-oxopropan-2-yl)amino)-1-oxopropan-2-yl)carbamate The free amine prepared in Example 16 (2.88 g, 7.67 mmol) was dissolved in DMF (30 mL) and cooled to 0° C. in an ice-water bath. N-Boc-D-alanyl-D-alanioic acid (2.00 g, 7.68 mmol, 1.0 equiv.) and HBTU (2.92 g, 7.70 mmol, 1.0 equiv) were then added, before NMM (1.70 mL, 15.5 mmol, 2.02 equiv.) was added to the stirring mixture. The mixture was left in the ice-water bath for 15 minutes before slowly heating to room temperature. The mixture was then left for 4.5 hours at room temperature. The mixture was then diluted with 200 mL 0.5 M K$_2$CO$_3$ and extracted with 4×100 mL EtOAc. The combined organic phases were combined, washed with fresh 0.5 M K$_2$CO$_3$ (2×150 mL), brine (2×100 mL) and dried over Na$_2$SO$_4$, filtered and concentrated under reduced pressure. The brown oily residue was dissolved in CH$_2$Cl$_2$ and purified by column chromatography on neutral alumina using 1-2% MeOH in CH$_2$Cl$_2$ to elute, this afforded 3.66 g of the title compound as a brown semisolid (5.92 mmol, 77%). $^1$H NMR (300 MHz, DMSO-d6) δ 10.53 (s, 1H), 8.57 (ddd, J=4.9, 1.8, 0.9 Hz, 2H), 7.90 (d, J=5.6 Hz, 1H), 7.82-7.67 (m, 3H), 7.64-7.53 (m, 2H), 7.50-7.37 (m, 2H), 7.34-7.23 (m, 2H), 7.19-7.10 (m, 2H), 6.98 (d, J=7.3 Hz, 1H), 4.29-4.11 (m, 1H), 3.90 (s, 5H), 3.41 (s, 2H), 3.30-3.13 (m, 2H), 2.68-2.58 (m, 2H), 1.37 (s, 9H), 1.15 (d, J=7.0 Hz, 6H). $^{13}$C NMR (101 MHz, DMSO) δ 171.8, 169.0, 158.4, 149.0, 136.9, 136.7, 134.2, 128.9, 123.0, 122.4, 119.0, 78.1, 59.4, 57.8, 54.9, 49.8, 48.0, 40.2, 34.4, 28.1, 17.9.

Example 24—Preparation of (R)-1-(((R)-1-((4-(2-(bis(pyridin-2-ylmethyl)amino)acetamido)phenethyl)amino)-1-oxopropan-2-yl)amino)-1-oxopropan-2-aminium chloride (OAA4033)

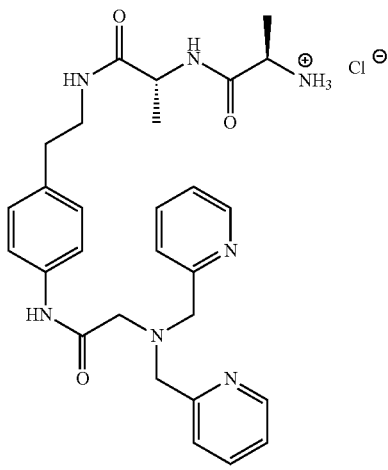 [SMILES: C[C@@H]([NH3+])C(=O)N[C@H](C)C(=O)NCCc1ccc(NC(=O)CN(Cc2ccccn2)Cc2ccccn2)cc1 ; [Cl-]]

The boc-protected amine prepared in Example 23 (3.491 g, 5.65 mmol) was dissolved in 26 mL CH$_2$Cl$_2$ and cooled to 0° C. in an ice-water bath. Trifluoroacetic acid (6.5 mL, 84.9 mmol, 15.0 equiv) in CH$_2$Cl$_2$ (6.5 mL) was then added to the stirring solution over the course of 5 minutes. The reaction was left at 0° C. for 15 minutes before warming up to room temperature. The reaction was left for an additional 3 hours at room temperature before the rapid addition of further TFA (1 mL) in CH$_2$Cl$_2$ (1 mL). After 1 h stirring TLC (5% MeOH in CH$_2$Cl$_2$, alumina) indicated consumption of the carbamate and the volatiles were removed under reduced pressure. The resulting brown oil was dissolved in CH$_2$Cl$_2$ (50 mL) and treated with 2M HCl in Et$_2$O (9 mL). After 30 min stirring the mixture oiled out, further ether (100 mL) was added causing precipitation of a pale brown solid and partial titration of the oil. The fine pale powder was collected by filtration, washed with excess fresh ether, and dried under vacuum to give 1.25 g of the title compound. The remaining sticky oil was washed with ether, then dissolved in hot ethanol, transferred to a flask and the solvent removed under reduced pressure to give a further 1.35 g of the pale brown solid. In total 2.60 g of the title compound was isolated as a pale brown solid (4.69 mmol, 83%). $^1$H NMR (300 MHz, D$_2$O) δ 8.77 (d, J=5.4 Hz, 2H), 8.53 (td, J=8.0, 1.4 Hz, 2H), 8.07 (d, J=8.0 Hz, 2H), 7.96 (t, J=6.8 Hz, 2H), 7.27 (s, 4H), 4.51 (s, 4H), 4.30-3.99 (m, 2H), 3.78 (s, 2H), 3.65-3.32 (m, 2H), 2.84 (hept, J=6.7 Hz, 2H), 1.51 (d, J=7.1 Hz, 3H), 1.27 (d, J=7.2 Hz, 3H). 13C NMR (75 MHz, D$_2$O) δ 174.8, 170.9, 170.8, 152.7, 147.3, 142.0, 137.1, 134.7, 129.9, 127.5, 126.7, 122.1, 58.3, 57.1, 50.3, 49.2, 40.7, 34.4, 17.1, 16.9. HRMS e/z calculated for C$_{28}$H$_{36}$N$_7$O$_3$: 518.2880, found 518.2879.

Example 25—Preparation of (R)-2-acetamido-N—((R)-1-((4-(2-(bis(pyridin-2-ylmethyl)amino)acetamido)phenethyl)amino)-1-oxopropan-2-yl)propanamide

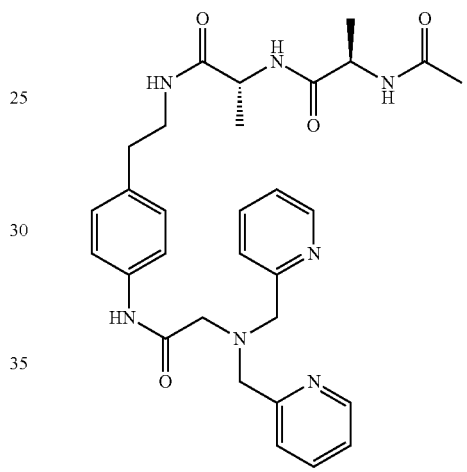

The boc-protected amine prepared in Example 23 (173 mg, 0.280 mmol) was dissolved in 2.5 mL CH$_2$Cl$_2$ and cooled to 0° C. in an ice-water bath. Trifluoroacetic acid (330 uL, 4.30 mmol, 15.4 equiv) was then added to the stirring solution over the course of 5 minutes. The reaction was left at 0° C. for 15 minutes before warming up to room temperature and stirred for 3 h then the volatiles were removed under reduced pressure. The resulting brown oil was dissolved in CH$_2$Cl$_2$ (5 mL) and Ac$_2$O (60 uL, 0.634 mmol, 2.25 equiv.) added and the reaction stirred for 18 h. The reaction was quenched with 0.5 M K$_2$CO$_3$ (5 mL). After 15 min stirring the layers were separated and the aqueous extracted with 3×10 mL CH$_2$Cl$_2$. Combined organic layers were washed with fresh 0.5 M K$_2$CO$_3$ (10 mL), dried on Na$_2$SO$_4$, filtered and the solvent removed under reduced pressure to give 78 mg of crude material which can be further purified by column chromatography to give the title compound.

Example 26—Preparation of tert-butyl (4-(2-(dibenzylamino)acetamido)phenethyl)carbamate tert-Butyl (4-(2-chloroacetamido)phenethyl)carbamate (1.002 g, 3.20 mmol, 1.0 eq.) and KI (0.597 g, 3.60 mmol, 1.25 eq.) were dissolved in 350 mL MeCN and dibenzylamine (0.74 mL, 3.85 mmol, 1.2 eq.) was added to the stirring mixture. DIPEA (5.5 mL, 31.6 mmol, 9.87 eq.) was then added and the mixture was heated to reflux and left for 17 hours. After cooling to room temperature, the mixture was concentrated under reduced pressure and purified using column chromatography on silica. The product was eluted using 20-50% ethyl acetate in heptane, yielding 1030 mg (68%) of the titled compound. ¹H NMR (400 MHz, DMSO) δ 9.54 (s, 1H), 7.48 (d, J=8.1 Hz, 2H), 7.42 (d, J=7.0 Hz, 4H), 7.34 (q, J=7.2 Hz, 4H), 7.30-7.19 (m, 2H), 7.11 (d, J=8.2 Hz, 2H), 6.83 (t, J=5.7 Hz, 1H), 3.76 (s, 4H), 3.21 (s, 2H), 3.09 (q, J=8.0, 5.6 Hz, 2H), 2.63 (t, J=8.4, 6.4 Hz, 2H), 1.37 (s, 9H). ¹³C NMR (101 MHz, DMSO) δ 168.68 (s), 155.45 (s), 140.80 (s), 138.50 (s), 136.55 (s), 134.35 (s), 128.74 (d, J=3.8 Hz), 128.27 (s), 127.95 (d, J=19.4 Hz), 127.06 (s), 119.28 (s), 77.43 (s), 57.52 (s), 56.09 (s), 40.20 (s), 34.87 (s), 28.23 (s).

Example 27—Preparation of N-(4-(2-aminoethyl) phenyl)-2-(dibenzylamino) acetamide The boc-protected amine prepared in Example 26 (550 mg, 1.16 mmol, 1 eq) was dissolved in 25 mL DCM and cooled to 0° C. in an ice-water bath. Trifluoroacetic acid (6 mL, 78.35 mmol, 67.5 eq) was then added dropwise to the stirring solution over the course of 5 minutes. The reaction was left for 1 hour at room temperature, before it was concentrated under reduced pressure to a light brown oil. The crude material was dissolved in 25 mL ethyl acetate and extracted with 50 mL 0.5 M K₂CO₃. The water phase was extracted with 3×20 mL ethyl acetate. The combined organic phases were pooled and washed with 25 mL 0.5M K₂CO₃ and then dried over K₂CO₃, filtered and concentrated under reduced pressure to give 404 mg of the title compound as a pale light oil (93%). ¹H NMR (400 MHz, DMSO) δ 9.52 (s, 1H), 7.48-7.44 (m, 2H), 7.41 (d, J=7.0 Hz, 4H), 7.34 (t, J=7.5 Hz, 4H), 7.29-7.21 (m, 2H), 7.15-7.07 (m, 2H), 3.75 (s, 4H), 3.20 (s, 2H), 2.72 (t, J=7.2 Hz, 2H), 2.57 (t, J=7.2 Hz, 2H), 1.34 (s, 2H).

Example 28—tert-butyl((R)-1-(((R)-1-((4-(2-(dibenzylamino)acetamido)phenethyl) amino)-1-oxopropan-2-yl)amino)-1-oxopropan-2-yl)carbamate N-(4-(2-aminoethyl)phenyl)-2-(dibenzylamino)acetamide prepared in Example 27 (0,404 g, 1,017 mmol, 1 eq) was dissolved in 4 mL DMF. Methyl D-alanyl-D-alaninate hydrochloride (0,285 g, 1,095 mmol, 1 eq) and HBTU (0,413 g, 1,090 mmol, 1 eq) were added to the stirring solution and cooled to 0° C. in an ice-water bath. NMM (0.115 mL, 1,044 mmol, 1 eq) was added and the solution was left in 30 minutes on ice-water bath and then 3 hours in room temperature. The mixture was diluted with 200 mL water and extracted with 3×50 mL ethyl acetate. The combined organic phases were pooled and washed with 25 mL 0.5M NaHCO₃ and then dried over K₂CO₃, filtered and concentrated under reduced pressure to give 498 mg (80%) ¹H NMR (400 MHz, DMSO) δ 9.57 (s, 1H), 7.91 (t, J=5.7 Hz, 1H), 7.78 (d, J=7.5 Hz, 1H), 7.51-7.30 (m, 11H), 7.30-7.21 (m, 2H), 7.15-7.08 (m, 2H), 7.01 (d, J=7.4 Hz, 1H), 4.19 (p, J=7.1 Hz, 1H), 3.93 (p, J=7.3 Hz, 1H), 3.75 (s, 4H), 3.24 (m, 4H), 2.64 (t, J=7.1 Hz, 2H), 1.38 (s, 9H), 1.15 (dd, J=7.0, 2.0 Hz, 6H).

Example 29—(R)-2-(chloro-15-azanyl)-N—((R)-1-((4-(2-(dibenzylchloro-15-azanyl)acetamido)phenethyl)amino)-1-oxopropan-2-yl)propanamide

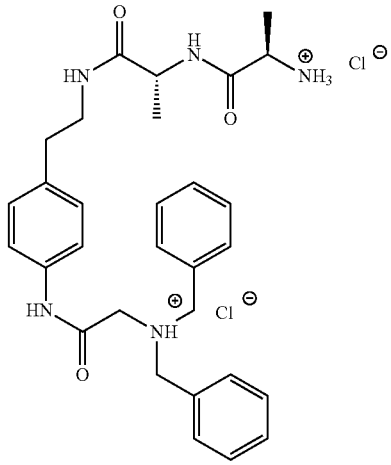

The boc-amine prepared in Example 28 (0.254 g, 0.413 mmol, 1 eq) was dissolved in 25 mL DCM and cooled to 0° C. in an ice-water bath. TFA (2 mL, 26.12 mmol, 63 eq) was dissolved in 25 mL DCM and added drop wise to the stirring solution over the course of 5 minutes. The reaction was left in room temperature for 1 hour. The solution was concentrated under reduced pressure. The mass was resolved in 5 mL dry DCM and added 1 mL 2 M HCl in diethyl ether. There was a precipitate. The precipitate was filtered and washed with diethyl ether and dried under reduced pressure. ¹H NMR (400 MHz, Deuterium Oxide) δ 7.46 (dd, J=6.8, 2.9 Hz, 4H), 7.42-7.29 (m, 6H), 7.17-7.01 (m, 2H), 6.97-6.70 (m, 2H), 4.50 (s, 3H), 4.06 (q, J=7.2 Hz, 1H), 3.93 (q, J=7.0 Hz, 1H), 3.87 (s, 2H), 3.43 (m, 1H), 3.22 (m, 1H), 2.78-2.42 (m, 1H), 1.36 (d, J=7.1 Hz, 3H), 1.11 (d, J=7.2 Hz, 3H)¹³C NMR (101 MHz, D₂O) δ 175.04, 171.09, 164.46, 137.52, 134.34, 132.09, 131.21, 130.16, 130.13, 130.01, 129.05, 122.49, 60.54, 53.02, 50.56, 49.47, 40.89, 34.64, 17.33, 17.14.

Example 30—Preparation of Methyl (2-chloroacetyl)-D-alanyl-D-alaninate

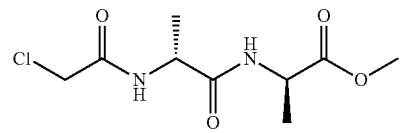 [SMILES: COC(=O)[C@@H](C)NC(=O)[C@@H](C)NC(=O)CCl]

Chloromethyl acetic acid (112 mg, 1.19 mmol) was dissolved in DMF (3 mL) and cooled to 0° C. in an ice-water bath. D-alanyl-D-alanine methyl ester hydrochloride (250 mg, 1.19 mmol) and HATU (452 mg, 1.19 mmol) were then added before NMM (288 μL, 2.62 mmol) was added to the stirring mixture. The mixture was left in the ice-water bath for 30 minutes before slowly heating to room temperature. The mixture was then left for 4 hours at room temperature. The mixture was then diluted with 300 mL water and extracted with 5×30 mL EtOAc. The combined organic phases were pooled and washed with 0.5 M NaHCO₃ (50 mL), 0.1 M HCl (50 mL) and brine (50 mL) before it was dried over MgSO$_4$, filtered and concentrated under reduced pressure. The crude material was then purified by flash column chromatography using SiO$_2$ as stationary phase and 50-100% EtOAc in heptane as eluent. This afforded 274 mg of the title compound as a white powder (92%). $^1$H NMR (400 MHz, DMSO-d6) δ 8.41 (d, J=6.9 Hz, 1H), 8.34 (d, J=7.5 Hz, 1H), 4.43-4.18 (m, 2H), 4.09 (s, 2H), 3.62 (s, 3H), 3.30 (s, OH), 2.50 (s, 8H), 1.28 (d, J=7.3 Hz, 3H), 1.22 (d, J=7.0 Hz, 3H). $^{13}$C NMR (101 MHz, DMSO) δ 172.8, 171.7, 165.3, 51.9, 48.0, 47.5, 42.5, 18.3, 16.8. HRMS e/z calculated for C$_9$H$_{15}$N$_2$O$_4$Cl: 250.0720, found 273.0616 (M+H).

Example 31—Preparation of Methyl bis(pyridin-2-ylmethyl)glycyl-D-alanyl-D-alaninate

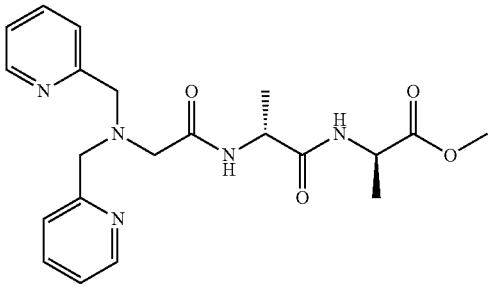 [SMILES: COC(=O)[C@@H](C)NC(=O)[C@@H](C)NC(=O)CN(Cc1ccccn1)Cc1ccccn1]

The □-chloro amide prepared in Example 30 (200 mg, 0.80 mmol, 1.0 eq.) and KI (80 mg, 0.48 mmol, 0.6 eq.) were dissolved in 200 mL MeCN and DPA (173 µL, 0.96 mmol, 1.2 eq.) was added to the stirring mixture. DIPEA (1.35 mL, 7.74 mmol, 9.7 eq.) was then added and the mixture was heated to reflux and left for 16 hours. After cooling to room temperature, the mixture was concentrated under reduced pressure and purified using column chromatography. The product was eluted using 0-5% MeOH in DCM from a neutral alumina column, giving 212 mg (64%). $^1$H NMR (300 MHz, Chloroform-d) δ 9.37 (d, J=7.8 Hz, 1H), 8.74-8.40 (m, 2H), 7.63 (td, J=7.7, 1.8 Hz, 2H), 7.31-7.25 (m, 2H), 7.23-7.13 (m, 3H), 4.54 (pd, J=7.2, 3.3 Hz, 2H), 3.90 (d, J=3.4 Hz, 4H), 3.69 (s, 3H), 3.40 (s, 2H), 1.49 (d, J=7.1 Hz, 3H), 1.30 (d, J=7.2 Hz, 3H). $^{13}$C NMR (75 MHz, CDCl$_3$) δ 173.2, 172.3, 171.8, 158.4, 149.4, 136.7, 123.3, 122.6, 77.6, 77.2, 76:7, 60.4, 58.3, 52.5, 49.0, 48.1, 18.3, 17.5. HRMS e/z calculated for C$_{21}$H$_{27}$N$_5$O$_4$: 413.2063, found 414.2134 (M+H).

Example 32—Preparation of Methyl (2-azidoacetyl)-D-alanyl-D-alaninate

2-Azidoacetic acid (178 µL, 2.38 mmol) was dissolved in DMF (5 mL) and cooled to 0° C. in an ice-water bath. D-alanyl-D-alanine methyl ester hydrochloride (500 mg, 2.38 mmol) and HATU (904 mg, 2.38 mmol) were then added before NMM (576 µL, 5.24 mmol) was added to the stirring mixture. The mixture was left in the ice-water bath for 30 minutes before slowly heating to room temperature. The mixture was then left for 4 hours at room temperature. The mixture was then diluted with 350 mL water and extracted with 5×50 mL EtOAc. The combined organic phases were pooled and washed with 0.5 M NaHCO$_3$ (50 mL), 0.1 M HCl (50 mL) and brine (50 mL) before it was dried over MgSO$_4$, filtered and concentrated under reduced pressure. The crude material was then purified by flash column chromatography using SiO$_2$ as stationary phase and 50-100% EtOAc in heptane as eluent. This afforded 520 mg of the title compound as a white powder (85%). $^1$H NMR (600 MHz, DMSO-d6) δ 8.46 (d, J=7.1 Hz, 1H), 8.33 (d, J=7.3 Hz, 1H), 4.35 (p, J=7.1 Hz, 1H), 4.26 (p, J=7.3 Hz, 1H), 3.82 (s, 2H), 3.61 (s, 3H), 1.28 (d, J=7.3 Hz, 3H), 1.21 (d, J=7.1 Hz, 3H). $^{13}$C NMR (151 MHz, DMSO) δ 173.0, 171.9, 167.1, 52.0, 50.4, 47.8, 47.6, 18.4, 16.9.

Example 33—Preparation of Methyl (2-(4-((bis (pyridin-2-ylmethyl)amino)methyl)-1H-1,2,3-triazol-1-yl)acetyl)-D-alanyl-D-alaninate

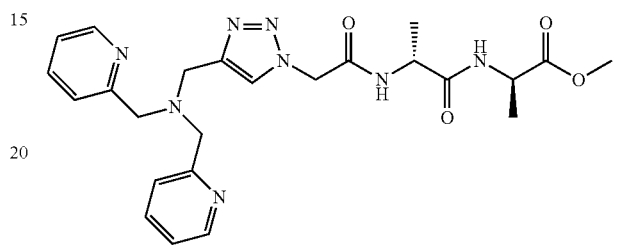

Copper acetate (200 mg, 1.0 mmol, 1.0 eq.) in 2.5 mL H$_2$O and sodium-(+)ascorbate (396 mg, 2.0 mmol, 2.0 eq.) in 2.5 mL H$_2$O were added simultaneously to a stirring solution of the alkyne (237 mg, 1.0 mmol, 1.0 eq.) in 2.5 mL tBuOH. The azide prepared in Example 32 (257 mg, 1.0 mmol, 1.0 eq) was then added and the solution was stirred at room temperature for 16 hours. EDTA (293 mg, 1.0 mmol, 1.0 eq) was then added to the stirring solution and left for 60 minutes before the mixture was diluted with 50 mL H$_2$O and the pH of the mixture was adjusted to >10 with 1M NaOH. The slurry was then extracted with 2×50 mL dichloromethane. The combined organic phases were dried over K$_2$CO$_3$ and concentrated under reduced pressure to give a dark red oil. The crude products were purified using column chromatography by eluting a neutral Al$_2$O$_3$ column with 0-5% methanol in dichloromethane to give 134 mg of the title compound as a pale orange oil (27%). $^1$H NMR (400 MHz, DMSO-d6) δ 8.59 (d, J=7.5 Hz, 1H), 8.49 (d, J=4.7 Hz, 2H), 8.43 (d, J=7.2 Hz, 1H), 8.04 (s, 1H), 7.77 (t, J=7.7 Hz, 2H), 7.57 (d, J=7.8 Hz, 2H), 7.29-7.21 (m, 2H), 5.13 (s, 2H), 4.42-4.21 (m, 2H), 3.77-3.70 (m, 6H), 3.62 (s, 3H), 1.31-1.21 (m, 6H). $^{13}$C NMR (101 MHz, DMSO) δ 172.8, 171.8, 165.0, 159.0, 148.8, 143.1, 136.5, 125.3, 122.5, 122.1, 58.7, 51.8, 51.4, 48.0, 47.9, 47.5, 31.3, 18.3, 16.8. HRMS e/z calculated for C$_{24}$H$_{30}$N$_8$O$_4$: 494.2390, found 495.2463 (M+H).

Example 34—Preparation of methyl (2-(4-((bis (pyridin-2-ylmethyl)amino)methyl)-1H-1,2,3-triazol-1-yl)acetyl)-D-alanyl-D-alaninoic acid

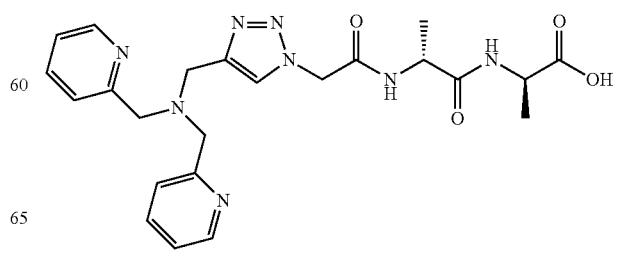

The ester prepared in Example 33 (49 mg, 99 umol) was dissolved in THF (1 mL) cooled to 0° C. using an ice water bath and aqueous 0.5 M lithium hydroxide solution (220 uL, 0.110 mmol). The reaction was stirred for 2.5 h until TLC (5% MeOH in CH$_2$Cl$_2$, alumina) indicated consumption of the ester. The solvent was removed under reduced pressure, and the residue dissolved in water (5 mL). The pH of the solution was adjusted to 7 using 0.1 M HCl and then extracted with ethyl acetate (3×10 mL). The solvent was then removed from the aqueous layer under reduced pressure and the resulting solid dissolved in ethanol and filtered to remove salts and the solvent removed under reduced pressure. This afforded 35 mg of the title compound as a pale green solid (73 umol, 74%). $^1$H NMR (300 MHz, DMSO-d$_6$) δ 8.67 (d, J=7.7 Hz, 1H), 8.53-8.44 (m, 2H), 8.07 (s, 1H), 8.03-7.94 (m, 1H), 7.82-7.71 (m, 2H), 7.64-7.52 (m, 2H), 7.33-7.15 (m, 2H), 5.14 (s, 2H), 4.33 (q, J=7.3 Hz, 1H), 4.09-3.89 (m, 1H), 3.80-3.65 (m, 6H), 1.29-1.14 (m, 6H). $^{13}$C NMR (101 MHz, DMSO) δ 170.9, 165.0, 159.0, 148.8, 143.1, 136.6, 125.3, 122.6, 122.1, 58.7, 51.5, 48.3, 48.0, 18.4, 18.0. e/z calculated for C$_{23}$H$_{28}$N$_8$O$_4$: 480, found 481.3.

Example 35—Preparation of methyl (2-(4-(2-(di-ethoxyphosphoryl)-3-mercapto-propyl)-1H-1,2,3-triazol-1-yl)acetyl)alanylalaninate wise to the reaction mixture, and ice bath was removed to allow solution to reach room temperature (rt). Then reaction mixture was heated at 60° C. for at least 18 hours.

Lithium chloride solution (5%) was added to the mixture, and the product was extracted three times with diethyl ether, washed with water and brine. The organic layer was filtered and dried over sodium sulfate (Na$_2$SO$_4$), and solvent was removed under vacuum. The product was purified by flash chromatography using ethyl acetate:hexane (60:40) as eluent, to afford yellow oil.

Lithiumborohydride (LiBH$_4$) was dissolved in dry TI-IF (2 mL/mmol) at 0° C., and slowly added to the alkylated phosphonoacetate (3) at 0° C. The reaction mixture was stirred at room temperature for 30 minutes, and then irradiated at 80° C. for 10 minutes under microwave. When the mixture reached room temperature, methanol was slowly added, while stirring, until access of LiBH$_4$ was neutralized. The mixture was acidified with 10% citric acid and the product was extracted with diethyl ether, washed with brine solution and dried over Na$_2$SO$_4$. The solvent was removed under vacuum. The product was purified as colorless oil, on flash chromatography with ethyl acetate:acetone 90:10 as eluent.

Triethylamine (1.05 eq) and a catalytic amount of 4-di-methylaminopyridine (DMAP, 20%) was added to a flask containing alcohol derivative (4) in dichloromethane (DCM) (10 mL/mmol). The reaction mixture was stirred for 5 minutes at room temperature. Then, methanesulfonylchloride was slowly added to the solution and stirred for over-

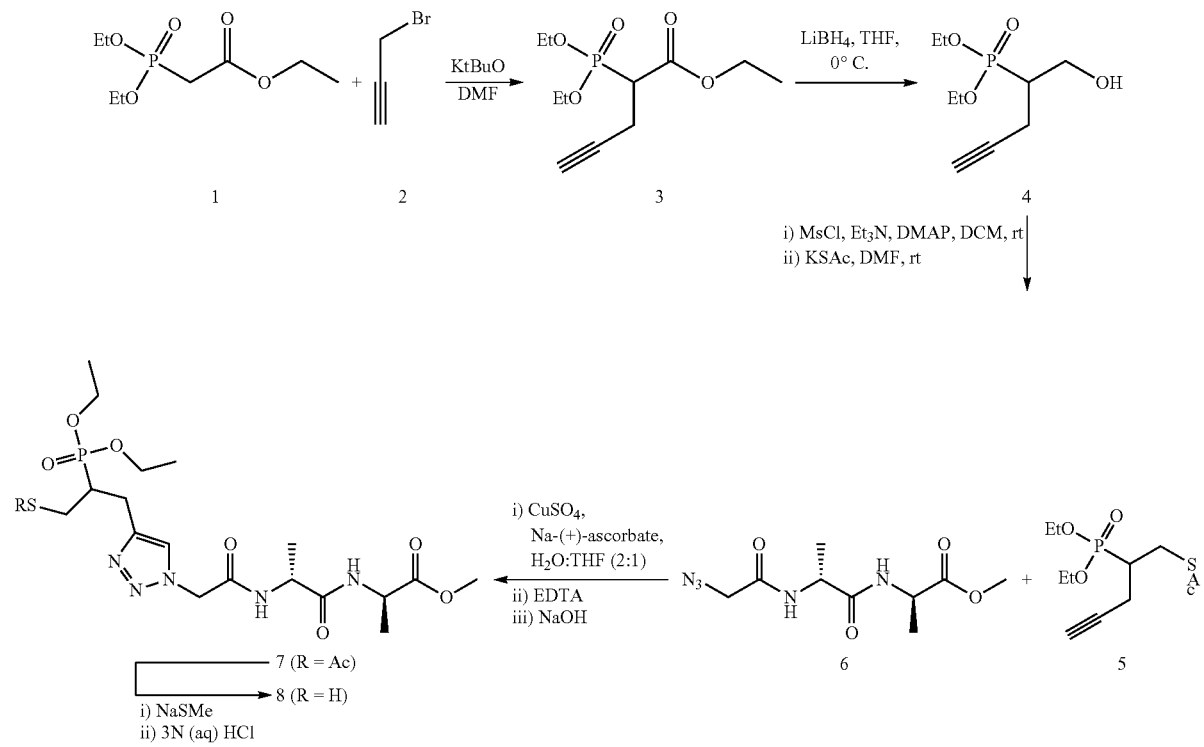

Phosphonoacetate (1) (1 eq) in dry DMF (0.3 mL/mmol) was stirred at 0° C. Potassium tert-butoxide (0.7 eq) was added and the solution was stirred at 0° C. until the base is dissolved. Propargyl bromide (2) (0.7 eq) was added drop night at room temperature. The crude was quenched with 50 mL aqueous NH$_4$Cl and extracted with diethyl ether (3×50 mL). Then the combined organic layers are dried over Na$_2$SO$_4$, filtered, and solvent was evaporated.

The crude was dissolved in DMF (3 mL/mmol). Potassium thioacetate was dissolved in DMF, and added to the crude. Then the reaction mixture was stirred overnight. Solvent was removed under vacuum, and to the resulting brown solid was dissolved in 50 mL NH$_4$Cl, extracted with diethyl ether (2×100) and washed with water (2×100). Organic layer was dried over Na$_2$SO$_4$, filtered and solvent was evaporated under vacuum. The product (5) was purified as orange oil, on flash chromatography using ethyl acetate:acetone (95:05). $^1$H NMR (400 MHz, CDCl$_3$) δ 4.15 (m, 5H), 3.42 (m, 1H), 3.01 (s, 1H), 3.16 (m, 2H) 2.27 (dd, 2H), 2.33 (s, 3H), 1.34 (t, 6H). $^{13}$C NMR (101 MHz, CDCl$_3$) δ 195.03, 80.33, 70.91, 62.83, 62.18, 36.27, 34.87, 30.52, 27.60, 17.58, 16.43. HRMS: (ESI): (M+H)$^+$: calculated for C$_{11}$H$_{20}$O$_4$PS: 279.0817; found 279.0814.

Alkyne (5), (1 eq) and azide (6), (1.2 eq) are added in THF solution and stirred at room temperature. Copper sulfate pentahydrate (1 eq) in H$_2$O and sodium-(+)ascorbate (2.5 eq) in H$_2$O are added into the reaction mixture drop wise and then the solution is stirred at room temperature for 48 hours. EDTA (1 eq) is added to the stirring solution together with 1M NaOH to adjust the pH >10. The reaction mixture is then extracted with EtOAc/DCM. The combined organic phase is dried over K$_2$CO$_3$ and concentrated under reduced pressure. The crude product (7) is purified by using column chromatography.

2M Sodium thiomethoxide (1 eq) in methanol is added to (7), (1 eq) at −20° C. under N$_2$. The mixture is stirred for 30 min at −20° C. The resulting mixture is acidified with 3N HCl (mL) and extracted with ethylacetate (3×-mL). Combined organic layers are dried over MgSO$_4$, filtered and concentrated to give product (8).

Example 36—Preparation of methyl (6-(((tert-butoxycarbonyl)amino)hexanoyl)-D-alanyl-D-alaninate Boc-6-aminohexanoic acid was dissolved in and appropriate solvent, e.g. DMF or DCM and cooled to 0° C. in an ice-water bath. D-alanyl-D-alanine methyl ester hydrochloride and HATU were then added before NMM (576 μL, 5.24 mmol) was added to the stirring mixture. The mixture was left in the ice-water bath for 30 minutes before slowly heating to room temperature. The mixture was then left for 4 hours at room temperature. The mixture was then diluted with water and extracted with 5×50 mL EtOAc. The combined organic phases were pooled and washed with 0.5 M NaHCO$_3$ (50 mL), 0.1 M HCl (50 mL) and brine (50 mL) before it was dried over MgSO$_4$, filtered and concentrated under reduced pressure. The crude material was then purified by flash column chromatography.

Example 37—Preparation of methyl (6-aminohexanoyl)-D-alanyl-D-alaninate

The boc-amine described in Example 36 is dissolved in an appropriate solvent e.g. DCM and cooled to 0° C. in an ice bath before 5-50 equivalents of TFA is added to the mixture. The mixture stirs at 0° C. for 30 minutes and then 4-24 hours at room temperature before concentration under reduced pressure. The crude material is then redissolved in DCM and extracted with 0.5M K$_2$CO$_3$ solution 3×50 mL. The organic phase is then dried over MgSO$_4$, filtered and concentrated. If the compound is not sufficiently pure it is subjected to column chromatography to give the titled compound.

Example 38—Preparation of methyl (6-(((3aS,4R,7R,9R,10R,13R,15R,15aR)-10-(((2S,3R,4S,6R)-3-acetoxy-4-(dimethylamino)-6-methyltetrahydro-2H-pyran-2-yl)oxy)-11-methoxy-3a,4,7,9,11,13,15-heptamethyl-2,6,8,14-tetraoxododecahydro-2H-[1]oxacyclotetradecino[4,3-d]oxazol-1(4H)-yl)hexanoyl)-D-alanyl-D-alaninate

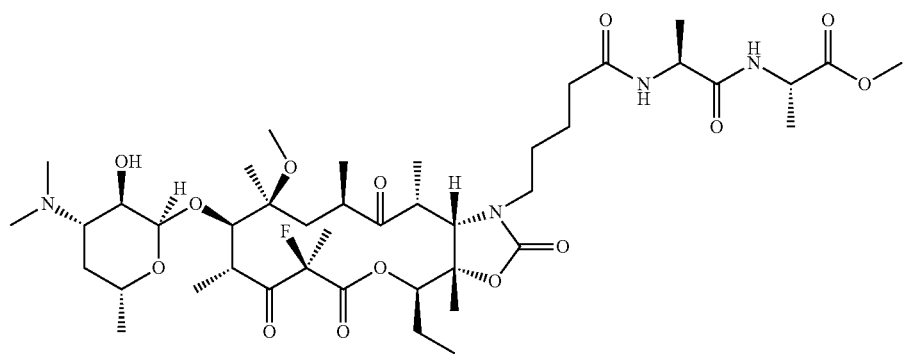

2'-O-acetyl-10,11-didehydro-11-deoxy-12-O-(1H-1-imidazoylcarbonyl)-3-O-des cladinosyl-3-oxo-6-O-methylerythromycin A is suspended in an appropriate solvent mixture, e.g. water:MeCN together with methyl (6-aminohexanoyl)-D-alanyl-D-alaninate as prepared in Example 37. The mixture is heated to 50° C. for 12-72 hours. The crude mixture is diluted with 5% KH$_2$PO$_4$ and EtOAc and extracted. The organic phase is washed with saturated NaCl solution, dried over MgSO$_4$, filtered and concentrated under reduced pressure. The material is then purified by column chromatography to give the title compound.

Example 39—Preparation of (2S,3R,4S,6R)-2-(((3aS,4R,7R,9R,10R,13R,15R,15aR)-1-(4-(2-(bis(pyridin-2-ylmethyl)amino)acetamido)phenethyl)-11-methoxy-3a,4,7,9,11,13,15-heptamethyl-2,6,8,14-tetraoxotetradecahydro-2H-[1]oxacyclotetradecino[4,3-d]oxazol-10-yl)oxy)-4-(dimethylamino)-6-methyltetrahydro-2H-pyran-3-yl acetate

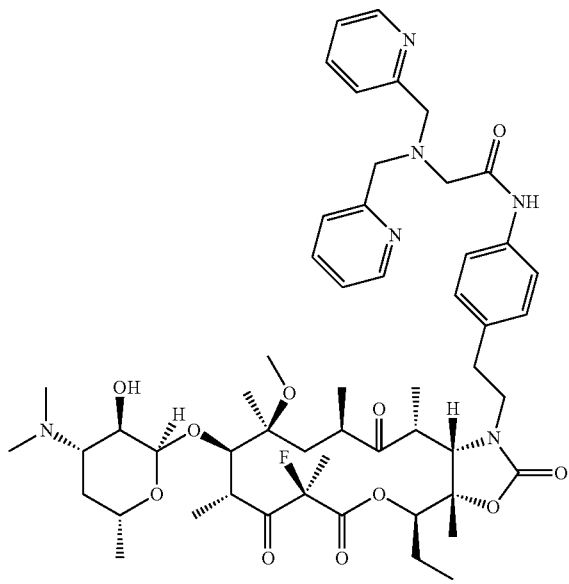 [SMILES: CC[C@H]1OC(=O)[C@](C)(F)C(=O)[C@H](C)[C@@H](O[C@H]2O[C@H](C)C[C@H](N(C)C)[C@H]2O)[C@@](C)(OC)C[C@@H](C)C(=O)[C@H](C)[C@@H]2N(CCc3ccc(NC(=O)CN(Cc4ccccn4)Cc4ccccn4)cc3)C(=O)O[C@@]21C]

2'-O-acetyl-10,11-didehydro-11-deoxy-12-O-(1H-1-imidazoylcarbonyl)-3-O-des cladinosyl-3-oxo-6-O-methylerythromycin A is suspended in an appropriate solvent mixture, e.g. water:MeCN together with N-(4-(2-aminoethyl)phenyl)-2-(bis(pyridin-2-ylmethyl)amino)acetamide. The mixture is heated to 50° C. for 12-72 hours. The crude mixture is diluted with 5% KH$_2$PO$_4$ and EtOAc and extracted. The organic phase is washed with saturated NaCl solution, dried over MgSO4, filtered and concentrated under reduced pressure. The material is then purified by column chromatography to give the title compound.

Example 40—Preparation of (2S,5S,6R)-6-(2-chloroacetamido)-3,3-dimethyl-7-oxo-4-thia-1-azabicyclo[3.2.0]heptane-2-carboxylic acid (+)-6-Aminopenicilanic acid is dissolved in a mixture of water and acetone and cooled to 0° C. in an ice bath. Potassium carbonate is added and the mixture is stirred for 5-10 minutes at 0° C. Chloroacetyl chloride is then added drop wise to the stirring mixture and the mixture is left at 0° C.-r.t. for 4-48 hours until complete. The acetone is removed under reduced pressure and the mixture is acidified. The product is isolated either via filtration of a precipitate or collected by extraction of the acidic water phase with an appropriate organic solvent. If further purification is necessary, the compound is recrystallized or purified by column chromatography.

Example 41—Preparation of (6S,7R)-3-(acetoxymethyl)-7-(2-chloroacetamido)-8-oxo-5-thia-1-azabicyclo[4.2.0]oct-2-ene-2-carboxylic acid 7-Aminocephalosporanic acid is dissolved in a mixture of water and acetone and cooled to 0° C. in an ice bath. Potassium carbonate is added and the mixture is stirred for 5-10 minutes at 0° C. Chloroacetyl chloride is then added drop wise to the stirring mixture and the mixture is left at 0° C.-r.t. for 4-48 hours until complete. The acetone is removed under reduced pressure and the mixture is acidified. The product is isolated either via filtration of a precipitate or collected by extraction of the acidic water phase with an appropriate organic solvent. If further purification is necessary, the compound is recrystallized or purified by column chromatography.

Example 42—Preparation of (2S,5S,6R)-6-(2-(bis(pyridin-2-ylmethyl)amino)acetamido)-3,3-dimethyl-7-oxo-4-thia-1-azabicyclo[3.2.0]heptane-2-carboxylic acid

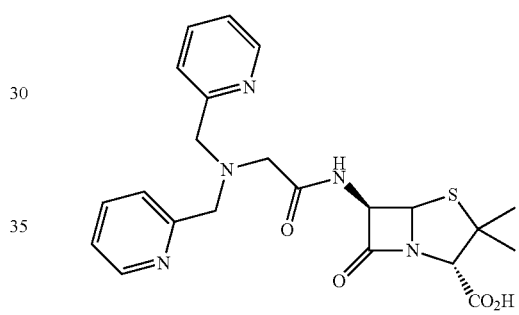

The alpha-chloro amide prepared previously is dissolved in acetonitrile or another appropriate organic solvent. An amine based base e.g. triethylamine or diisopropylethylamine (1-20 eq) is added along with KI and dipicolylamine. The mixture is stirred at 1-72 hours at 25-100° C. until completion. The crude mixture is purified by column chromatography or recrystallization from an appropriate solvent mixture.

Example 43—Preparation of (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylic acid

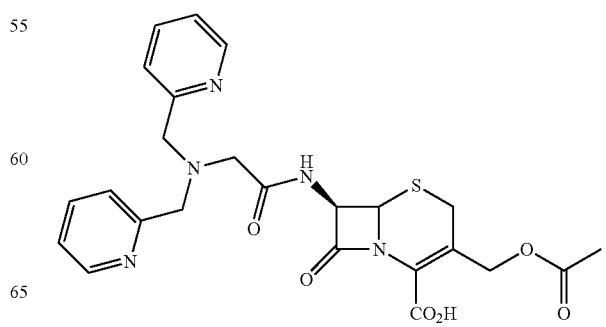

The alpha-chloro amide prepared previously is dissolved in acetonitrile or another appropriate organic solvent. An amine based base e.g. triethylamine or diisopropylethylamine (1-20 eq) is added along with KI and dipicolylamine. The mixture is stirred at 1-72 hours at 25-100° C. until completion. The crude mixture is purified by column chromatography or recrystallization from an appropriate solvent mixture.

Example 44—Preparation of (2S,5S,6R)-6-(2-azido-acetamido)-3,3-dimethyl-7-oxo-4-thia-1-azabicyclo[3.2.0]heptane-2-carboxylic acid 2-Azidoacetic acid is dissolved in DMF and cooled to 0° C. in an ice-water bath. (+)-6-Aminopenicillanic acid and an appropriate coupling agent e.g. HATU, EDC, CDI is then added before NMM is added to the stirring mixture. The mixture is left in the ice-water bath for 30 minutes before slowly heating to room temperature. The mixture was then left for up to 72 hours at room temperature. The mixture is then concentrated under reduced pressure. The crude material is then purified by flash column chromatography or recrystallization.

Example 45—Preparation of (6S,7R)-3-(acetoxymethyl)-7-(2-azidoacetamido)-8-oxo-5-thia-1-azabicyclo[4.2.0]oct-2-ene-2-carboxylic acid 2-Azidoacetic acid is dissolved in DMF and cooled to 0° C. in an ice-water bath. 7-Aminocephalosporanic acid and an appropriate coupling agent e.g. HATU, EDC, CDI is then added before NMM is added to the stirring mixture. The mixture is left in the ice-water bath for 30 minutes before slowly heating to room temperature. The mixture was then left for up to 72 hours at room temperature. The mixture is then concentrated under reduced pressure. The crude material is then purified by flash column chromatography or recrystallization.

Example 46—Preparation of (2S,5S,6R)-6-(2-(4-((bis(pyridin-2-ylmethyl)amino)methyl)-1H-1,2,3-triazol-1-yl)acetamido)-3,3-dimethyl-7-oxo-4-thia-1-azabicyclo[3.2.0]heptane-2-carboxylic acid

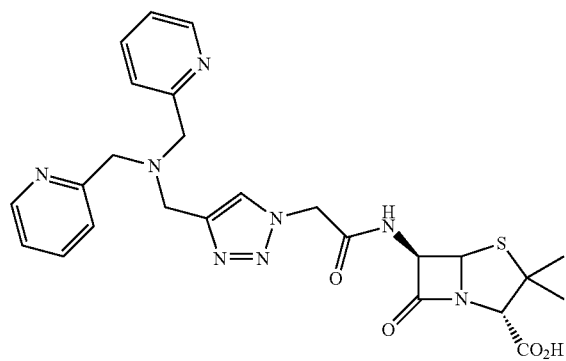 [SMILES: CC1(C)SC2[C@H](NC(=O)Cn3cc(CN(Cc4ccccn4)Cc4ccccn4)nn3)C(=O)N2[C@H]1C(=O)O]

(2S,5S,6R)-6-(2-azidoacetamido)-3,3-dimethyl-7-oxo-4-thia-1-azabicyclo[3.2.0]heptane-2-carboxylic acid and dipicolyl-propagylamine is dissolved in a mixture of water and tert-butanol. Copper acetate or copper sulfate and (+)-sodium ascorbate are dissolved each in water and simultaneously added drop wise to the stirring mixture. The mixture is then left to stand for 2-7 days at room temperature or until completion. The mixture is then concentrated under reduced pressure and purified by chromatography or recrystallization.

Example 47—Preparation of (6S,7R)-3-(acetoxymethyl)-7-(2-(4-((bis(pyridin-2-ylmethyl)amino)methyl)-1H-1,2,3-triazol-1-yl)acetamido)-8-oxo-5-thia-1-azabicyclo[4.2.0]oct-2-ene-2-carboxylic acid

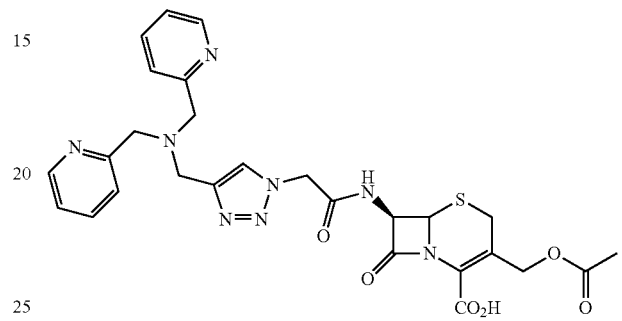

(6S,7R)-3-(acetoxymethyl)-7-(2-azidoacetamido)-8-oxo-5-thia-1-azabicyclo[4.2.0]oct-2-ene-2-carboxylic acid and dipicolyl-propagylamine is dissolved in a mixture of water and tert-butanol. Copper acetate or copper sulfate and (+)-sodium ascorbate are dissolved each in water and simultaneously added drop wise to the stirring mixture. The mixture is then left to stand for 2-7 days at room temperature or until completion. The mixture is then concentrated under reduced pressure and purified by chromatography or recrystallization.

Example 48—Preparation of (2S,5S,6R)-6-(bis(pyridin-2-ylmethyl)amino)-3,3-dimethyl-7-oxo-4-thia-1-azabicyclo[3.2.0]heptane-2-carboxylic acid

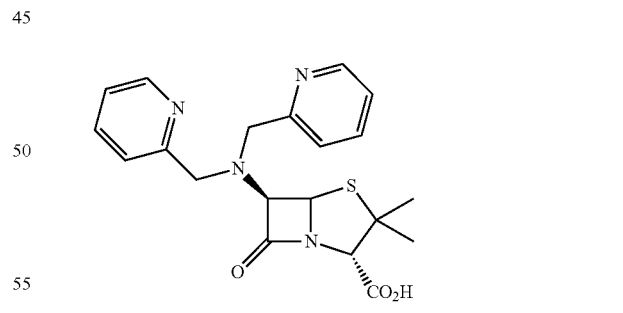

The titled compound is prepared either by alkylation of (+)-6-aminopenicillanic acid with 2-chloromethyl pyridine hydrochloride in an organic solvent with an added base or by reductive alkylation with 2-pyridinecarboxaldehyde in an appropriate solvent e.g. ethanol with either NaB(CN)$_3$H added together with the aldehyde or with NaBH$_4$ added after all the starting material has been consumed. The crude products are then purified by either column chromatography or recrystallization from an appropriate solvent mixture.

Example 49—Preparation of (6S,7R)-3-(acetoxymethyl)-7-(bis(pyridin-2-ylmethyl)amino)-8-oxo-5-thia-1-azabicyclo[4.2.0]oct-2-ene-2-carboxylic acid

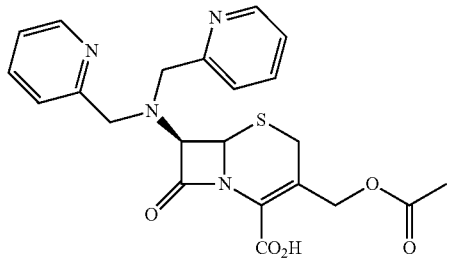 [SMILES: CC(=O)OCC1=C(C(=O)O)N2C(=O)[C@@H](N(Cc3ccccn3)Cc3ccccn3)C2SC1]

The titled compound is prepared either by alkylation of 7-aminocephalosporanic acid with 2-chloromethyl pyridine hydrochloride in an organic solvent with an added base or by reductive alkylation with 2-pyridinecarboxaldehyde in an appropriate solvent e.g. ethanol with either NaB(CN)$_3$H added together with the aldehyde or with NaBH$_4$ added after all the starting material has been consumed. The crude products are then purified by either column chromatography or recrystallization from an appropriate solvent mixture.

Example 50—Preparation of (2S,5S,6R)-6-(2-(bis(pyridin-2-ylmethyl)amino)acetamido)-3,3-dimethyl-7-oxo-4-thia-1-azabicyclo[3.2.0]heptane-2-carboxylic acid

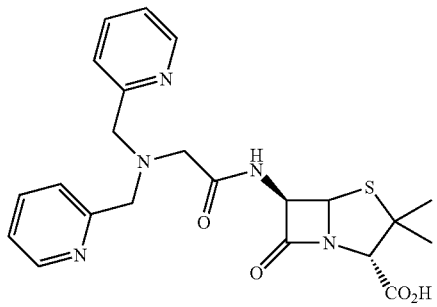 [SMILES: CC1(C)SC2[C@H](NC(=O)CN(Cc3ccccn3)Cc3ccccn3)C(=O)N2[C@H]1C(=O)O]

The ester ethyl bis(pyridin-2-ylmethyl)glycinate is dissolved in H$_2$O and 5 M KOH solution. The mixture is stirred at room temperature for 60 min and the pH is adjusted to 7 with 1 M HCl. The solution is concentrated under reduced pressure to a pale orange sticky solid and it washed with hot absolute ethanol. The combined ethanol is then concentrated under reduced pressure to a brown oil which is used without purification in the next step. (+)-6-Aminopenicillanic acid is mixed with the crude acid, N-methyl morpholine, HOBT, and absolute ethanol and cooled to 10° C. EDC is then added to the stirring solution. The solution is then heated to room temperature and stirred for four hours. The mixture is concentrated under reduced pressure, diluted in H$_2$O and extracted with CH$_2$Cl$_2$. The combined organic phases is dried over K$_2$CO$_3$ and concentrated. The crude product is purified by column chromatography to afford the titled compound.

Example 51—Preparation of (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylic acid

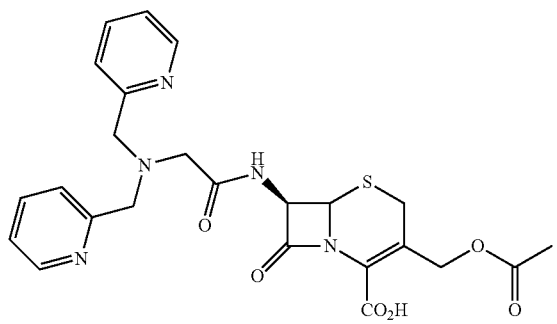 [SMILES: CC(=O)OCC1=C(C(=O)O)N2C(=O)[C@@H](NC(=O)CN(Cc3ccccn3)Cc3ccccn3)C2SC1]

The ester ethyl bis(pyridin-2-ylmethyl)glycinate is dissolved in H$_2$O and 5 M KOH solution. The mixture is stirred at room temperature for 60 min and the pH is adjusted to 7 with 1 M HCl. The solution is concentrated under reduced pressure to a pale orange sticky solid and it washed with hot absolute ethanol. The combined ethanol is then concentrated under reduced pressure to a brown oil which is used without purification in the next step. 7-Aminocephalosporanic acid is mixed with the crude acid, N-methyl morpholine, HOBT, and absolute ethanol and cooled to 10° C. EDC is then added to the stirring solution. The solution is then heated to room temperature and stirred for four hours. The mixture is concentrated under reduced pressure, diluted in H$_2$O and extracted with CH$_2$Cl$_2$. The combined organic phases is dried over K$_2$CO$_3$ and concentrated. The crude product is purified by column chromatography to afford the titled compound.

Example 52—Preparation of methyl (2S,5S,6R)-6-amino-3,3-dimethyl-7-oxo-4-thia-1-azabicyclo[3.2.0]heptane-2-carboxylate A solution of (+)-6-aminopenicillanic acid in methanol is cooled to 0° C. in an ice bath and slowly added either SOCl$_2$, (COCl)$_2$, TMS-CHN$_2$ or CH$_2$N$_2$. The reaction is allowed to reach completion before it is concentrated under reduced pressure. The resulting ester is either purified by extraction, recrystallization or column chromatography or used without further purification in the next reactions.

Example 53—Preparation of methyl (6S,7R)-3-(acetoxymethyl)-7-amino-8-oxo-5-thia-1-azabicyclo[4.2.0]oct-2-ene-2-carboxylate A solution of 7-aminocephalosporanic acid in methanol is cooled to 0° C. in an ice bath and slowly added either SOCl$_2$, (COCl)$_2$, TMS-CHN$_2$ or CH$_2$N$_2$. The reaction is allowed to reach completion before it is concentrated under reduced pressure. The resulting ester is either purified by extraction, recrystallization or column chromatography or used without further purification in the next reactions.

Example 54—Preparation of methyl (2S,5S,6R)-6-(2-azidoacetamido)-3,3-dimethyl-7-oxo-4-thia-1-azabicyclo[3.2.0]heptane-2-carboxylate 2-Azidoacetic acid is dissolved in DMF and cooled to 0° C. in an ice-water bath. Methyl (2S,5S,6R)-6-amino-3,3-dimethyl-7-oxo-4-thia-1-azabicyclo[3.2.0]heptane-2-carboxylate and an appropriate coupling agent e.g. HATU, EDC, CDI is then added before NMM is added to the stirring mixture. The mixture is left in the ice-water bath for 30 minutes before slowly heating to room temperature. The mixture was then left for up to 72 hours at room temperature. The mixture is then concentrated under reduced pressure. The crude material is then purified by flash column chromatography or recrystallization.

Example 55—Preparation of methyl (6S,7R)-3-(acetoxymethyl)-7-(2-azidoacetamido)-8-oxo-5-thia-1-azabicyclo[4.2.0]oct-2-ene-2-carboxylate 2-Azidoacetic acid is dissolved in DMF and cooled to 0° C. in an ice-water bath. Methyl (6S,7R)-3-(acetoxymethyl)-7-amino-8-oxo-5-thia-1-azabicyclo[4.2.0]oct-2-ene-2-carboxylate and an appropriate coupling agent e.g. HATU, EDC, CDI is then added before NMM is added to the stirring mixture. The mixture is left in the ice-water bath for 30 minutes before slowly heating to room temperature. The mixture was then left for up to 72 hours at room temperature. The mixture is then concentrated under reduced pressure. The crude material is then purified by flash column chromatography or recrystallization.

Example 56—Preparation of methyl (2S,5S,6R)-6-(2-(4-((bis(pyridin-2-ylmethyl)amino)methyl)-1H-1,2,3-triazol-1-yl)acetamido)-3,3-dimethyl-7-oxo-4-thia-1-azabicyclo[3.2.0]heptane-2-carboxylate Methyl (2S,5S,6R)-6-(2-azidoacetamido)-3,3-dimethyl-7-oxo-4-thia-1-azabicyclo[3.2.0]heptane-2-carboxylate and dipicolyl-propagylamine is dissolved in a mixture of water and tert-butanol. Copper acetate or copper sulfate and (+)-sodium ascorbate are dissolved each in water and simultaneously added drop wise to the stirring mixture. The mixture is then left to stand for 2-7 days at room temperature or until completion. The mixture is then concentrated under reduced pressure and purified by chromatography or recrystallization.

Example 57—Preparation of methyl (6S,7R)-3-(acetoxymethyl)-7-(2-(4-((bis(pyridin-2-ylmethyl)amino)methyl)-1H-1,2,3-triazol-1-yl)acetamido)-8-oxo-5-thia-1-azabicyclo[4.2.0]oct-2-ene-2-carboxylate Methyl (6S,7R)-3-(acetoxymethyl)-7-(2-azidoacetamido)-8-oxo-5-thia-1-azabicyclo[4.2.0]oct-2-ene-2-carboxylate and dipicolyl-propagylamine is dissolved in a mixture of water and tert-butanol. Copper acetate or copper sulfate and (+)-sodium ascorbate are dissolved each in water and simultaneously added drop wise to the stirring mixture. The mixture is then left to stand for 2-7 days at room temperature or until completion. The mixture is then concentrated under reduced pressure and purified by chromatography or recrystallization.

Example 58—Preparation of (2S,5S,6R)-6-(2-(4-((bis(pyridin-2-ylmethyl)amino)methyl)-1H-1,2,3-triazol-1-yl)acetamido)-3,3-dimethyl-7-oxo-4-thia-1-azabicyclo[3.2.0]heptane-2-carboxylic acid

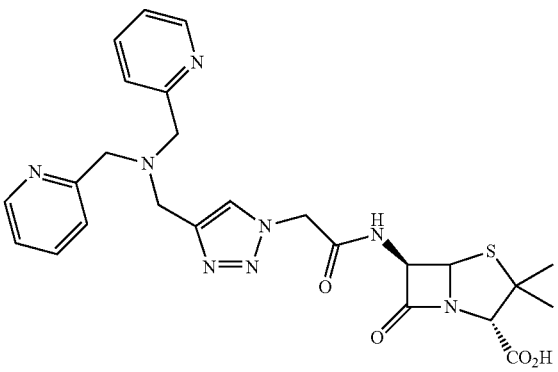 [SMILES: CC1(C)SC2[C@H](NC(=O)Cn3cc(CN(Cc4ccccn4)Cc4ccccn4)nn3)C(=O)N2[C@H]1C(=O)O]

Methyl (2S,5S,6R)-6-(2-(4-((bis(pyridin-2-ylmethyl)amino)methyl)-1H-1,2,3-triazol-1-yl)acetamido)-3,3-dimethyl-7-oxo-4-thia-1-azabicyclo[3.2.0]heptane-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 59—Preparation of (6S,7R)-3-(acetoxymethyl)-7-(2-(4-((bis(pyridin-2-ylmethyl)amino)methyl)-1H-1,2,3-triazol-1-yl)acetamido)-8-oxo-5-thia-1-azabicyclo[4.2.0]oct-2-ene-2-carboxylic acid

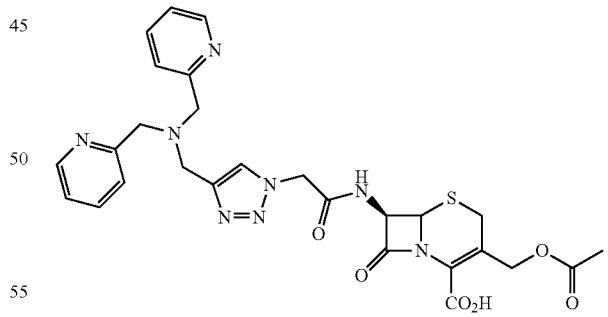

Methyl (6S,7R)-3-(acetoxymethyl)-7-(2-(4-((bis(pyridin-2-ylmethyl)amino)methyl)-1H-1,2,3-triazol-1-yl)acetamido)-8-oxo-5-thia-1-azabicyclo[4.2.0]oct-2-ene-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 60—Preparation of methyl (2S,5S,6R)-6-(2-chloroacetamido)-3,3-dimethyl-7-oxo-4-thia-1-azabicyclo[3.2.0]heptane-2-carboxylate Methyl (2S,5S,6R)-6-amino-3,3-dimethyl-7-oxo-4-thia-1-azabicyclo[3.2.0]heptane-2-carboxylate is dissolved in a mixture of water and acetone and cooled to 0° C. in an ice bath. Potassium carbonate is added and the mixture is stirred for 5-10 minutes at 0° C. Chloroacetyl chloride is then added drop wise to the stirring mixture and the mixture is left at 0° C.-r.t. for 4-48 hours until complete. The acetone is removed under reduced pressure and the mixture is acidified. The product is isolated either via filtration of a precipitate or collected by extraction of the acidic water phase with an appropriate organic solvent. If further purification is necessary, the compound is recrystallized or purified by column chromatography.

Example 61—Preparation of methyl (6S,7R)-3-(acetoxymethyl)-7-(2-chloroacetamido)-8-oxo-5-thia-1-azabicyclo[4.2.0]oct-2-ene-2-carboxylate Methyl (6S,7R)-3-(acetoxymethyl)-7-amino-8-oxo-5-thia-1-azabicyclo[4.2.0]oct-2-ene-2-carboxylate is dissolved in a mixture of water and acetone and cooled to 0° C. in an ice bath. Potassium carbonate is added and the mixture is stirred for 5-10 minutes at 0° C. Chloroacetyl chloride is then added drop wise to the stirring mixture and the mixture is left at 0° C.-r.t. for 4-48 hours until complete. The acetone is removed under reduced pressure and the mixture is acidified. The product is isolated either via filtration of a precipitate or collected by extraction of the acidic water phase with an appropriate organic solvent. If further purification is necessary, the compound is recrystallized or purified by column chromatography.

Example 62—Preparation of methyl (2S,5S,6R)-6-(2-(bis(pyridin-2-ylmethyl)amino)acetamido)-3,3-dimethyl-7-oxo-4-thia-1-azabicyclo[3.2.0]heptane-2-carboxylate Methyl (2S,5S,6R)-6-(2-chloroacetamido)-3,3-dimethyl-7-oxo-4-thia-1-azabicyclo[3.2.0]heptane-2-carboxylate is dissolved in acetonitrile or another appropriate organic solvent. An amine based base e.g. triethylamine or diisopropylethylamine (1-20 eq) is added along with KI and dipicolylamine. The mixture is stirred at 1-72 hours at 25-100° C. until completion. The crude mixture is purified by column chromatography or recrystallization from an appropriate solvent mixture.

Example 63—Preparation of methyl (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylate Methyl (6S,7R)-3-(acetoxymethyl)-7-(2-chloroacetamido)-8-oxo-5-thia-1-azabicyclo[4.2.0]oct-2-ene-2-carboxylate is dissolved in acetonitrile or another appropriate organic solvent. An amine based base e.g. triethylamine or diisopropylethylamine (1-20 eq) is added along with KI and dipicolylamine. The mixture is stirred at 1-72 hours at 25-100° C. until completion. The crude mixture is purified by column chromatography or recrystallization from an appropriate solvent mixture.

Example 64—Preparation of (2S,5S,6R)-6-(2-(bis(pyridin-2-ylmethyl)amino)acetamido)-3,3-dimethyl-7-oxo-4-thia-1-azabicyclo[3.2.0]heptane-2-carboxylic acid

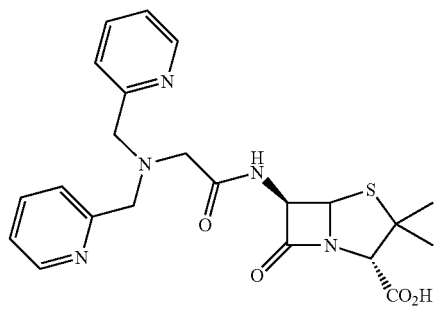 [SMILES: CC1(C)SC2[C@H](NC(=O)CN(Cc3ccccn3)Cc3ccccn3)C(=O)N2[C@H]1C(=O)O]

Methyl (2S,5S,6R)-6-(2-(bis(pyridin-2-ylmethyl)amino)acetamido)-3,3-dimethyl-7-oxo-4-thia-1-azabicyclo[3.2.0]heptane-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 65—Preparation of (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylic acid

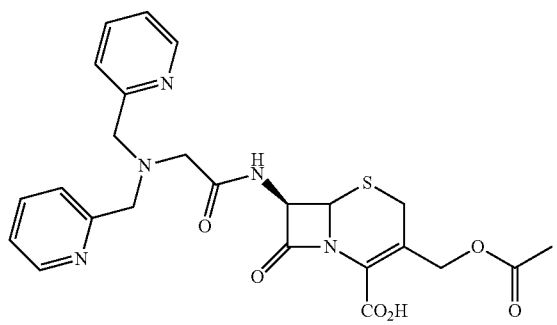 [SMILES: CC(=O)OCC1=C(C(=O)O)N2C(=O)[C@@H](NC(=O)CN(Cc3ccccn3)Cc3ccccn3)C2SC1]

Methyl (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 66—Preparation of methyl (2S,5S,6R)-6-(bis(pyridin-2-ylmethyl)amino)-3,3-dimethyl-7-oxo-4-thia-1-azabicyclo[3.2.0]heptane-2-carboxylate The titled compound is prepared either by alkylation of methyl (2S,5S,6R)-6-amino-3,3-dimethyl-7-oxo-4-thia-1-azabicyclo[3.2.0]heptane-2-carboxylate with 2-chloromethyl pyridine hydrochloride in an organic solvent with an added base or by reductive alkylation with 2-pyridinecarboxaldehyde in an appropriate solvent e.g. ethanol with either NaB(CN)$_3$H added together with the aldehyde or with NaBH$_4$ added after all the starting material has been consumed. The crude products are then purified by either column chromatography or recrystallization from an appropriate solvent mixture.

Example 67—Preparation of methyl (6S,7R)-3-(acetoxymethyl)-7-(bis(pyridin-2-ylmethyl)amino)-8-oxo-5-thia-1-azabicyclo[4.2.0]oct-2-ene-2-carboxylate The titled compound is prepared either by alkylation of methyl (6S,7R)-3-(acetoxymethyl)-7-amino-8-oxo-5-thia-1-azabicyclo[4.2.0]oct-2-ene-2-carboxylate with 2-chloromethyl pyridine hydrochloride in an organic solvent with an added base or by reductive alkylation with 2-pyridinecarboxaldehyde in an appropriate solvent e.g. ethanol with either NaB(CN)$_3$H added together with the aldehyde or with NaBH$_4$ added after all the starting material has been consumed. The crude products are then purified by either column chromatography or recrystallization from an appropriate solvent mixture.

Example 68—Preparation of (2S,5S,6R)-6-(bis(pyridin-2-ylmethyl)amino)-3,3-dimethyl-7-oxo-4-thia-1-azabicyclo[3.2.0]heptane-2-carboxylic acid

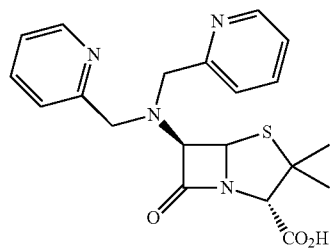 [SMILES: CC1(C)SC2[C@H](N(Cc3ccccn3)Cc3ccccn3)C(=O)N2[C@H]1C(=O)O]

Methyl (2S,5S,6R)-6-(bis(pyridin-2-ylmethyl)amino)-3,3-dimethyl-7-oxo-4-thia-1-azabicyclo[3.2.0]heptane-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 69—Preparation of (6S,7R)-3-(acetoxymethyl)-7-(bis(pyridin-2-ylmethyl)amino)-8-oxo-5-thia-1-azabicyclo[4.2.0]oct-2-ene-2-carboxylic acid

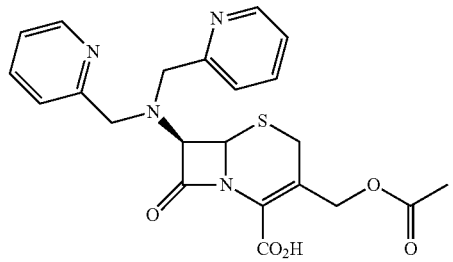 [SMILES: CC(=O)OCC1=C(C(=O)O)N2C(=O)[C@@H](N(Cc3ccccn3)Cc3ccccn3)C2SC1]

Methyl (6S,7R)-3-(acetoxymethyl)-7-(bis(pyridin-2-ylmethyl)amino)-8-oxo-5-thia-1-azabicyclo[4.2.0]oct-2-ene-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 70—Preparation of methyl (2S,5S,6R)-6-(2-(bis(pyridin-2-ylmethyl)amino)acetamido)-3,3-dimethyl-7-oxo-4-thia-1-azabicyclo[3.2.0]heptane-2-carboxylate The ester ethyl bis(pyridin-2-ylmethyl)glycinate is dissolved in H$_2$O and 5 M KOH solution. The mixture is stirred at room temperature for 60 min and the pH is adjusted to 7 with 1 M HCl. The solution is concentrated under reduced pressure to a pale orange sticky solid and it washed with hot absolute ethanol. The combined ethanol is then concentrated under reduced pressure to a brown oil which is used without purification in the next step. Methyl (2S,5S,6R)-6-amino-3,3-dimethyl-7-oxo-4-thia-1-azabicyclo[3.2.0]heptane-2-carboxylate is mixed with the crude acid, N-methyl morpholine, HOBT, and absolute ethanol and cooled to 10° C. EDC is then added to the stirring solution. The solution is then heated to room temperature and stirred for four hours. The mixture is concentrated under reduced pressure, diluted in H$_2$O and extracted with CH$_2$Cl$_2$. The combined organic phases is dried over K$_2$CO$_3$ and concentrated. The crude product is purified by column chromatography to afford the titled compound.

Example 71—Preparation of methyl (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylate The ester ethyl bis(pyridin-2-ylmethyl)glycinate is dissolved in H$_2$O and 5 M KOH solution. The mixture is stirred at room temperature for 60 min and the pH is adjusted to 7 with 1 M HCl. The solution is concentrated under reduced pressure to a pale orange sticky solid and it washed with hot absolute ethanol. The combined ethanol is then concentrated under reduced pressure to a brown oil which is used without purification in the next step. Methyl (6S,7R)-3-(acetoxymethyl)-7-amino-8-oxo-5-thia-1-azabicyclo[4.2.0]oct-2-ene-2-carboxylate is mixed with the crude acid, N-methyl morpholine, HOBT, and absolute ethanol and cooled to 10° C. EDC is then added to the stirring solution. The solution is then heated to room temperature and stirred for four hours. The mixture is concentrated under reduced pressure, diluted in $H_2O$ and extracted with $CH_2Cl_2$. The combined organic phases is dried over $K_2CO_3$ and concentrated. The crude product is purified by column chromatography to afford the titled compound.

Example 72—Preparation of (2S,5S,6R)-6-(2-(bis(pyridin-2-ylmethyl)amino)acetamido)-3,3-dimethyl-7-oxo-4-thia-1-azabicyclo[3.2.0]heptane-2-carboxylic acid

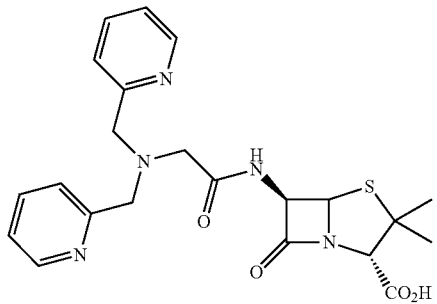 [SMILES: CC1(C)SC2[C@H](NC(=O)CN(Cc3ccccn3)Cc3ccccn3)C(=O)N2[C@H]1C(=O)O]

Methyl (2S,5S,6R)-6-(2-(bis(pyridin-2-ylmethyl)amino)acetamido)-3,3-dimethyl-7-oxo-4-thia-1-azabicyclo[3.2.0]heptane-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 73—Preparation of (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylic acid

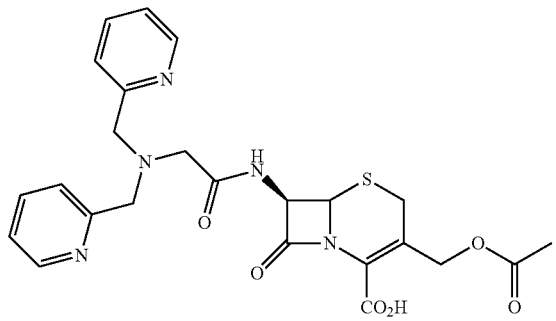 [SMILES: CC(=O)OCC1=C(C(=O)O)N2C(=O)[C@@H](NC(=O)CN(Cc3ccccn3)Cc3ccccn3)C2SC1]

Methyl (6S,7R)-3-(acetoxymethyl)-7-(2-(bis(pyridin-2-ylmethyl)amino)acetamido)-8-oxo-5-thia-1-azabicyclo[4.2.0]oct-2-ene-2-carboxylate is dissolved in THF (1 mL) cooled to 0° C. using an ice water bath and mixed with water and aqueous 0.5 M lithium hydroxide solution. The reaction is stirred for 1-48 hours until completion. The pH of the solution is adjusted to 7 using 0.1 M HCl and the solvent removed under reduced pressure. The mixture is dissolved in absolute ethanol and filtered to remove salts and the solvent removed under reduced pressure. The final product can be purified either using recrystallization from an appropriate solvent or solvent mixture or by chromatography.

Example 74—Determination of $IC_{50}$-Values of Compounds Against Purified MBLs

General Protocol for Determination of $IC_{50}$-Values
Buffers: A: 50 mM HEPES pH 7.2, 100 µM $ZnCl_2$
B: 50 mM HEPES pH 7.2, 100 µM $ZnCl_2$ and 400 µg/ml Bovine Serum Albumin (BSA)
Equipment: SpectraMax 96 well reader
96 well plates
Cuvettes
General plastics: dilution tubes, eppendorfs etc.
Method:
Inhibitors: a. Dissolved in 100% DMSO at a concentration of 10 mM
b. Dissolve the inhibitor in buffer A to a concentration of 25% DMSO. No more than 2.5% DMSO is tolerable in the assay. 100% DMSO (10 mM); 25% DMSO (0.25 mM); 2.5% DMSO (2.5 mM)
c. Make a 2-fold dilution series of the inhibitor. At least 8 dilutions should be made. See example in table 1
Reporter Substrate (Nitrocefin):
a. Dilute a small amount of nitrocefin in 1 ml of DMSO
b. Add 990 µl buffer A+10 µl of nitrocefin to a cuvette.
c. Measure initial OD at absorbance specific for the substrate
d. Add purified enzyme to the cuvette and let the hydrolysis run to completion (the more concentrated enzyme the faster the hydrolysis will run)
e. Measure the end OD
f. Calculate the concentration of substrate: [(End OD−Initial OD)×dilution factor]/Δε (Δε Nitrocefin=17400)
g. Dilute nitrocefin to 100 µM in buffer A
Enzyme: Dilute purified enzyme in buffer B to a concentration of 10 nM.
Assay: a. Set the settings and temperature on the Spectramax/software:
I. Kinetics
II. λ: 482
III. Time: 20 min
IV. Interval: 2-5 sec.
V. Mix before $1^{st}$ read: 5 sec.
VI. Temp: 25° C.
b. Add 30 µl buffer A, 10 µl purified enzyme (final concn. 1 nM), and 10 µl inhibitor to assay wells (duplicates for each inhibitor concentration). Also include a negative control. Wells with no added inhibitor, just 40 µl buffer A. See illustration in table 1.
c. Incubate the plate in the reader for 5 min.
d. Add 50 µl nitrocefin (final concn. 50 µM) to assay wells. This should be done quickly—preferably with an electronic multi-channel pipette.
e. Start the readings immediately.
Determine: the initial velocity ($V_0$) for each inhibitor concentration and calculate $IC_{50}$.

TABLE 1

| Inhibitor dilution series (all values in µM) | | | | | | | |
|---|---|---|---|---|---|---|---|
| [Stock] 2500 | 1250 | 625 | 312.5 | 156.25 | 78.125 | 39.0625 | 19.53125 |
| [well] 250 | 125 | 62.5 | 31.25 | 15.625 | 7.8125 | 3.90625 | 1.953125 |
| [Stock] 9.76563 | 4.88282 | 2.44141 | 0 | 9.76563 | 4.88282 | 2.44141 | 0 |
| [well] 0.976563 | 0.488282 | 0.244141 | 0 | 0.976563 | 0.488282 | 0.244141 | 0 |

Figure 2:
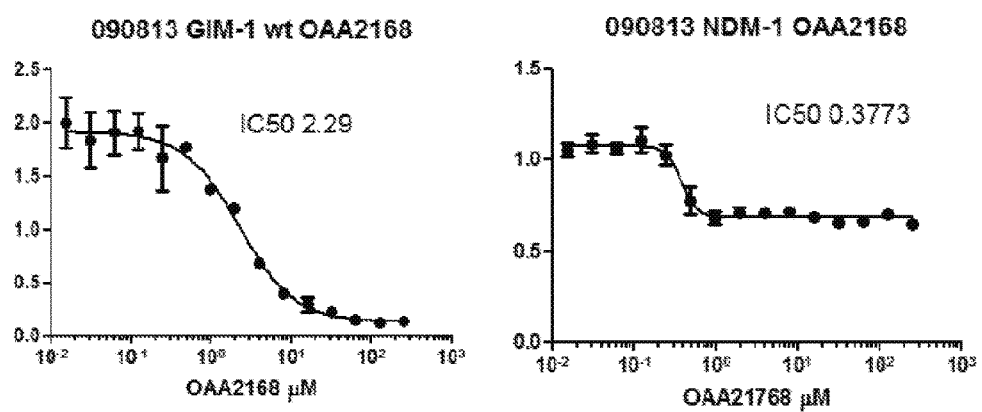
FIG. 2 illustrates the inhibitory curves of the $IC_{50}$ determination for the compound of Example 3.
Figure 3:
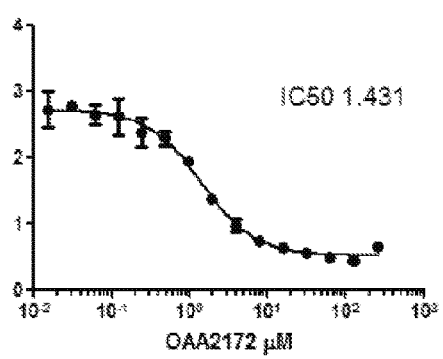
FIG. 3 illustrates the inhibitory curves of the $IC_{50}$ determination for the compound of Example 13.
Figure 3:
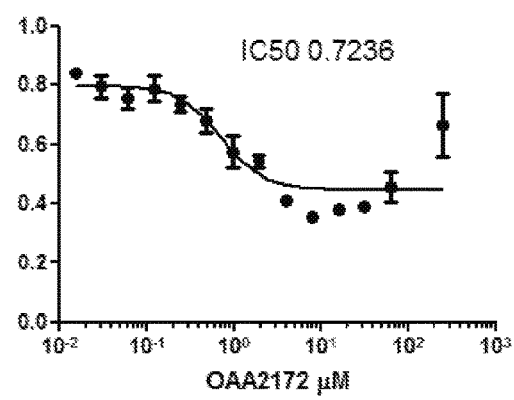
Figure 4:
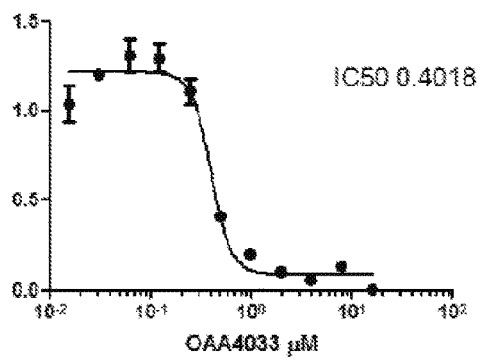
FIG. 4 illustrates the inhibitory curves of the $IC_{50}$ determination for the compound of Example 24.
Figure 4:
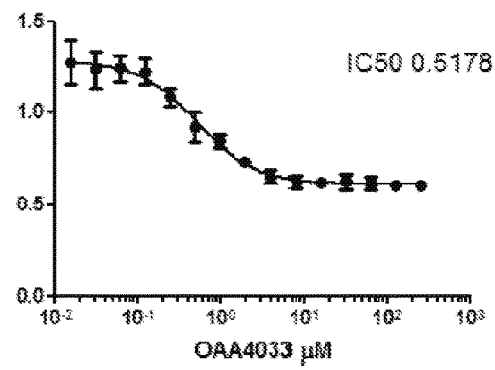

Results:

The results of the $IC_{50}$ determination are presented in Table 2. Examples of inhibitory curves are depicted in the FIGS. 2-4.

TABLE 2

$IC_{50}$-values for selected compounds and reference compound (TPEN)[A].

| Compound Example | $IC_{50}$ (µM) NDM-1 | $IC_{50}$ (µM) VIM-2 | $IC_{50}$ (µM) GIM-1 |
|---|---|---|---|
| TPEN | ND | 0.30 | 0.61 |
| Example 3 | 0.38 | 19.76 | 2.26 |
| Example 13 | 0.72 | 24.9 | 1.43 |
| Example 24 | 0.52 | 22.8 | 0.40 |
| Example 5 | NA | 11.46 | 0.79 |
| Example 6 | NA | 40.9 | 0.71 |
| Example 7 | NA | 18.69 | 0.14 |
| Example 8 | 1.06 | 14.82 | 1.03 |
| Example 9 | 0.60 | 19.03 | 3.15 |
| Example 11 | NA | 12.23 | 0.86 |
| Example 12 | NA | 12.86 | 1.10 |

[A]ND: not determined; NA: experiment was performed, but no proper $IC_{50}$ curve was obtained.

The results show that the compounds inhibit the three different purified MBLs in the µM (VIM-2) and sub-µM range (NDM-1 and GIM-1).

Example 77: Results of MBL Inhibitory Activity in Constructed *E. coli* Cells Expressing MBLs General Protocol for Determination of Inhibitory Activity in *E. Coli* Cells Expressing MBLs
Buffers: Buffer A: 50 mM HEPES pH 7.2, 100 µM $ZnCl_2$
Equipment: SpectraMax 96 well reader
  96 well plates
  Cuvettes
  General plastics: dilution tubes, eppendorfs etc.
Method:
Day 1:
1. Plate out bacterial cells on LB plates with 50 µg/ml kanamycin
Day 2:
1. Inoculate 2-4 colonies in 100 ml LB with 50 µg/ml kanamycin
2. Incubate overnight at 37° C. with shaking
Day 3:
Inhibitor:
  a. Weigh out a small amount of inhibitor (~5 mg) in an eppendorf tube.
  b. Dilute inhibitor with buffer A or buffer A with 25% DMSO to a concentration of 100 mM
Reporter Substrate (Nitrocefin)
  a. Dilute a small amount of nitrocefin in 1 ml DMSO
  b. Add 990 µl buffer A+10 µl of nitrocefin to a cuvette.
  c. Measure initial OD at absorbance 482
  d. Add purified MBL enzyme to the cuvette and let the hydrolysis run to completion
  e. Measure the end OD
  f. Calculate the concentration of substrate: [(Initial OD−End OD)×dilution factor]/Δε
  g. Dilute nitrocefin to 3.2 mM in buffer A or $H_2O$
Overnight Culture:
  a. Dilute the overnight culture to $OD_{600}$=1 in LB broth
Assay:
  a. Transfer 50 µl LB with 0.8 mM IPTG (0.4 mM final concentration in assay) to each well
  b. Add 1 µl inhibitor/positive control (500/1000 µM final concentration in assay) to selected wells
  c. Add 50 µl overnight culture ($OD_{600}$=1) to each well
  d. Incubate in plate reader at 37° C. for 20 min with shaking
  e. Add 5 µl nitrocefin (3.2 mM) to selected wells with a multichannel pipette
  f. Incubate the plate in the plate reader for 3 hours, measuring nitrocefin hydrolysis at $A_{482}$ every minute, with shaking in-between
  g. Measure endpoint at $A_{600}$ to see how inhibitor alone effects bacterial growth
  h. Centrifuge the plate at 2800 rpm for 10 min, and transfer 50 µl to clean wells
  i. Measure $A_{482}$ endpoint
Results:
The results showing the inhibition of VIM-2 and GIM-1 expressed in *E. coli* are presented in Table 3.

TABLE 3

Inhibition (%) of MBLs in whole cell experiment with VIM-2 and GIM-1. The cells were *E. coli* SNO3 containing the vector pET26b-bla$_{VIM-2}$ or pET26b-bla$_{GIM-1}$. Test substances were used at a concentration of 250 µM.

| Compound | % inhibition of VIM-2 | % inhibition of GIM-1 |
|---|---|---|
| Example 3 | 74.05 | 15.65 |
| Example 13 | 82.05 | 20.55 |
| Example 24 | 98.25 | 69.20 |
| Example 5 | 73.75 | 14.40 |
| Example 6 | 82.10 | 20.65 |
| Example 7 | 75.35 | 12.50 |
| Example 8 | 82.95 | 22.20 |
| Example 9 | 84.20 | 14.75 |
| Example 11 | 75.10 | 16.50 |
| Example 12 | 64.25 | 15.70 |

The results show that the compounds are able to pass across the outer membrane of *E. coli* and inhibit the MBLs located in the periplasmic space. A varying degree of inhibition is observed between the compounds and the inhibitory activity was strongest against VIM-2 compared to GIM-1.

Example 78—Results of Microbroth Dilution Method for Evaluating Synergistic Effect of Compounds with Meropenem General Protocol for Microbroth Dilution Method for Evaluating Antibacterial Activity of Compounds or Synergistic Effect of Compound-Antibiotic Combination
Preparation of Bacteria
Day 1:
Plate bacterial strain(s) on appropriate media:
  Gram-negative bacteria with ESBLs or carbapenemases: green agar plates with 100 mg/L ampicillin Gram-negative bacteria without β-lactamases: green agar plates
Gram-positive bacteria (Staphylococci and Enterococci): blood agar plates
Incubate o.n. at 37° C.
Day 2:
Prepare the Bacterial Inoculum:
Prepare a 0.5 McFarland suspension of bacteria in 0.85% NaCl. (Should be used within 15 min of preparation).

Add 100 µl MH broth to row 1
Add 50 µl bacterial suspension to row 2-12.
Incubate the plate for 20 hrs at 37° C. and determine the MIC in the presence and absence of inhibitor.
Results:
The minimum inhibitory concentration (MIC) of meropenem against clinical Gram-negative isolates both positive and negative for MBLs in the presence and absence of compounds are shown in Table 4.

TABLE 4

Meropenem (MEM) minimum inhibitory concentration (MIC, mg/L) against clinical bacterial isolates in the absence and presence of MBL inhibitory compounds at 125 µM[A].

| | | | | | MIC (mg/L) | | | | |
|---|---|---|---|---|---|---|---|---|---|
| Ref. no | K34-7 | 50692172 | K66-45 | A3-81 | K71-77 | 50639799 | 50808021 | 50732159 | 50739467 |
| Species | P. aeruginosa | P. aeruginosa | K. pneumoniae | K. pneumoniae | E. coli | E. coli | P. aeruginosa | K. pneumoniae | E. coli |
| MBL gene | VIM-2 | NDM-1 | NDM-1 | VIM-1 | NDM-1 | VIM-1 | Negative | Negative | Negative |
| MEM | 32-64 | 32-128 | 32-64 | 64-256 | 1-4 | 8-16 | 128 | 32 | 0.5 |
| MEM + Ex. 24 | ≤1 | ≤0.5 | ≤0.5 | ≤0.5 | ≤0.064 | ≤0.064 | 128-256 | 32 | 0.5 |
| MEM + Ex. 12 | 16 | 16 | 8 | 32 | 1-2 | 2 | ND | ND | ND |
| MEM + Ex. 13 | 8-16 | 4-8 | 1-2 | 16 | 0.25-0.5 | 0.5 | ND | ND | ND |
| MEM + Ex. 9 | 4-8 | 32 | 4 | 32 | 0.5 | 2-4 | ND | ND | ND |
| MEM + Ex. 6 | 4 | 8-16 | 1 | 3216 | 0.125 | 0.5-1 | ND | ND | ND |
| MEM + Ex. 33 | 2 | 2 | ≤0.5 | 8 | ≤0.064-0.064 | 0.25 | ND | ND | ND |
| MEM + Ex. 30 | 32 | 32 | 32 | 64 | 2 | 16 | ND | ND | ND |
| MEM + Ex. 19 | 32 | 64 | 8-16 | 64 | 2 | 2 | ND | ND | ND |
| MEM + Ex. 31 | 16 | 16 | 8-16 | 32 | 0.5-1 | 2 | ND | ND | ND |
| MEM + TPEN | 1 | ≤0.5 | ≤0.5 | ≤0.5 | ≤0.064 | ≤0.064 | 64 | ≤0.064 | 1 |
| MEM + Captopril | 32 | 32-64 | 64 | 64-128 | 2-4 | 16 | ND | ND | ND |

[A]ND: not determined

Dilute the 0.5 McFarland suspension 1:100 into MH broth. Check the inoculum by diluting the prepared bacterial suspension 1:100 (10 µl bacterial suspension+990 µl 0.85% NaCl). Plate 10 µl of the dilution on MH agar plates (×2). Incubate o.n. at 37° C., count the colonies and calculate the final CFU/ml inoculum in the plate by multiplying the average number of colonies with 10000 and divide by 2. The final inoculum should be between $3$-$7 \times 10^5$ CFU/ml.
Add 50 µl of the prepared bacterial suspension to each well in the microtiter plate except negative growth control.
Preparation of Compounds/Antibiotics
Calculate the desired concentration-range and volume of the compounds/antibiotics in the assay. For antibiotics this will depend on the MIC to meropenem of the bacterial strains to be tested. Dilute the stock solution in MH broth. Make subsequent 2-fold dilutions in MH broth of the desired concentrations if a concentration range is to be tested (remember the extra dilution factor in the assay plate). Always include extra volume for pipetting. Take into consideration stock solutions that are made in buffers that have an effect on bacterial growth (e.g. DMSO).
Assay:
Determining the MIC of compounds/antibiotics alone:
Add 25 µl of each concentration of compound/antibiotic to row 2-11 (highest concentration in row 2)
Add 25 µl MH broth to row 2-11
Add 50 µl MH broth to row 12 (positive control)
Add 100 µl MH broth to row 1
Add 50 µl bacterial suspension to row 2-12.
Determining the MIC of antibiotics+compounds:
Add 25 µl of each concentration of antibiotic to row 2-11 (highest concentration in row 2)
Add 25 µl of compound to row 2-11
Add 50 µl MH broth to row 12 (positive control)

In summary, the lead hit OAA4033 (Example 24) and several of our candidates show strong synergistic potentiation of meropenem restoring the antimicrobial activity against different clinical strains of MBL-producing P. aeruginosa, K. pneumoniae and E. coli. The synergistic effect was irrespective of species. No synergistic effect was observed with OAA4033 (Example 24) and OAA4085 (Example 12) in MBL-negative clinical strains indicating that the effect is specific for MBL-producing isolates. Testing of intrinsic antimicrobial activity of the compounds showed that all had an MIC of ≥1000 µM ruling out intrinsic antimicrobial activity of the compounds. Synergistic activity with meropenem and TPEN was also observed as expected. It should be noted that TPEN for some isolates showed intrinsic antimicrobial activity (MICs 250 µM-1000 µM) just above the tested concentration (125 µM) in the assay. No synergistic activity was observed with captopril.

The invention claimed is:
1. A method of treating a bacterial infection in a human or non-human mammal, said method comprising administration to said mammal of an effective amount of a compound according to formula I, or a pharmaceutically acceptable salt thereof:

A-L-B wherein
A comprises a group of formula III:

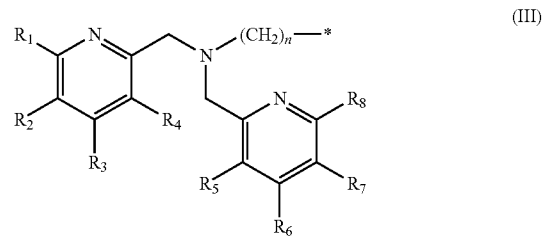

(III)

wherein $R_1$ to $R_8$ are hydrogen;

n is 1; and

* denotes the point of attachment of A to the linker, L;

L comprises an alkylene chain in which one or more —$CH_2$— groups of the alkylene chain may be replaced by a group independently selected from —CO—, —NH—, and a monocyclic ring which is carbocyclic or heterocyclic; and B is a vector which is -D-Ala-D-Ala or a derivative thereof, in combination with a β-lactam antibiotic, wherein the infection is associated with Gram negative bacteria which comprise metallo-β-lactamases and which are resistant to said β-lactam antibiotic.

2. The method according to claim 1, wherein the compound and β-lactam antibiotic are provided in the same formulation or in different formulations.

3. The method according to claim 1, wherein linker L comprises a $C_{1-6}$ alkylene chain in which one or more —$CH_2$— groups of the alkylene chain may be replaced by a group independently selected from —CO—, —NR"— (wherein each R" is H), and a monocyclic ring which is a carbocyclic or heterocyclic ring.

4. The method according to claim 3, wherein said alkylene chain is interrupted by an aryl or heteroaryl ring.

5. The method according to claim 3, wherein said linker is interrupted by a phenyl or triazole ring.

6. The method according to claim 1, wherein the compound is

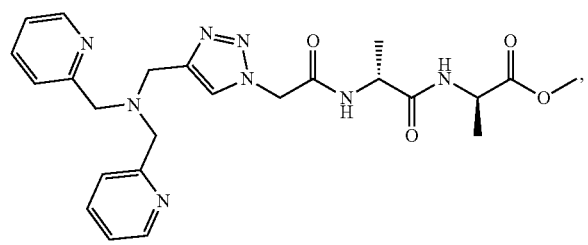 [SMILES: COC(=O)[C@@H](C)NC(=O)[C@@H](C)NC(=O)Cn1cc(CN(Cc2ccccn2)Cc2ccccn2)nn1]

or a pharmaceutically acceptable salt thereof.

7. The method according to claim 1 comprising administration of an effective amount of said compound according to formula I, or a pharmaceutically acceptable salt thereof, simultaneously, separately or sequentially with said β-lactam antibiotic.

8. The method according to claim 1 wherein the derivative of -D-Ala-D-Ala is the hydrochloride salt or methyl ester.

9. The method according to claim 1 wherein the compound according to formula I is selected from

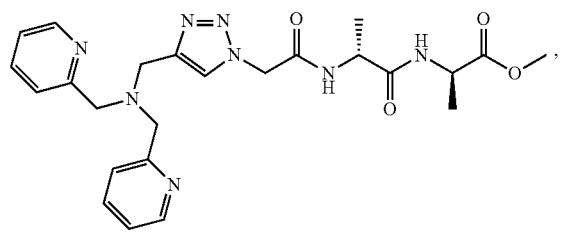

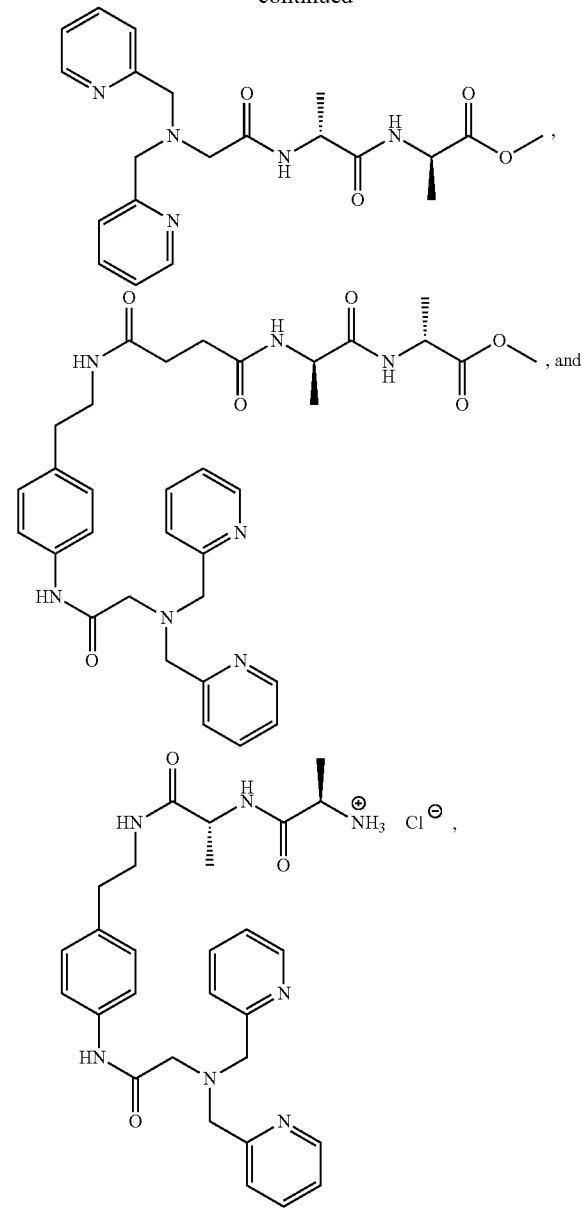

or a pharmaceutically acceptable salt thereof.

10. A method of treating a bacterial infection in a human or non-human mammal, said method comprising the step of administering to said mammal an effective amount of a composition comprising a compound according to formula I, or a pharmaceutically acceptable salt thereof:

A-L-B wherein

A comprises a group of formula III:

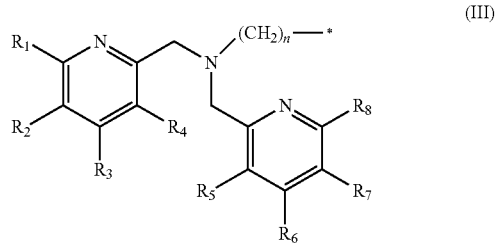

wherein $R_1$ to $R_8$ are hydrogen;

n is 1; and

* denotes the point of attachment of A to the linker, L;

L comprises an alkylene chain in which one or more —CH$_2$— groups of the alkylene chain may be replaced by a group independently selected from —CO—, —NH—, and a monocyclic ring which is carbocyclic or heterocyclic; and B is a vector which is -D-Ala-D-Ala or a derivative thereof, together with one or more pharmaceutically acceptable carriers or excipients, in combination with a β-lactam antibiotic, wherein the infection is associated with Gram negative bacteria which comprise metallo-β-lactamases and which are resistant to said β-lactam antibiotic.

11. The method according to claim 10, wherein said Gram negative bacteria include *Pseudomonas aeruginosa, Acinetobacter baumannii* and Enterobacteriaceae.

12. The method according to claim 10, wherein the compound and β-lactam antibiotic are provided in the same formulation or in different formulations.

13. The method according to claim 10 comprising administration of an effective amount of said compound according to formula I, or a pharmaceutically acceptable salt thereof, simultaneously, separately or sequentially with said β-lactam antibiotic.

14. The method according to claim 10 wherein the derivative of -D-Ala-D-Ala is the hydrochloride salt or methyl ester.

15. The method according to claim 10 wherein the compound according to formula I is selected from

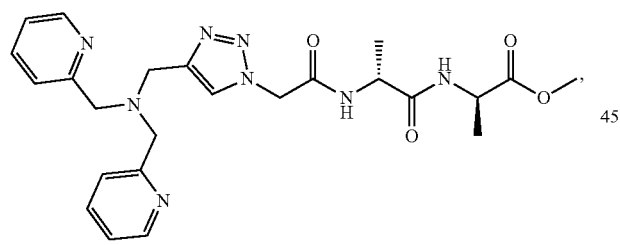

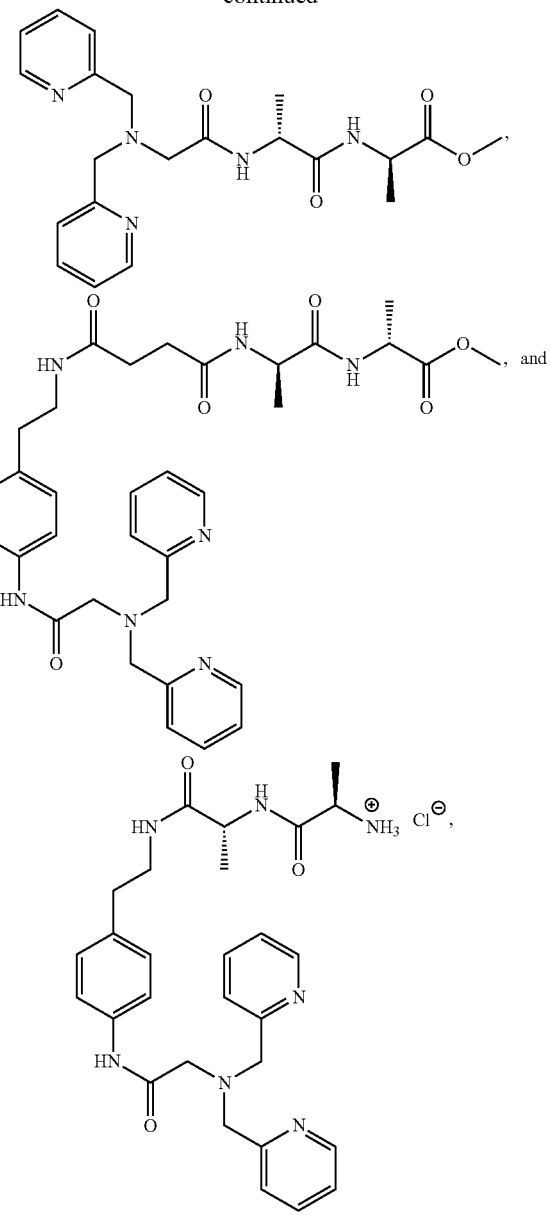

or a pharmaceutically acceptable salt thereof.

* * * * *